(12) United States Patent
Mummery et al.

(10) Patent No.: US 10,119,122 B2
(45) Date of Patent: Nov. 6, 2018

(54) DIFFERENTIATION AND EXPANSION OF ENDOTHELIAL CELLS FROM PLURIPOTENT STEM CELLS AND THE IN VITRO FORMATION OF VASCULATURE LIKE STRUCTURES

(71) Applicant: Academisch Ziekenhuis Leiden, Leiden (NL)

(72) Inventors: Christine Lindsay Mummery, Leiden (NL); Valeriya Viktorovna Orlova, Leiden (NL)

(73) Assignee: ACADEMISCH ZIEKENHUIS LEIDEN, Leiden (NL)

( * ) Notice: Subject to any disclaimer, the term of this patent is extended or adjusted under 35 U.S.C. 154(b) by 62 days.

(21) Appl. No.: 14/897,619

(22) PCT Filed: Jun. 10, 2014

(86) PCT No.: PCT/NL2014/050373
§ 371 (c)(1),
(2) Date: Dec. 10, 2015

(87) PCT Pub. No.: WO2014/200340
PCT Pub. Date: Dec. 18, 2014

(65) Prior Publication Data
US 2016/0115453 A1  Apr. 28, 2016

(30) Foreign Application Priority Data
Jun. 10, 2013 (NL) ........................... 2010949

(51) Int. Cl.
*C12N 5/071* (2010.01)
*G01N 33/50* (2006.01)

(52) U.S. Cl.
CPC ........... *C12N 5/0691* (2013.01); *C12N 5/069* (2013.01); *G01N 33/5061* (2013.01); *G01N 33/5064* (2013.01); *C12N 2500/90* (2013.01); *C12N 2501/15* (2013.01); *C12N 2501/155* (2013.01); *C12N 2501/16* (2013.01); *C12N 2501/165* (2013.01); *C12N 2501/415* (2013.01); *C12N 2501/727* (2013.01); *C12N 2503/06* (2013.01); *C12N 2506/45* (2013.01)

(58) Field of Classification Search
CPC ........... C12N 2500/90; C12N 2501/15; C12N 2501/155; C12N 2501/16; C12N 2501/165; C12N 2501/415; C12N 2501/727; C12N 2503/06; C12N 2506/45; C12N 5/069; C12N 5/0691; G01N 33/5061; G01N 33/5064
USPC ........... 435/307.1, 325, 377; 506/10
See application file for complete search history.

(56) References Cited

U.S. PATENT DOCUMENTS

| | | | |
|---|---|---|---|
| 5,843,780 A | 12/1998 | Thomson | |
| 6,200,806 B1 | 3/2001 | Thomson | |
| 6,833,269 B2 | 12/2004 | Carpenter | |
| 7,029,913 B2 | 4/2006 | Thomson | |
| 8,329,175 B2 * | 12/2012 | Sukhatme | C07K 16/18 424/138.1 |
| 2009/0227469 A1 | 9/2009 | Conklin et al. | |
| 2010/0233132 A1 | 9/2010 | Ferreira et al. | |
| 2010/0279403 A1 * | 11/2010 | Rajesh | C12N 5/0647 435/366 |
| 2010/0279893 A1 | 11/2010 | Svendsen et al. | |
| 2012/0301443 A1 | 11/2012 | Raffi et al. | |
| 2012/0322151 A1 | 12/2012 | Gerecht et al. | |

FOREIGN PATENT DOCUMENTS

| | | | |
|---|---|---|---|
| WO | 2007140340 | 12/2007 | |
| WO | 2011090684 | 7/2011 | |
| WO | 2011106681 | 9/2011 | |
| WO | WO 2012168167 A1 * | 12/2012 | C12N 5/069 |
| WO | 2013069661 | 5/2013 | |
| WO | 2013137567 | 9/2013 | |
| WO | 2013166165 | 11/2013 | |
| WO | 2012168167 | 12/2013 | |
| WO | 2014200340 | 12/2014 | |

OTHER PUBLICATIONS

PCT International Search Report dated Sep. 22, 2014, PCT/NL2014/050373.
Andries D. Van Der Meer et al., Three-dimensional co-cultures of human endothelial cells and embryonic stem cell-derived pericytes inside a microfluidic device, Lab on a Chip, May 23, 2013, pp. 3562-3568, vol. 13, No. 18, RSC Publishing.
Kyung-Dal Choi et al., Hematopoietic and Endothelial Differentiation of Human Induced Pluripotent Stem Cells, Stem Cells, Mar. 2009, vol. 27, No. 3.
M. Costa et al., Derivation of endothelial cells from human embryonic stem cells in fully defined medium enables identification of lysophosphatidic acid and platelet activating factor as regulators of eNOS localization, Stem Cell Research, Jan. 2013, pp. 103-117, vol. 10, No. 1.
Katherine Hill et al., Human embryonic stem cell-derived vascular progenitor cells capable of endothelial and smooth muscle cell function, Experimental Hematology, Mar. 2010, pp. 246-257, vol. 38, No. 3, Elsevier Inc.

(Continued)

*Primary Examiner* — Janet L Epps-Smith
(74) *Attorney, Agent, or Firm* — TraskBritt, P.C.

(57) ABSTRACT

The disclosure is concerned among others with means and methods for obtaining endothelial cells and to means and methods for in vitro cell culture comprising endothelial cells and pericytes and/or smooth muscle cells derived from the pericytes. The endothelial cells or the pericytes and/or smooth muscle cells, or both, are preferably derived from in vitro differentiated pluripotent stem cells.

17 Claims, 31 Drawing Sheets
Specification includes a Sequence Listing.

(56) References Cited

OTHER PUBLICATIONS

Valeria V. Orlova et al., Functionality of Endothelial Cells and Pericytes From Human Pluripotent Stem Cells Demonstrated in Cultured Vascular Plexus and Zebrafish Xenografts, Arteriosclerosis, Thrombosis, and Vascular Biology, Jan. 2014, pp. 177-186, vol. 34, No. 1.

Valeria V. Orlova et al., Functionality of Endothelial Cells and Pericytes From Human Pluripotent Stem Cells Demonstrated in Cultured Vascular Plexus and Zebrafish Xenografts. Data Supplement 1. Materials and Methods, Arteriosclerosis, Thrombosis, and Vascular Biology, Oct. 24, 2013, pp. M1-M6.

Valeria V. Orlova et al., Functionality of Endothelial Cells and Pericytes From Human Pluripotent Stem Cells Demonstrated in Cultured Vascular Plexus and Zebrafish Xenografts. Data Supplement 2. Supplemental figures, Arteriosclerosis, Thrombosis, and Vascular Biology, Oct. 24, 2013, pp. S1-S15.

Valeria V. Orlova et al., Generation, expansion and functional analysis of endothelial cells and pericytes derived from human pluripotent stem cells, Nature Protocols, Jun. 2014, pp. 1514-1531, vol. 9, No. 6.

Gaoyang Liang et al., Genetic and Epigenetic Variations in iPSCs: Potential Causes and Implications for Application, Cell Stem Cell, Aug. 2013, pp. 149-159, vol. 13, No. 2, Cell Press.

Andries D. Van Der Meer et al., Three-dimensional co-cultures of human endothelial cells and embryonic stem cell-derived pericytes inside a microfluidic device. Supplementary figures, Lab on a Chip, May 23, 2013, pp. S1-S5, vol. 13, No. 18, RSC Publishing.

Armulik et al., Pericytes: Developmental Physiological and Pathological Perspectives, Problems and Promises, Developmental Cell Review, Cell Press, Aug. 16, 2011, pp. 193-215, vol. 21, Elsevier Inc.

Patterson et al., Defining the nature of human pluripotent stem cell progeny, Cell Research, published online Aug. 16, 2011, pp. 178-193, vol. 22.

Chin et al., Induced Pluripotent Stem Cells and Embryonic Stem Cells Are Distinguished by Gene Expression Signatures, Cell Stem Cell, Jul. 2009, pp. 111-123, vol. 5, No. 1.

Choi et al., A comparison of genetically matched cell lines reveals the equivalence of human iPCSs and ESCs, Nature Biotechnology, Nov. 2015, pp. 1173-1181, vol. 33, No. 11.

Genetic Engineering & Biotechnology News, Oct. 30, 2015, at https://www.genengnews,com/print/39784, 3 pages.

Harvard Stem Cell Institute, Oct. 29, 2015, at https://hsci.harvard.edu/news/are-embryonic-stem-cells-and-artificial-stem-cells-equivalent, 3 pages.

European Patent Office Communication for copending application 14 737 024.1, dated Jun. 18, 2018, 5 pages.

\* cited by examiner

Fig. 3C
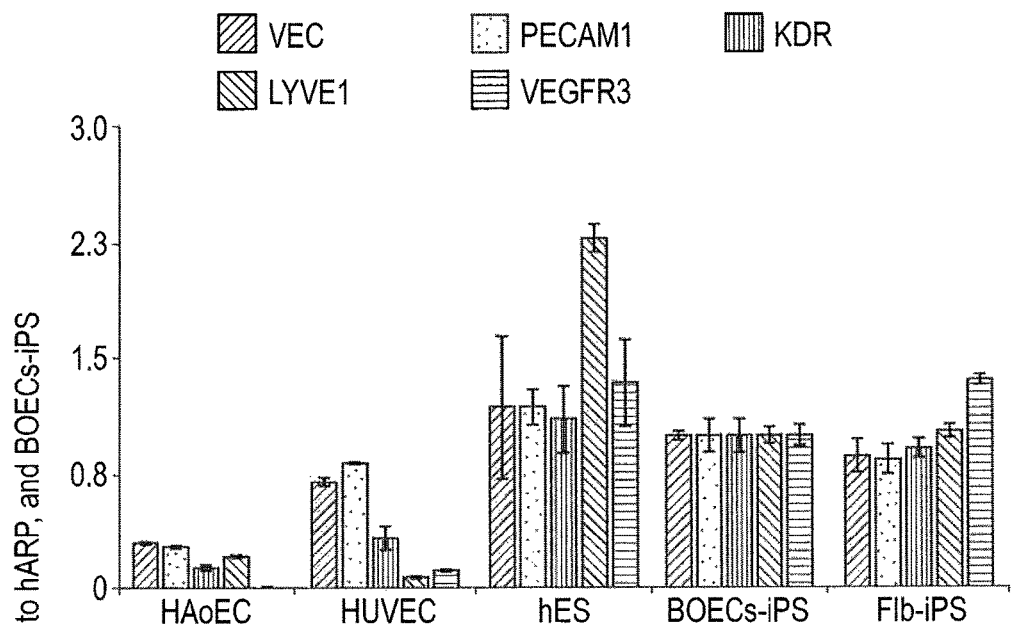
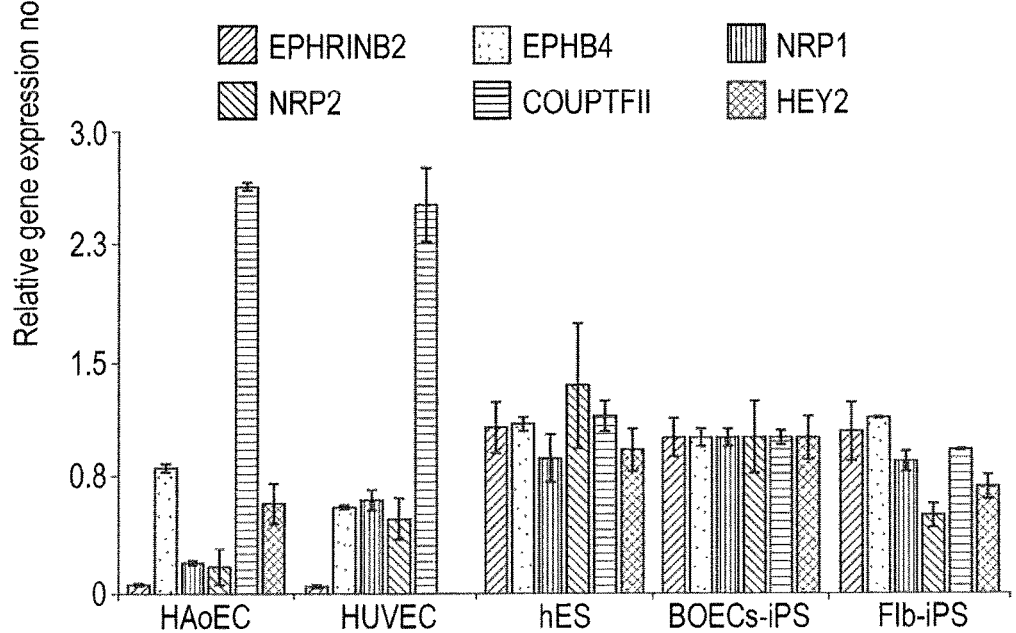

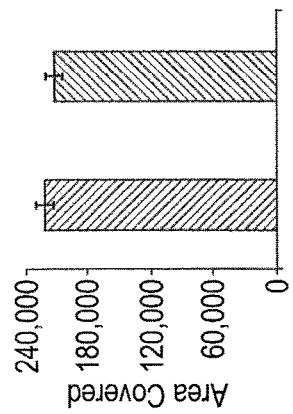
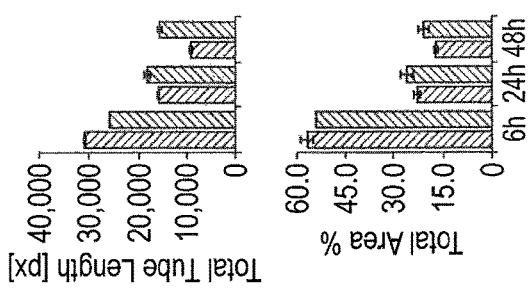
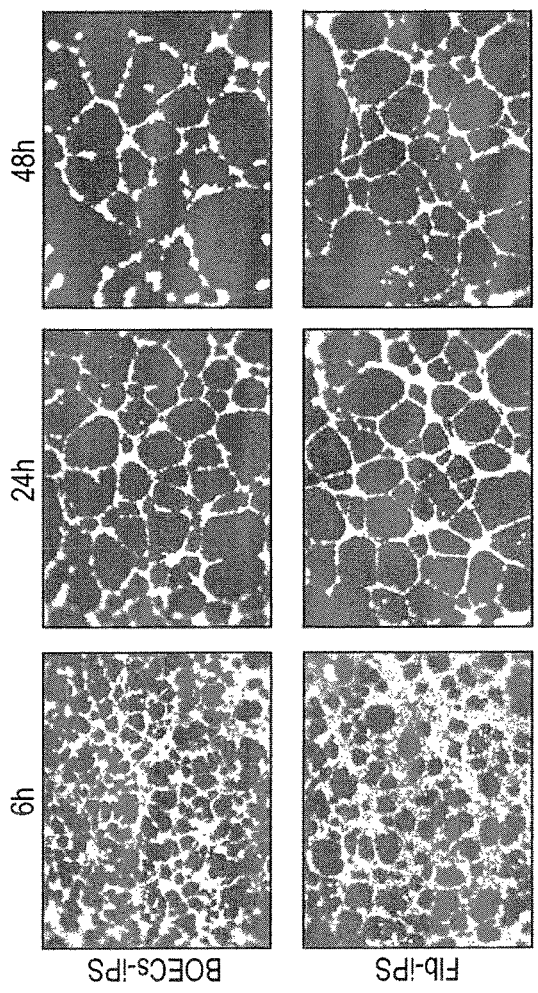
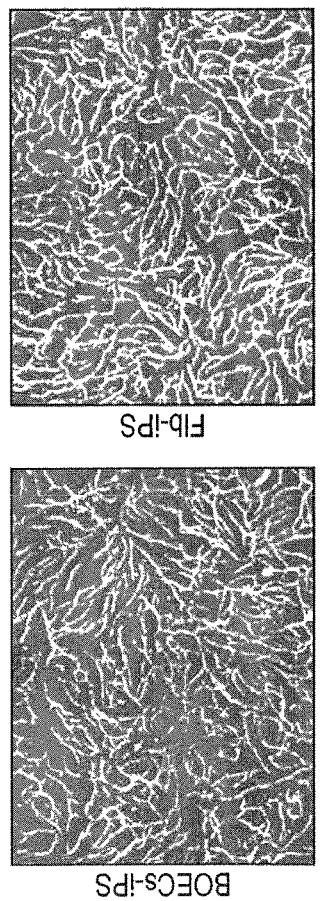

BOECs-iPS ECs

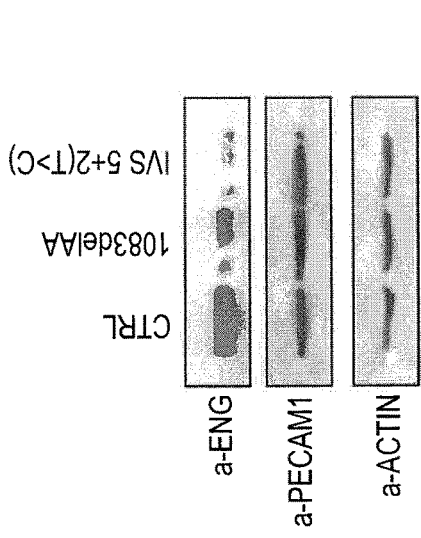
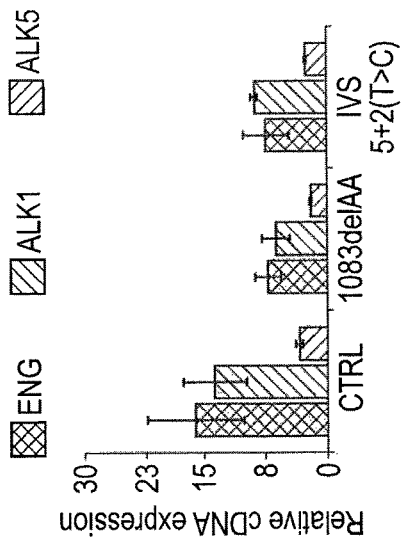
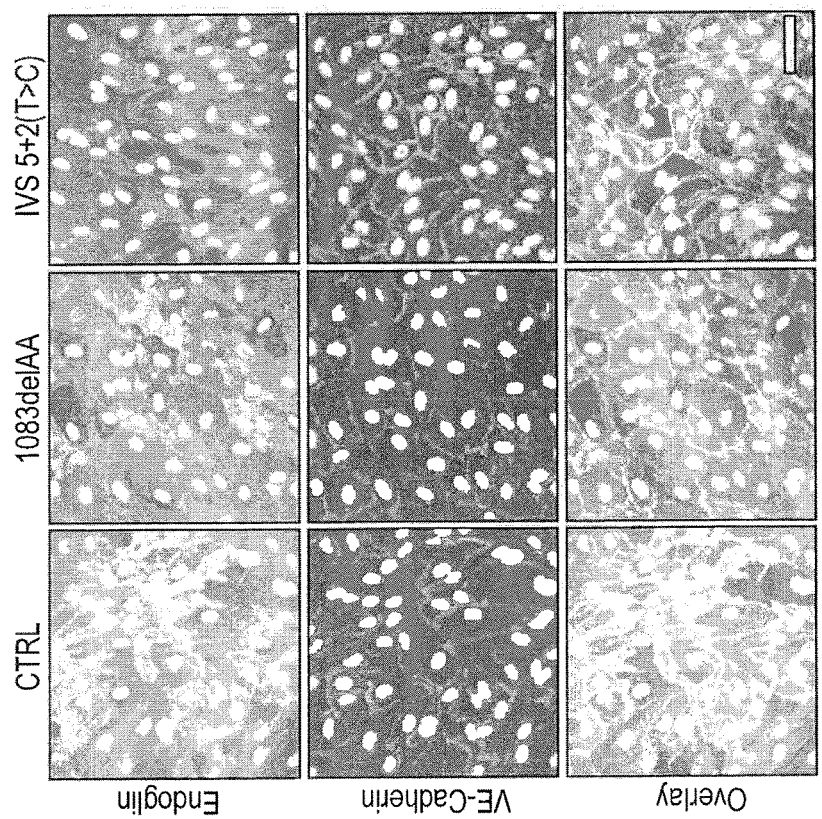

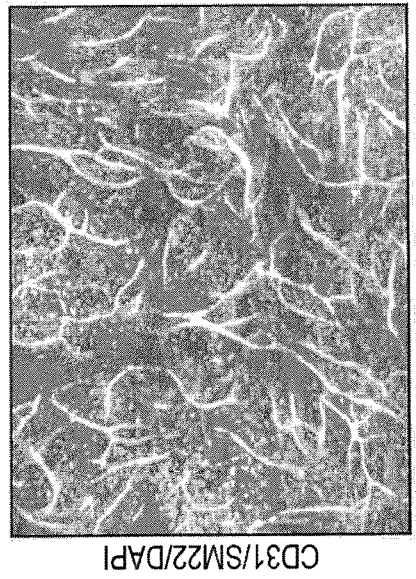
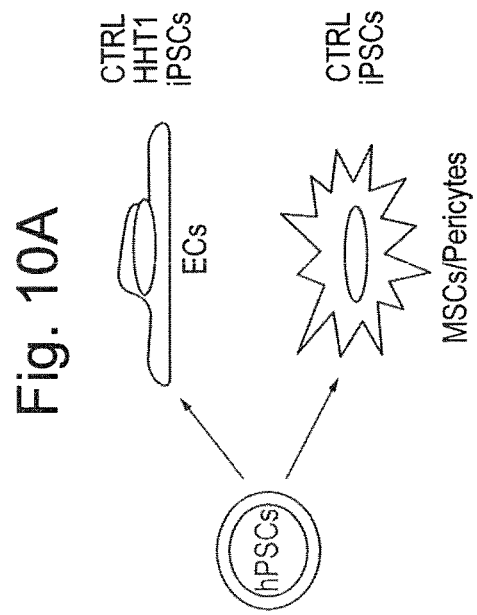
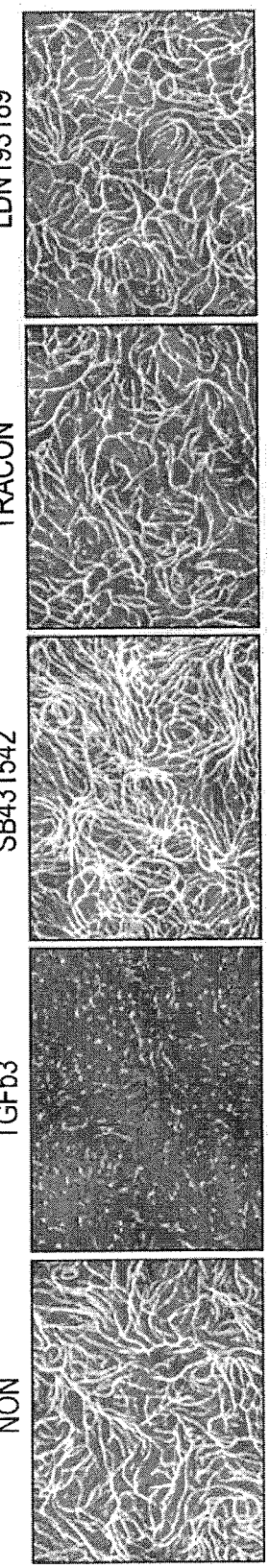

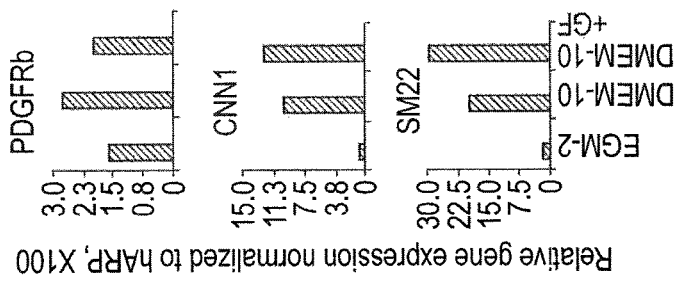
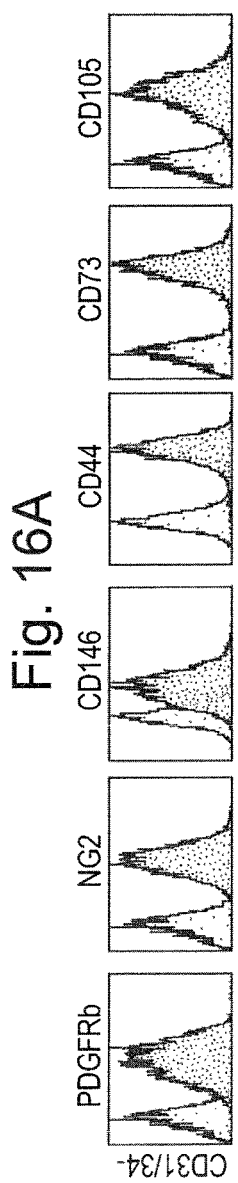
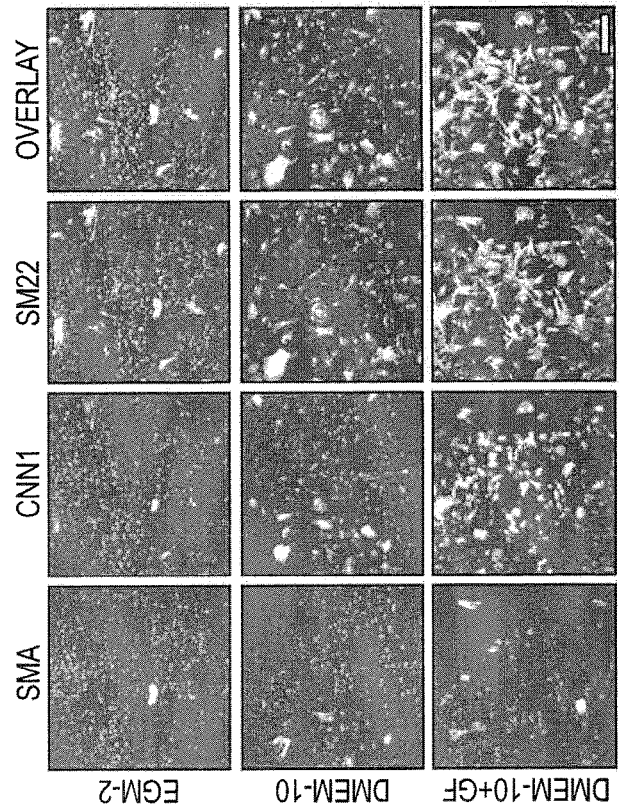

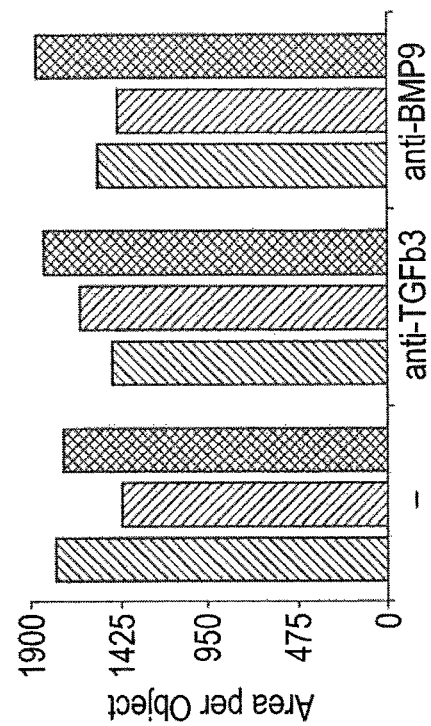
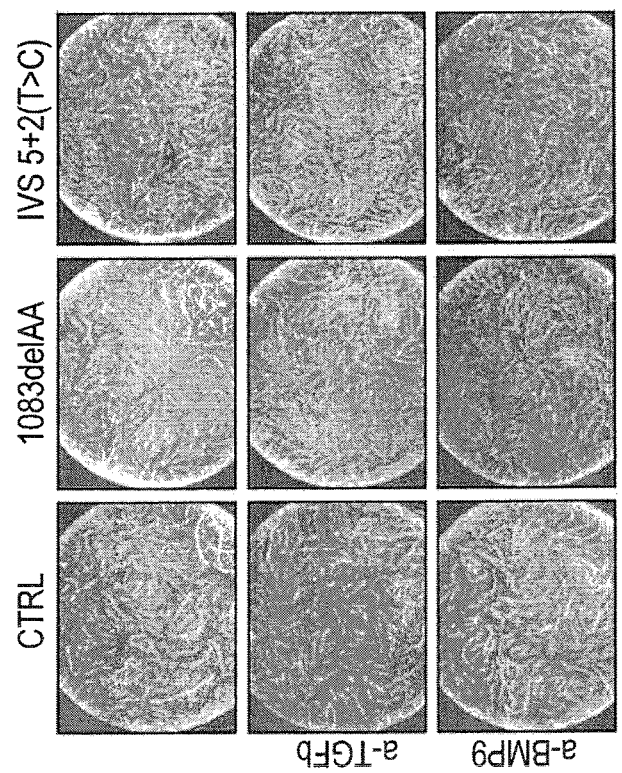
Fig. 17E
Fig. 17F

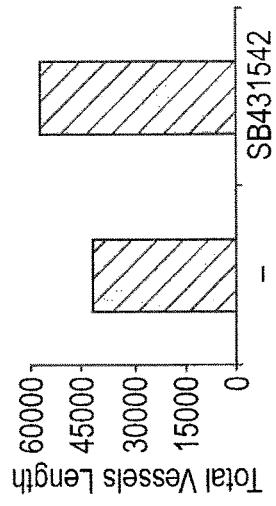
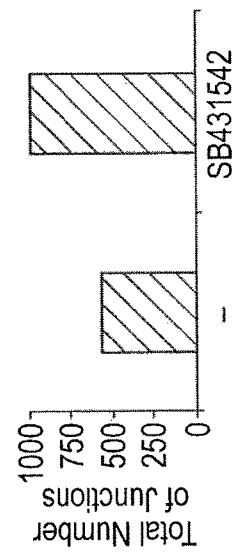
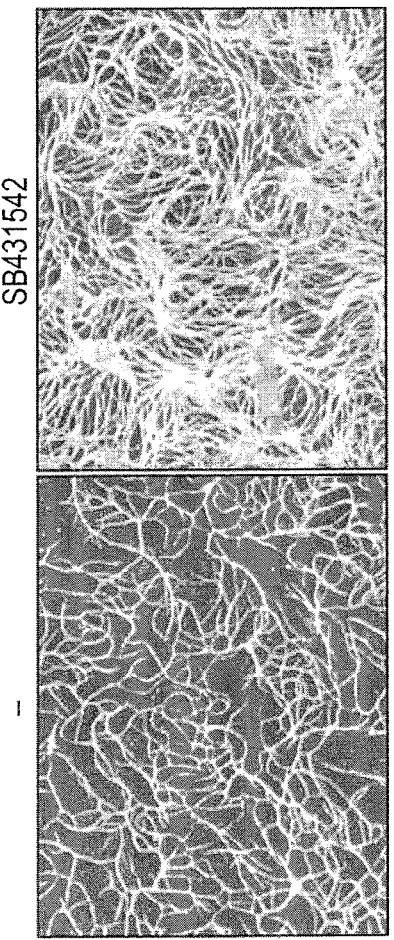
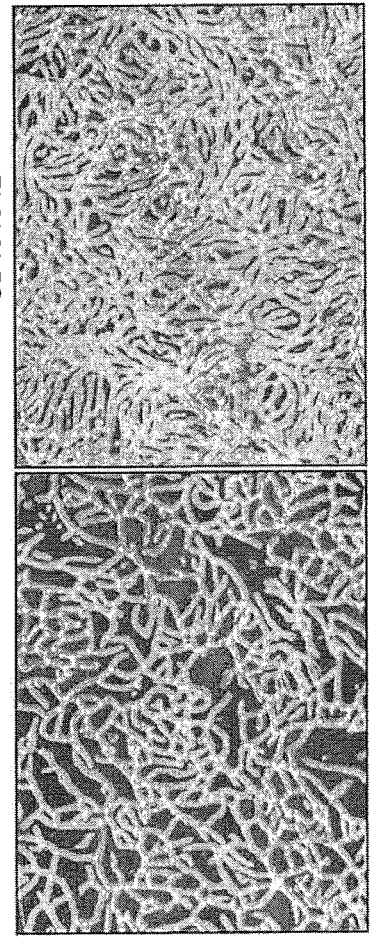

SEQUENCE LISTING

```
<160> NUMBER OF SEQ ID NOS: 48

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
caccattgaa atcctgagtg atgt                                              24

<210> SEQ ID NO 2
<211> LENGTH: 20
```

```
<212> TYPE: DNA
<213> ORGANISM: Artificial Sequence
<220> FEATURE:
<223> OTHER INFORMATION: primer

<400> SEQUENCE: 2
tgaccagccc aaaggagaag                                             20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
acgaccatct gccgctttg                                              19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcttcctcca cccacttctg                                             20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gccgaagaat agcaatggtg                                             20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tggtggtagg aagagtagag g                                           21

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
atcaccagcc actgcttc                                               18

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
```

```
gggttcctcc atcatctctt                                              20

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
ccatctcaat gtggtcaacc ttct                                         24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tcctcaggta agtggacagg tttc                                         24

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
attgcggaat aacatcggag                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gctcagccct gtgagaagac                                              20

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
cagctctcac cgtttgctc                                               19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aggaactgcc acagctgaat                                              20

<210> SEQ ID NO 15
<211> LENGTH: 21
<212> TYPE: DNA
<213> ORGANISM: Artificial Sequence
```

```
<220> FEATURE:
<223> OTHER INFORMATION: primer

<400> SEQUENCE: 15
ctggttccgg gagactgaga t                                              21

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
tgcgggaggt catgtctga                                                 19

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
gcatcgtggt caacataaca gaa                                            23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
gatggagcag gacaggttca g                                              21

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
cccgcaccga tccagaccac tcct                                           24

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
tgtcacccct gtcctctgcc tcac                                           24

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
acggagagtg tgaatgacca                                                20
```

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gatgcagctc agcaaattgt                                                 20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ctgctgagtg aaccacagga                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tcaggtcatg caactgaagc                                                 20

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
ccaggaaagg caaccttcaa c                                               21

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
acggaaacgg aaggtgtcc                                                  19

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ggcatcatca agcccatgaa                                                 20

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tcatgtatcg gaggtcgatg gt                                              22

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
cacaagggtg atccccataa                                                 20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gcctggtgtt gcttctcact                                                 20

<210> SEQ ID NO 31
<211> LENGTH: 17
<212> TYPE: DNA
<213> ORGANISM: Artificial Sequence
<220> FEATURE:
<223> OTHER INFORMATION: primer

<400> SEQUENCE: 31
ctgtgcctgc gactgtg                                                    17

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ggtgtcgatg acgtgtgact                                                 20

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
gaagtacgag ccccacaga                                                  19

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
cccaacgcag aaataaacg                                                  19

<210> SEQ ID NO 35

```
<211> LENGTH: 19
<212> TYPE: DNA
<213> ORGANISM: Artificial Sequence
<220> FEATURE:
<223> OTHER INFORMATION: primer

<400> SEQUENCE: 35
gaaaaggaag tgcccaaca                                                19

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
ctggcaaggg agtcacact                                                19

<210> SEQ ID NO 37
<211> LENGTH: 19
<212> TYPE: DNA
<213> ORGANISM: Artificial Sequence
<220> FEATURE:
<223> OTHER INFORMATION: primer

<400> SEQUENCE: 37
aacaccaacc ccacagatg                                                19

<210> SEQ ID NO 38
<211> LENGTH: 19
<212> TYPE: DNA
<213> ORGANISM: Artificial Sequence
<220> FEATURE:
<223> OTHER INFORMATION: primer

<400> SEQUENCE: 38
aagttgcagg cttgattcg                                                19

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ctggaagcag cattgtgtg                                                19

<210> SEQ ID NO 40
<211> LENGTH: 19
<212> TYPE: DNA
<213> ORGANISM: Artificial Sequence
<220> FEATURE:
<223> OTHER INFORMATION: primer

<400> SEQUENCE: 40
taactcgctg atggggaga                                                19

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
```

```
gctttccaca tgggctacat                                               20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
caagtggaga agctcaaggc                                               20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
tcatgaagtc catggcaaga                                               20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ttgtgccaac tgcttttgaa                                               20

<210> SEQ ID NO 45
<211> LENGTH: 21
<212> TYPE: DNA
<213> ORGANISM: Artificial Sequence
<220> FEATURE:
<223> OTHER INFORMATION: Fig. 6 control sequence

<400> SEQUENCE: 45
cttgatccag acaaagtgtg c                                             21

<210> SEQ ID NO 46
<211> LENGTH: 22
<212> TYPE: DNA
<213> ORGANISM: Artificial Sequence
<220> FEATURE:
<223> OTHER INFORMATION: Fig. 6 control sequence

<400> SEQUENCE: 46
cactcggccg ggtatggctc tc                                            22

<210> SEQ ID NO 47
<211> LENGTH: 21
<212> TYPE: DNA
<213> ORGANISM: Artificial Sequence
<220> FEATURE:
<223> OTHER INFORMATION: Fig. 6 1083delAA
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
```

```
<400> SEQUENCE: 47
cttgatccag acantgtgnn n                                              21

<210> SEQ ID NO 48
<211> LENGTH: 22
<212> TYPE: DNA
<213> ORGANISM: Artificial Sequence
<220> FEATURE:
<223> OTHER INFORMATION: Fig. 6 IVS 5+2(T>C)

<400> SEQUENCE: 48
cactcggccg ggyatggctc tc                                             22
```

DIFFERENTIATION AND EXPANSION OF ENDOTHELIAL CELLS FROM PLURIPOTENT STEM CELLS AND THE IN VITRO FORMATION OF VASCULATURE LIKE STRUCTURES

CROSS-REFERENCE TO RELATED APPLICATIONS

This application is a national phase entry under 35 U.S.C. § 371 of International Patent Application PCT/NL2014/050373, filed Jun. 10, 2014, designating the United States of America and published in English as International Patent Publication WO 2014/200340 A1 on Dec. 18, 2014, which claims the benefit under Article 8 of the Patent Cooperation Treaty and under 35 U.S.C. § 119(e) to Dutch Patent Application Serial No. 2010949, filed Jun. 10, 2013.

TECHNICAL FIELD

The disclosure relates to the field of cell biology and medicine. The disclosure, in particular, relates to means and methods for in vitro production of endothelial cells, pericytes, pericyte-derived smooth muscle cells and vasculature. The disclosure further relates to means and methods for screening compounds for their angiogenic or anti-angiogenic activity. Produced endothelial cells can be cultured and cryopreserved.

BACKGROUND

Pluripotent stem cells (PSCs) proliferate over long periods and can differentiate to many cell types of the body. Since they can be derived from humans (hPSCs) and indeed from any healthy individual or patient, they are becoming an increasingly important source of human cells for tissue engineering, modelling human disease, drug discovery and safety pharmacology. Efficient directed differentiation of hPSCs toward both vascular endothelial cells (ECs) and the adjacent mural cells (pericytes or mesenchymal stromal cells (MSCs) and vascular smooth muscle cells (vSMCs)) that provide vessels with stability, is however crucial for all of the above applications. Moreover, vascular differentiation of hPSCs could reveal early-unknown steps in endothelial specification during human development, and lead to better understanding of mechanisms that cause vascular defects and underlie different cardiovascular diseases. Understanding the underlying molecular signals driving differentiation and their timing is therefore important in a much broader context.

BRIEF SUMMARY

This disclosure provides improved protocols for differentiation of PSCs and particularly hPSCs toward EC lineages. The protocols are applicable to the majority, if not all hPSC lines. The protocols induce differentiation with equal efficiency in most, if not all hPSC lines. The protocols result in well-characterized, functional ECs that can be serially passaged and cryopreserved as an easily renewable EC source.

The protocol described herein preferably uses defined media and timed addition of growth factors to monolayer cultures and does not require an aggregation step (embryoid body formation), albeit that an aggregation step can be included. It results in very efficient generation of ECs from PSCs, from embryonic stem cells, preferably human embryonic stem cells (hESC) and induced pluripotent stem cells (iPSC). The source of cells for generating the iPSC and preferably human-induced pluripotent stem cells (hiPSCs) is not critical. In this disclosure, hiPSC were generated by skin biopsy fibroblasts (Fib) or blood outgrowth endothelial cells (BOECs). ECs from all hPSC types developed a remarkable degree of functionality, both in vitro and in vivo, despite relative immaturity, and performed significantly better in these functional assays than the more widely used human umbilical vein ECs (HUVECs) and, when combined with pericytes or pericyte-derived smooth muscle cells in vitro, provide much more robust and much longer lasting vascular or tubular networks. This disclosure further allows the capturing of disease phenotypes in the vascular system. The disclosure is particularly suited to capture vascular disease phenotypes resulting from specific gene mutations. The description further elaborates on Hereditary Hemorrhagic Telangiectasia (HHT) but is not limited to this disease. In fact many different diseases with a vascular phenotype can be used in this disclosure.

Hereditary hemorrhagic telangiectasia (HHT) is an inherited genetic disorder caused by autosomal dominant mutations in genes that mediate signaling by transforming growth factor β (TGFβ) and Bone morphogenetic protein (BMP), specifically Endoglin (ENG, HHT1), Activin receptor like kinase-1 (ALK-1, HHT2) and Smad4 (HHT3) in vascular endothelial cells (Begbie et al., 2003; Gallione et al., 2006; 2004; Letteboer, 2005; van den Driesche et al., 2003). HHT causes defects in blood vessels that make them prone to hemorrhage in the skin and mucous membranes, but also more severe abnormalities, such as arteriovenous malformations (AVMs) in the brain, lung, liver and gastrointestinal tract. These abnormalities, called telangiectases, consist of enlarged and dilated capillaries that lack the pericyte/smooth muscle cell coverage of normal vessels. AVMs essentially replace the entire capillary network, with the arterioles being connected directly to the venules (Guttmacher et al., 1995). To date no therapies have been developed that prevent the formation of these abnormalities in HHT patients or reverse them once they have occurred. At most, current therapies ameliorate symptoms of the disease, for example, by surgical intervention or cauterization of vessels, but are not cures (Shovlin, 2010). Medical treatments under investigation include anti-angiogenic drugs such as humanized an anti-VEGF antibody (bevacizumab) (Bose et al., 2009) and Thalidomide (Lebrin et al., 2010), but it is not yet clear how widely applicable these will be even if effective. Genetic models of HHT in mice have been established in which the affected genes were deleted but these have not shed much light on the specific genotype/phenotype relationships in human HHT patients (Arthur et al., 2000; Mahmoud et al., 2010; Srinivasan et al., 2003; Tang, 2003; Urness et al., 2000). Attempts to model HHT with the primary umbilical vein endothelial cells isolated from newborn patients failed to recapitulate the phenotype (Chan et al., 2004). Blood outgrowth endothelial cells (BOECs) or peripheral blood monocytes (PBMCs) from HHT patients could be alternative sources of cells to model HHT (Begbie et al., 2003; Fernandez-L et al., 2005; van Laake et al., 2006). However, the limited ability of both BOECs and PBMCs to expand in vitro makes them unsuitable as a renewable source of ECs for modelling the disease in humans and for drug discovery.

This disclosure provides an efficient and scalable system that recapitulates the formation of defective blood vessels in HHT patients. The system is based on cells that carry the underlying causal mutation. A good source for such cells is patient-derived cells that are induced into pluripotency, i.e., pluripotent stem cells (HHT-iPSCs). HHT-iPSCs potentially represent an unlimited source of vascular bed-specific ECs, pericytes and SMCs carrying the same genetic mutations as patients. In this disclosure, iPSC lines derived from HHT patients are provided that can be used to identify the mechanism underlying the predisposition toward development of disease and that can be used to model clinical features of HHT in vitro. The means and methods of the disclosure are very well suited to model defective endothelial-pericyte and defective endothelial-smooth muscle cells interactions.

This disclosure provides the derivation and endothelial differentiation of HHT1 disease iPSC (HHT1-iPSC) lines from patients harboring mutations in the ENG gene. ENG expression levels were significantly down-regulated in ECs from HHT1-iPSC after reprogramming, recapitulating our observation of reduced ENG expression in peripheral blood monocytes from HHT1 patients compared with healthy controls. Interestingly, despite reduced ENG expression levels HHT1 iPSC-derived ECs, they appeared to exhibit normal functional responses in standard angiogenesis assays in vitro and downstream signaling responses were similar to those in ECs from control iPSCs.

In this disclosure, ECs isolated from control and HHT1-iPSCs were co-cultured in monolayer with pericytes derived from the control line. Interestingly, it was found that BMP-9, an important ligand for signaling in ECs, caused specific inhibitory responses in ECs derived from HHT1-iPSCs but not those from control. The co-culture system thus revealed the disease phenotype whilst standard assays for vasculogenesis and angiogenesis in vitro had not. The disclosure can be used to find compounds that affect TGFβ ligand superfamily signaling during vasculogenesis and angiogenesis. The means and methods of the disclosure lead to a better understanding of the mechanisms underlying vascular diseases. The means and methods of the disclosure are particularly suited for high throughput screening (HTS) of compounds for their angiogenic or anti-angiogenic activity.

The disclosure provides an in vitro cell culture comprising endothelial cells and smooth muscle cells, wherein the endothelial cells are derived from in vitro differentiated pluripotent stem cells.

"Pluripotency" refers to a stem cell that has the potential to differentiate into all cells constituting one or more tissues or organs, for example, any of the three germ layers: endoderm (e.g., interior stomach lining, gastrointestinal tract, the lungs), mesoderm (e.g., muscle, bone, blood, urogenital tract), or ectoderm (e.g., epidermal tissues and nervous system). "Pluripotent stem cells" (or PSCs) used herein refer to cells that can differentiate into cells of any of the three germ layers, for example, descendants of totipotent cells, embryonic stem cells, or induced pluripotent stem cells. Pluripotent stem cells typically are positive in the "teratoma test" after injection into immunocompromised mice (Pera, 2008). Presently, an alternative is the so-called "Pluritest," in particular, for human pluripotent stem cells. In this test, cells or a cell line is expression profiled and the expression profile is compared to a set of expression profiles of defined cell lines (Müller et al., 2011). In this disclosure, it is preferred that the pluripotent stem cells are primate cells, and more preferably human cells. It is normally clear what a human cell is, however, with advances in nucleus and organel grafting techniques it is possible to generate chimeric cells. Such chimeric cells are considered human cells for the disclosure when they have a nucleus that is derived from a human cell, or are a cell division product that is ultimately derived from such a chimeric cell.

"Induced pluripotent stem cells," commonly abbreviated as iPS cells, iPSCs, or in case of human origin hiPS or hiPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting reprogramming factors (Yamanaka, 2009; 2012). The examples refer to several means and methods for producing induced pluripotent stem cells, however, various other methods are known to the person skilled in the art. In this disclosure, it is preferred that the pluripotent stem cells are iPS or iPSC cells, preferably hiPS or hiPSC cells. The hiPS or hiPSC are preferably obtained from skin biopsy fibroblasts or blood outgrowth endothelial cells.

Embryonic stem (ES) cells are pluripotent cells derived from the inner cell mass of a blastocyst. One way of isolating ES cells is by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated. The replating can be direct or on a feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2001). In other methods, mouse ES cells can be grown in serum-free medium in the presence of bone morphogenetic protein and LIF (Ying et al., 2003). Another method is the 2i or 2 inhibitor method also developed by A. Smith (Leitch et al., 2010).

Human ES cells can be obtained from blastocysts using previously described methods (Thomson and Marshall, 1998; Thomson et al., 1995; 1998; Reubinoff et al., 2000). In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e., exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human FS cells can be grown without a feeder cell layer by culturing the cells on a protein matrix such as MATRIGEL® or laminin in the presence of "conditioned" medium containing basic fibroblast growth factor (Xu et al., 2001). The medium is previously conditioned by co-culturing with fibroblasts. There are now a number of alternative methods that do not require conditioned medium. Whereas previously human embryos needed to be destroyed for the generation of pluripotent cell lines it is presently possible to generate these cells and cell lines using methods that do not require destruction of the donor embryo (Chung et al., 2008).

Methods for the isolation of rhesus monkey and common marmoset ES cells are also known (Thomson and Marshall, 1998; Thomson et al., 1995; 1998; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art and may be used with this disclosure, such as, e.g., those described in Yu and Thompson, 2008 (Yu and Thomson, 2008), which is incorporated herein by reference.

The source of ES cells for use in connection with the disclosure can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

"Embryonic stem (ES) cells" are pluripotent stem cells derived from early embryos.

Endothelial cells of this disclosure are typically vascular endothelial cells. They express the markers CD31 and VE-cadherin. Most though not necessarily all endothelial cells obtained via a method of the disclosure express CD34. The endothelial cells of this disclosure are derived from in vitro differentiated pluripotent stem cells. The in vitro differentiation is preferably done by means of a method as disclosed in the examples.

Microvascular perivascular cells ("pericytes") are defined by their location in vivo and the function in vitro. The pericyte is a small ovoid shaped cell with many finger-like projections that parallel the capillary axis and partially surround an endothelial cell in a microvessel. Pericytes share a common basement membrane with the endothelial cell. They are elongated cells with the power of contraction that have been observed to have a variety of functional characteristics. Pericytes are widely distributed in the body and include mesangial cells (in the glomeruli of the kidney), Rouget cells, or mural cells (in the retina of the eye) (Hirschi and D'Amore, 1996). Some of the pericyte functional characteristics observed in vivo and in vitro are that they regulate endothelial cell proliferation and differentiation, contract in a manner that either exacerbates or reduces endothelial cell junctional inflammatory leakage, synthesize and secrete a wide variety of vasoactive auto-regulating agonists, and synthesize and release structural constituents of the basement membrane and extracellular matrix (Shepro and Morel, 1993). Pericytes have thus been implicated as playing a role in vasoconstriction as well as a role in capillary blood flow, in the formation of blood vessels, in the immune response (particularly in the central nervous system), and in the extrinsic coagulation pathway. In the kidney, the contractile properties of the mesangial cells and their synthesis of various factors and structural proteins help to regulate the function of the glomerulus (Schlondorff, 1987).

Pericytes have been suggested to be derived from undifferentiated mesenchymal cells that are recruited by primordial endothelium and then differentiate into pericytes in microvessels or smooth muscle cells in large vessels. Pericytes are also progenitor cells and have been shown to differentiate into a variety of different cell types, including osteoblasts, chondrocytes, adipocytes, phagocytes, fibroblasts, and smooth muscle cells (Sims, 2000). Pericytes behave in a manner similar to osteoblasts in vitro, by forming a mineralized extracellular matrix and expressing a number of genes that are also expressed by osteoblasts. These cells also form a well-defined matrix of bone, cartilage, adipose and fibrous tissue in vivo (Doherty and Canfield, 1999; Hirschi and D'Amore, 1996).

Pericytes have been identified in the inner intima, the outer media, and in the vasa vasora of the adventitia of large, medium and small human arteries. Recent studies have suggested that pericytes in the arteries may be responsible, at least in part, for mediating the vascular calcification commonly associated with atherosclerosis (Canfield et al., 2000).

Various sources of pericytes have been identified. Suitable sources are, for instance, fat and bone marrow. One way of obtaining pericytes from these tissues is to collect the adherent cell fraction upon culture of the fat or the bone marrow. Upon-initiation of the in vitro cell cultures of the disclosure, pericytes can form smooth muscle cells. These smooth muscle cells contribute to the tubular network and the stability thereof rendering the network more stable than in comparable cultures but with, for instance, HUVEC instead of the endothelial cells of this disclosure. Smooth muscle cells derived from the pericytes can be marked with an SM22 binding antibody is indicated in the experimental section. Another marker for these smooth muscle cells is smooth muscle cell actin.

With the term "smooth muscle cell" as herein is meant the "vascular smooth muscle cell." Vascular smooth muscle refers to the particular type of smooth muscle found within, and composing the majority of the wall of blood vessels. Arteries have a great deal more smooth muscle within their walls than veins, thus their greater wall thickness. This is because they have to carry pumped blood away from the heart to all the organs and tissues that need the oxygenated blood. The endothelial lining of each is similar. Protocols for the identification of vascular smooth muscle cells are well established. Markers that can be monitored and selected for in vascular smooth muscle cells are smooth muscle cell-specific alpha-actin (alpha.SMA), calponin, smooth muscle myosin heavy chain (SM-MHC) and SM22. In this disclosure, it is preferred that the smooth muscle cells present in the in vitro culture of the disclosure are SM22 positive smooth muscle cells.

The disclosure further provides an in vitro cell culture comprising endothelial cells and smooth muscle cells, wherein the endothelial cells are capable of integrating into a vascular network in vivo. It was found that the endothelial cells of the disclosure are uniquely capable of integrating in the vasculature of an animal. In this disclosure, integration into zebrafish vasculature was shown. Other, preferably cultured endothelial cells typically do not integrate but rather are independent on the existing vasculature. This typically results in a clump of grafted cells at the injection site.

The disclosure further provides a method for producing an in vitro cell culture of the disclosure, the method comprising culturing endothelial cells and pericytes, wherein the endothelial cells are derived from in vitro differentiated pluripotent stem cell, the culturing allowing the differentiation of pericytes to smooth muscle cells. The method preferably further comprises adding a compound to the culture and determining whether the compound has an angiogenic or anti-angiogenic activity.

It is preferred that the smooth muscle cells are derived from pericytes. As indicated herein above, pericytes occur in many different tissue and organs and various sources of pericytes are available. It is preferred that the smooth muscle cells in the in vitro culture are derived from pericytes. Preferably the pericytes are seeded together with the endothelial cells and differentiate into the smooth muscle cells of the cultures of the disclosure. Various culture media are available for the cultures of the disclosure. A suitable culture medium is EGM-2 (Lonza), the cells are preferably seeded into dishes or well that have been coated with 0.1% gelatin (Crisan et al., 2008). The mentioned pericytes, smooth muscle cells or both are preferably derived from in vitro differentiated pluripotent stem cells. The yield and the stability of the tubular network is enhanced under these conditions. The endothelial cells, smooth muscle cells, pericytes or a combination thereof are preferably derived from iPS stem cells, preferably generated from skin biopsy fibroblasts or blood outgrowth endothelial cells.

The in vitro culture of this disclosure preferably comprises a tubular network. Without being bound by it, it is thought that the tubular network resembles an in vivo capillary network comprising the endothelial cells and the smooth muscle cells.

A unique feature of in vitro cell cultures of the disclosure is that unlike other culture systems, they do recapitulate a phenotype when the endothelial cells, the smooth muscle cells, the pericytes or a combination thereof are derived from an individual with a genetic defect that affects the vasculature. Since endothelial dysfunction has been linked to multiple genetic and non-genetic cardiovascular diseases, in vitro systems that (i) recapitulate disease phenotypes (ii) can be scaled up to produce multiple identical replicates and (iii) have an easily quantifiable readout of phenotype, are of great importance for drug and compound screening in the search for therapies. Thus, in a preferred embodiment of the disclosure, the endothelial cells comprise a genetic defect that in vivo exhibits a phenotype in vasculature. Preferably, the smooth muscle cells comprise a genetic defect that in vivo exhibits a phenotype in vasculature. Preferably, the pericytes comprise a genetic defect that in vivo exhibits a phenotype in vasculature.

The in vitro cell cultures of the disclosure can form stable vascular sprouts in vitro. The stability is apparent when such cultures are maintained for 3 or more preferably 4 or more, preferably 5, or more, preferably 7 days. In vitro cultures known in the art do not exhibit the stability obtained in this disclosure. The disclosure thus provides an in vitro culture of the culture that is maintained for 3 or more, preferably 4 or more, preferably 5, or more, preferably 7 or more days of culture. Cultures are typically though not necessarily not maintained longer than 15 days.

A suitable method for obtaining the cells with the genetic defect is by means of iPS from an individual afflicted with the genetic defect. In a preferred embodiment, the genetic defect is a genetic defect that results in fragile blood vessel formation. The fragile blood vessel formation is preferably the result of defective or inefficient endothelial cells/pericyte interaction or endothelial cell/smooth muscle cell interaction. Examples of mutations underlying the genetic defect are inactivating mutations in ENG, ALK1, SMAD4, NOTCH3, KRIT1, PDCD10, CCM2 and/or BMPPRII. The individual afflicted with the genetic defect is preferably suffering from HHT (hereditary hemorrhagic telangiectasia), CADASIL (cerebral autosomal dominant arteriopathy with subcortical infarcts and leukoencephalopathy), CCMs (Cerebral Cavernous Malformations) or PAH (pulmonary arterial hypertension). The individual afflicted with the genetic defect is preferably an individual with a predisposition toward disease associated with endothelial dysfunction (diabetes, inflammatory responses) and pathological/excessive angiogenesis (such as in tumors). When the genetic defect is known, the cells do not have to be derived from an individual with the genetic defect. Instead, the cells can be provided with the genetic defect in vitro.

An in vitro culture of the disclosure preferably comprises endothelial cells as mentioned herein, smooth muscle cells as mentioned herein and pericytes as mentioned herein.

The disclosure further provides a method for producing a cell culture of the disclosure comprising:
(a) culturing pluripotent stem cells in defined medium containing ActivinA, BMP4, VEGF, preferably VEGF165, and a canonical WNT ligand or GSK3 inhibitor, preferably CHIR992021, to produce a culture comprising differentiated cells;
(b) culturing the cells obtained in step (a) in defined medium containing VEGF, preferably VEGF165, and a TGF {beta} signaling inhibitor, preferably SB43152, to produce endothelial cells.

The pluripotent stem cells are preferably iPSC. The method yields a high number of endothelial cells. The method yields cells of which a high percentage are endothelial cells. Endothelial cells produced by a method of the disclosure can be purified were purified with CD31 coupled magnetic beads (Life Technologies) and culture further scaled up on 1% gelatin coated tissue culture flasks in human endothelial serum free media (EC-SFM) (Life Technologies) with additional VEGF (30 ng/ml), bFGF (20 ng/ml, R&D) and platelet low bovine extract (1%, BIT). ECs were routinely maintained up to passage 5, and functional assays were performed on cell between passages 2-3.

The method preferably further comprises collecting the cells produced in step (b) and obtaining therefrom a collection of cells that comprises more than 90% endothelial cells, preferably based on the expression of CD31, CD34 or VE-Cadherin. Such collections are typically obtained by separating the endothelial cells from other cells in the culture. Such separation can be done in a number of ways such as FACS cell sorting, cell panning by means of binding molecules that specifically recognize an endothelial cell marker on the surface of the cells. For this disclosure, it is preferred that the collection of endothelial cells is obtained by means of bead separation. In a preferred embodiment, the collection of cells is obtained by separating the cells of step (b) on the basis of CD31 expression, preferably by means of beads comprising a CD31 binding antibody. Preferably the collected cells also express VE-Cadherin. Preferably the collected cells also express CD34. The expression of the markers can be warranted by using the markers in the cell selection process. In a preferred embodiment, the collection of cells express CD31, CD34 and VE-Cadherin. The fractionation is preferably done on the basis of the two or more of the markers CD34, CD31, KDR, CD73, VE-Cadherin, and PDGFRb. In a preferred embodiment, the fractionation is done on the basis of three or more, preferably four or more, preferably five or more and most preferably all six of the markers. In a preferred embodiment, the (collection of) endothelial cells are CD34+, CD31+, KDR+, CD73+, VE-Cadherin+, and/or PDGFRb− (with + meaning positive for the marker and − meaning negative for the marker; with the exception of the − in VE-Cadherin the name of a molecule). The endothelial cells obtained via a method of the disclosure are particularly suited for further culture in an in vitro culture of the disclosure. Such a collection is suited for the further culture in an in vitro culture of the disclosure. The collection of endothelial cells that is obtained can be cultured further in defined medium for a number of passages. A preferred method and a preferred medium with preferred supplements and factors are indicated in the example section. Alternative media are available to the skilled person, for example, APEL medium (Stem Cell Technologies). The collection of cells or the further cultured cells can be frozen and stored without essentially losing the unique properties as disclosed herein. This favorable feature allows for efficient standardization and up scaling. This allows the use of high throughput screening of compounds and conditions for compounds and conditions that have angiogenic or anti-angiogenic activity. To this end, a method of the disclosure preferably further comprises providing the endothelial cells with a cell storage medium and storing the endothelial cells at a temperature of −70° C. or less. In a preferred embodiment, the method further comprises retrieving the frozen cells from storage, thawing them and culturing the endothelial cells. A method of the disclosure preferably further comprises culturing the endothelial cells together with smooth muscle cells as defined elsewhere herein. The smooth muscle cells are preferably the smooth muscle cells as indicated as preferred elsewhere herein.

The disclosure further provides a method for producing a cell culture of the disclosure comprising:
  (a) culturing pluripotent stem cells in defined medium containing ActivinA, BMP4, VEGF, preferably VEGF165, and a canonical WNT ligand or GSK3 inhibitor, preferably CHIR992021, to produce a culture comprising differentiated cells;
  (b) culturing the cells obtained in step (a) in defined medium containing VEGF, preferably VEGF165, and a TGF{beta} signaling inhibitor, preferably SB43152, to produce pericytes.

The method preferably further comprises collecting the cells produced in step (b) and obtaining therefrom a collection of cells that comprises more than 90% pericytes, preferably based on the expression of CD31. Preferably, the CD31 negative fraction is collected. These cells are typically negative for CD34 and VE-Cadherin. Such collections are typically obtained by separating the pericytes from other cells in the culture. Such separation can be done in a number of ways such as FACS cell sorting, cell panning by means of binding molecules that specifically recognize an endothelial cell marker on the surface of the cells. For this disclosure, it is preferred that the collection of pericytes is obtained by means of bead separation. In a preferred embodiment, the collection of cells is obtained by separating the cells of step (b) on the hack of CD31 expression, preferably by means of heads comprising a CD31 binding antibody. Preferably, the collected cells are negative for CD31. The cells are preferably also negative for VE-Cadherin. Preferably, the collected cells are negative for CD34. The expression of the markers can be warranted by using the markers in the cell selection process. In a preferred embodiment, the collection of pericytes is selected on the basis that the cells do not express CD31, CD34 and VE-Cadherin.

The fractionation is preferably done on the basis of the two or more of the markers CD34, CD31, KDR, CD73, VE-Cadherin, and PDGFRb. In a preferred embodiment, the fractionation is done on the basis of three or more, preferably four or more, preferably five or more and most preferably all six of the markers. In a preferred embodiment, the pericytes are CD34−, CD31−, KDR−, CD73−, VE-Cadherin−, and/or PDGFRb+ (with + meaning positive for the marker and − meaning negative for the marker).

iPSC-derived pericytes/mesenchymal cells derived from the CD31-fraction emerging during the endothelial differentiation protocol can be further cultured for scaling. For instance, CD31-cells can be plated on gelatin coated plates in EGM-2 media (Lonza). After 4 days medium can be replaced by DMEM+10% FBS supplemented with TGFβ3 (2 ng/ml, Peprotech) and PDGF-BB (4 ng/ml, Peprotech). iPSC-derived pericytes can be routinely maintained on gelatin-coated plates in DMEM+10% FBS.

The pericytes obtained via a method of the disclosure are particularly suited for further culture in an in vitro culture of the disclosure. Such a collection is suited for the further culture in an in vitro culture of the disclosure. The (collection of) pericytes that is obtained can be cultured further in defined medium for a number of passages. A preferred method and a preferred medium with preferred supplements and factors is indicated in the example section. Alternative media are available to the skilled person, for example, APEL medium (Stem Cell Technologies). The collection of cells or the further cultured cells can be frozen and stored without essentially losing the unique properties as disclosed herein. This favorable feature allows for efficient standardization and up scaling. This allows the use of high throughput screening of compounds. To this end a method of the disclosure preferably further comprises providing the pericytes with a cell storage medium and storing the pericytes at a temperature of −70° C. or less. In a preferred embodiment, the method further comprises retrieving the frozen cells from storage, thawing them and culturing the pericytes cells. A method of the disclosure preferably further comprises culturing the pericytes together with endothelial cells as defined elsewhere herein. The endothelial cells are preferably the endothelial cells as indicated as preferred elsewhere herein.

The disclosure further provides a collection of cells obtainable by a method according to the disclosure in a cell storage container that is maintained at a temperature of −70° C. or less. The frozen cell collection preferably comprises more than 90% endothelial cells. The disclosure, therefore, further provides a kit of parts comprising a cell storage container comprising endothelial cells obtained by a method of the disclosure and a cell container comprising pericytes obtained via a method of the disclosure. The kit is preferably maintained at a temperature of 70° C. or less until use for culturing.

Further provided is an in vitro cell culture comprising endothelial cells and smooth muscle cells, wherein the endothelial cells are derived from in vitro differentiated pluripotent stem cells wherein the endothelial cells are obtained by
  (a) culturing pluripotent stem cells in defined medium containing ActivinA, BMP4, VEGF, preferably VEGF165, and a canonical WNT ligand or GSK3 inhibitor, preferably CHIR992021, to produce a culture comprising differentiated cells;
  (b) culturing the cells obtained in step (a) in defined medium containing VEGF, preferably VEGF165, and a TGF {beta} signaling inhibitor, preferably SB43152, to produce endothelial cells.

The smooth muscle cells are preferably obtained by
  (a) culturing pluripotent stem cells in defined medium containing ActivinA, BMP4, VEGF, preferably VEGF165, and a canonical WNT ligand or GSK3 inhibitor, preferably CHIR992021, to produce a culture comprising differentiated cells;
  (b) culturing the cells obtained in step (a) in defined medium containing VEGF, preferably VEGF165, and a TGF {beta} signaling inhibitor, preferably SB43152, to produce pericytes.

The methods preferably further comprises collecting the cells produced in step (b) and obtaining therefrom a collection of cells that comprises more than 90% endothelial cells, preferably based on the expression of CD31, CD34 or VE-Cadherin. The collection of cells is preferably obtained by separating the cells of step (b) on the basis of CD31 expression, preferably by means of beads comprising a CD31 binding antibody. The endothelial cells may be provided with a cell storage medium and be stored at a temperature of −70° C. or less prior to initiating the in vitro cell culture. The endothelial cells are preferably capable of integrating into a vascular network in vivo, collecting the cells produced in step (b) and obtaining therefrom a collection of cells that comprises more than 90% endothelial cells, preferably based on the expression of CD31, CD34 or VE-Cadherin. The collection of cells is preferably obtained by separating the cells of step (b) on the basis of CD31 expression, preferably by means of beads comprising a CD31 binding antibody. The methods preferably further comprises collecting the cells produced in step (b) and obtaining therefrom a collection of cells that comprises more than 90% pericytes, preferably based on the expression of CD31, CD34 or VE-Cadherin. The collection of cells is preferably obtained by separating the cells of step (b) on the basis of CD31 expression, preferably by means of beads comprising a CD31 binding antibody. The pericytes may be provided with a cell storage medium and be stored at a temperature of −70° C. or less prior to initiating the in vitro cell culture. The smooth muscle cells are preferably derived from in vitro differentiated pluripotent stem cells, or derived from pericytes, preferably the smooth muscle cells are derived from pericytes that are derived from in vitro differentiated pluripotent stem cells. Preferably, the endothelial cells, the smooth muscle cells, or both, are derived from iPS stem cells, preferably generated from skin biopsy fibroblasts or blood outgrowth endothelial cells. The in vitro cell culture preferably comprises a capillary network comprising the endothelial cells and the smooth muscle cells. The endothelial cells preferably comprise a genetic defect that in vivo exhibits a phenotype in vasculature. The smooth muscle cells preferably comprise a genetic defect that in vivo exhibits a phenotype in vasculature. The pericytes of the disclosure can acquire the expression of contractile smooth muscle cells such as SM22 and caldesmon upon co-culture with endothelial cells obtained by a culture method of the disclosure, or by stimulation with TGF-beta.

The endothelial cells in an in vitro cell culture of the disclosure comprising endothelial cells and smooth muscle cells are preferably obtained by a culture method of the disclosure. The endothelial cells are preferable CD34+, CD31+, KDR+, CD73+, VE-Cadherin+, and/or PDGFRb−. In a preferred embodiment, the endothelial cells are CD34+, CD31+, KDR+, CD73+, VE-Cadherin+ and PDGFRb−.

The smooth muscle cells in an in vitro cell culture of the disclosure comprising endothelial cells and smooth muscle cells are preferably obtained by a culture method that produces pericytes according to the disclosure. The pericytes are preferably CD34−, CD31−, KDR−, CD73−, VE-Cadherin−, and/or PDGFRb+. In a preferred embodiment, the pericytes are CD34−, CD31−, KDR−, CD73−, VE-Cadherin− and PDGFRb+.

Although functionally very similar, it is known that pluripotent stem cells differ from iPSC in various ways. For review see Liang and Zhang (2013) Cell Stem Cell 13: 149-159). At least some of these differences are maintained upon differentiation of the stem cells. For instance, methylome profiling has shown that there exist DMRs differences between hESCs and hiPSCs. The MDR differences between hESCs and hiPSCs can be detected in both CG dinucleotides and non-CG sites (see Liang and Zhang: 2013). Differentially methylated regions (DMRs), are genomic regions with different methylation statuses among different samples. Functional roles for the presence of DMRs between hESC and hiPSC can be functional regions involved in gene transcriptional regulation. DMRs are thought to result from epigenetic differences among the cells. Many DMRs have been found in the development stages and in the reprogrammed progress. For each iPSC cell line, a cell-line-specific methylation pattern has been widely reported. Thus there are various ways in which the source of the stem cells used to produce the in vitro cultures of the disclosure can be determined. The produced in vitro cultures maintain this property and can thus also be distinguished from cultures produced from cells of a different origin.

The disclosure further provides an in vitro cell culture assay comprising endothelial cells and smooth muscle cells according to the disclosure for use in screening for angiogenic and anti-angiogenic compounds. Also provided is the use of an in vitro cell culture according to the disclosure for determining angiogenic activity of a compound, preferably wherein the endothelial cells and/or the smooth muscle cells, comprise a genetic defect that in vivo exhibits a phenotype in vasculature. These use are preferably performed in a high throughput setting.

BRIEF DESCRIPTION OF THE DRAWINGS

FIG. 1A, Flow cytometric analysis of KDR and CD34 expression at differentiation day 10. hPSCs (BOECs-iPS) were induced to differentiate upon sequential application of the cocktail of growth factors at day 0-3 consisting of either BMP4, VEGF and CHIR (RVC) or BMP4, VEGF, ActA and CHIR (BVAC); at day 3 differentiation the media was replaced with VEGF only, or VEGF together with SB (SB-431542) (5 μM). FIG. 1B, Relative gene expression profiling of differentiation stage-specific genes at different time points of differentiation examined in hES, BOECs-iPS and Fib-iPS at day 1 (d1), day 4 (d4) and day 10 (d10).

FIG. 2A, Flow cytometric analysis of CD31 and PDGFRb expression at differentiation day 10 in three independent hPSC lines (hES, BOECs-iPS and Fib-iPS). FIGS. 2B and 2C. Average percentages of CD31+/CD34+ and PDGFRb+ cells in several independent differentiations at day 10 (hES, Fib-iPS N=3; BOECs-iPS N=6). Data represents as mean±standard deviation. FIG. 2D, Flow cytometric analysis of CD31+/CD34+ and CD31−/CD34− populations for surface expression of VE-Cadherin (VEC), KDR, CD73, CD105 and PDGFRb.

FIGS. 3A-3C: Expansion of endothelial cells from hPSCs. FIG. 3A, Flow cytometric analysis of isolated and expanded CD31+ from hPSCs. Representative FACs plots for relative expression levels of CD31, CD34, VE-Cadherin, KDR, CD73 and CD105. FIG. 3B, Confocal immunofluorescence analysis of the expression endothelial-specific markers VE-Cadherin, CD31, and vWF. FIG. 3C, Expression profiling of endothelial-specific, arterial, venous, and lymphatic genes in endothelial cells derived from hPSCs. The data was normalized to relative expression levels in HUVAC, and HAOEC.

FIGS. 4A-4D: Functional characterization of hPSC-derived endothelial cells. FIG. 4A, Representative immunofluorescent images of the PKH-67 labelled endothelial cells derived from hPSCs upon seeding on MATRIGEL® basement membrane matrix. The images were taken with the BD Pathway imaging system 4× objective in the 2×2 montage mode. FIG. 4B, Wimasis quantification of total sprouts length and total number of branching points. FIG. 4C, Capillary-like network formation in 2D co-culture system of hPSC-derived endothelial cells and pericytes. FIG. 4D, Total tube are quantification.

FIG. 6A, Characterization of ENG mutations in HHT1 patient-derived iPSCs: ENG genomic map, location of the mutations, protein map. FIG. 6B, Sequencing of the genomic DNA from HHT1 iPSCs to confirm mutations (SEQ ID NOS:45-48). FIG. 6C, Characterization of HHT1 iPSCs lines: immunofluorescent images for Oct3/4, TRA-1-81, SSEA4 and Nanog. Scale bar 75 µm. FIG. 6D, Pluritest. FIG. 6E, Immunofluorescent images of the spontaneous differentiation demonstrating derivatives of all three germ layers: bIII-tubulin for neuroectoderm, AFP for endoderm and SMA for mesoderm. Scale bar 75 µm.

FIG. 7A, Flow cytometry analysis of CD34 and CD31 expression at differentiation day 10 in control and HHT1 patient-specific iPSCs. FIG. 7B, Flow cytometry analysis of CD105 and VE-Cadherin expression at differentiation day 10 in control and HHT1 patient-specific iPSCs. FIG. 7C, Quantification of the yield of CD31+/CD34+ endothelial cells at day 10 of differentiation from several independent experiments (N=6). FIG. 7D, Flow cytometry analysis of the surface expression levels on CD31/CD34+ endothelial cells for ENG (CD105), CD31, CD34 and KDR. Mean fluorescence intensity for HHT1 lines were normalized to the control. Average values of several independent differentiations are shown (N=9). *p<0.001 (ANOVA, Scheffe).

FIGS. 8A-8G: Characterization of ENG expression on isolated and expanded HHT1 iPSC-derived endothelial cells (CD31+). FIG. 8A, Flow cytometry analysis of isolated endothelial cells from control and HHT1 patient-specific iPSCs. The purity was determined based on the % of CD31/CD34+ cells. Note >95% purity for endothelial cell isolated from iPSC lines. FIG. 8B, Relative surface expression levels of CD31, CD34, VE-Cadherin and KDR on isolated endothelial cells derive from control and HHT1 patient-specific iPSC lines. FIGS. 8C and 8D, Flow cytometry analysis of CD105 (ENG) expression on isolated ECs. Clear reduction is observed for 1083delAA and IVS 5+2 (T>C) mutant. FIG. 8E, Immunofluorescent staining for ENG and VE-Cadherin of ECs isolated from control and HHT1 patients. Scale bar 100 µm. FIG. 8F, Western blot analysis of ENG protein expression levels in ECs isolated from control and HHT1 patients. Blots were probed with antibodies against PECAM1, ENG and ACTIN. FIG. 8G, Analysis of ENG cDNA expression levels in endothelial cells isolated from HHT1-iPSC lines. Relative expression of ENG, ALK1 and ALK5 cDNA in ECs from control and patient-specific iPSCs.

FIG. 9A, MATRIGEL® tube formation assay. ECs isolated from control and HHT1-iPSCs were pre-labelled with PKF67 general cytoplasmic membrane labelling dye. Images were acquired at 24 hours with the 4× objective in 2×2 montage mode (BD Pathway855). FIG. 9B, Wimasis quantification of total area and total tube length covered. Total are, tube length and total branching points were quantified with Wimasis software. Plots represent an average of 4 (N=4) independent experiments. Bars are STDEV of mean. FIG. 9C, Cell proliferation. Control and HHT1-iPSC-derived ECs were seeded into 96-well plates (2,000 cells/well). Next day medium was replaced with serum-free or complete growth medium. Relative cell number was determined in MTS-based assay at 72 hours after media change.

FIGS. 10A-10E: Two-dimensional co-culture system comprising of hPSC-derived ECs co-cultured with iPSC-derived mural cells. FIG. 10A, Schematic overview of 2D co-culture system comprising control and HHT1-iPSC-derived ECs and control iPSC-derived mural cells/pericytes. FIG. 10B, Immunofluorescent staining of the co-culture at day 7 with endothelial-specific marker (CD31) in green, and smooth muscle marker SM22 (in red), samples were counterstained with DAPI (in blue). Images were acquired with 10× objective in 3×3 montage mode (BD Pathway855). FIG. 10C, Representative images of the endothelial network counterstained with anti-CD31 (in white). Images were acquired with 4× objective 2×2 montage mode (BD Pathway855). FIG. 10D, Quantification of the total area covered by endothelial sprouts. Average values from 4 independent wells, bars are STDEV of mean. FIG. 10E, Well-to-well variation in the assay. Measurements from independent were plotted to demonstrate low well-to-well variation. Z-factor was determined (Z=0.493>0.4) based on the TGFβ3 condition was taken as a minimum and the SB condition as a maximum.

FIG. 11A, Representative images of endothelial sprouts at day 7 of the assay stained with anti-CD31 antibody (in white). ECs were derived from control and HHT1-iPSCs. Administration of TGFβ3 (1 ng/ml) inhibits sprout formation in all lines. However, BMP9 (1 ng/ml) induced a selective inhibitory effect in HHT1-iPSC-derived ECs only. FIG. 11B, Quantification of total area per endothelial cell sprout (object). Data represents 4 independent experiments (N=4). Bars represents SEM. One-way ANOVA (LDS post-hoc) was performed to calculate significance.

FIG. 12A, Representative immunofluorescent images of the day 7 co-culture. Samples were counterstained with endothelial-specific anti-CD31 (in green), smooth muscle-specific anti-SM22 (in red), and nuclei were visualized with DAPI (in blue). Scale bar 200 µm. FIG. 12B, Representative images of SM22 positive smooth muscle cells (in white) were acquired with 10× objective 3×3 montage mode (BD Pathway855). FIG. 12C, Quantification of median fluorescence intensity for SM22. Bars represent STDEV of mean.

FIG. 15A, Gating strategy to identify monocyte subset based on FSC and SSC scatters. Back gating of CD14+ monocytes to confirm the cell size of the population. FIG. 15B, Representative CD105 histograms to demonstrate reduced CD105 expression levels in HHT1 monocytes (light red) compared to control (dark grey). Isotype control is shown in light grey. FIG. 15C, Quantification of the mean fluorescence intensity (MFI) of CD105 expression levels in HHT1 and control PBMCs. Bars are STDEV of mean of three independent measurements.

FIGS. 16A-16C: Characterization of mesenchymal cells from iPSCs. FIG. 16A, Flow cytometry analysis for expression pericyte/MSC markers PDGFRb, NG2, CD146, CD44, CD73, CD105 in CD31/CD34-iPSC-derived cells. FIG. 16B, Immunofluorescent staining for the expression of contractile smooth muscle cell markers: SMA, SM22, CNN1 in mesenchymal cell grown in basal EGM-2, DMEM 10% FSB or DMEM 10% FBS with extra supplementation with PDGF-BB and TGFβ3 for 4 days. Scale bar 250 µm. FIG. 16C, Representative real time PCR analysis for the expression of relative levels for PDGFRb, CNN1 and SM22 in iPSC-derived mesenchymal cells grown in the same conditions as described above.

FIGS. 17A-17F: Defective endothelial-pericyte interactions in HHT1 patient-derived ECs. FIG. 17A, Endothelial sprout formation of control and HHT1-iPSC-derived endothelial cells at day 7 with and without extra supplementation with ALK5 inhibitor (SB431542). FIG. 17B, Endothelial sprout formation of control and HHT1-iPSC-derived endothelial cells at day 7 with extra supplementation with TGFβ3 (1 ng/ml) with and without ALK5 inhibitor (SB431542). FIG. 17C, Endothelial sprout formation of control and HHT1-iPSC-derived endothelial cells at day 7 with extra supplementation with BMP9 (1 ng/ml) with and without ALK5 inhibitor (SB431542). FIG. 17D, Quantification of relative sprout length per object. FIG. 17E, Endothelial sprout formation of control and HHT1-iPSC-derived endothelial cells at day 7 with extra supplementation with anti-TGFβ3 neutralizing antibodies (40 µg/ml) and anti-BMP9 neutralizing antibodies (1 µg/ml). FIG. 17F, Quantification of relative sprout length per object.

FIG. 18A, Schematic representation of cell injection into the early blastula stage zebrafish embryo. FIGS. 18B and 18B', A representative image of Fib-iPSC-derived vessel type structures (in red) within the embryonic zebrafish Tg(fli1:GFP) (in green) 6 days after implantation, with magnification of the vessel. FIGS. 18C and 18C', A representative image of BOECs-iPSC-derived vessel-type structures (in red) within the embryonic zebrafish Tg(fli1:GFP) (in green) 6 days after implantation, with magnification of the vessel. Scale bar 100 µm and 20 µm respectively. FIG. 18D, 48 hpf implantation of BOECs-iPSC-ECs and FIG. 18E, HUVECs. BOECs-iPSC-ECs (in red) integrated within the major vascular structure of the zebrafish Tg(fli1:GFP) (in green) embryos whereas HUVEC integration was poor (in red). Representative images were taken at 5 dpi. FIG. 18F, Comparison of the length of vessels formed from Fib-IPSC-ECs and BOECs-iPSC-ECs. 30 zebrafish were randomly selected, and the vessels within the yolk sac were measured using Leica software. There was no statistically significant difference between the groups. FIG. 18G, Comparison of BOECs-iPSC-ECs and HUVECs integration after 48 hpf implantation into the vessels located within the embryonic zebrafish. Representative images were taken at 5 dpi. HUVEC n=117, BOECs-iPSC-ECs n=115. (FIGS. 18B, 18C, 18D, 18E) Scale bar 100 µm. (FIGS. 18B', 18C') Scale bar 20 µm.

FIG. 19A, MATRIGEL® tube formation assay. FIG. 19B, Two-dimensional co-culture system comprising of hPSC-derived ECs co-cultured with hPSC-derived mural cells or HUVEC co-cultured with human foreskin fibroblasts.

FIGS. 20A-20D: Two-dimensional co-culture system comprising of hPSC-derived ECs co-cultures with hPSC-derived mural cells. FIG. 20A, Representative immunofluorecent staining of the co-culture system at day 7 in standard growth medium and upon supplementation with SB431542 (10 µM), ECs are visualized with anti-CD31 antibody (in white). FIG. 20B, Recognition of endothelial sprouts with the AngiTool program: endothelial sprouts are shown in red and junction point is blue. FIGS. 20C and 20D, Quantification of total tube length and total number of junctions.

FIG. 21A, Representative immunofluorescent images of the day 7 co-culture in standard growth medium and upon supplementation with DAPT (10 µM) and/or SB431542 (10 µM). Immunofluorescent staining of the co-culture at day 7 with the endothelial cell-specific marker CD31 (in green) and Ki67 (in white) (co-culture). Images were acquired with 10× objective in 3×3 montage mode (BD Pathway855). FIG. 21B, Quantification of the Ki67 positive cells and Ki67+ ECs (CellProfiler).

FIG. 23A, Maximum projection images of the day 7 co-culture counterstained with anti-CD31 (in green), smooth muscle cell-specific anti-SM22 (in red), and nuclei were visualized with DAPI (in blue). Representative immunofluorescent images of the day 7 co-culture in standard growth medium and upon supplementation with DAPT (10 µM) and/or SB431542 (10 µM). Scale bar 100 µm. Images were acquired with 20× DRY objective with Leica SP5 confocal microscope. FIG. 23B, Quantification of the total area per object covered by endothelial sprouts (CellProfiler). FIG. 23C, Quantification of the total area covered by SM22 positive cells (CellProfiler).

DETAILED DESCRIPTION

Example 1

Figure 1A:
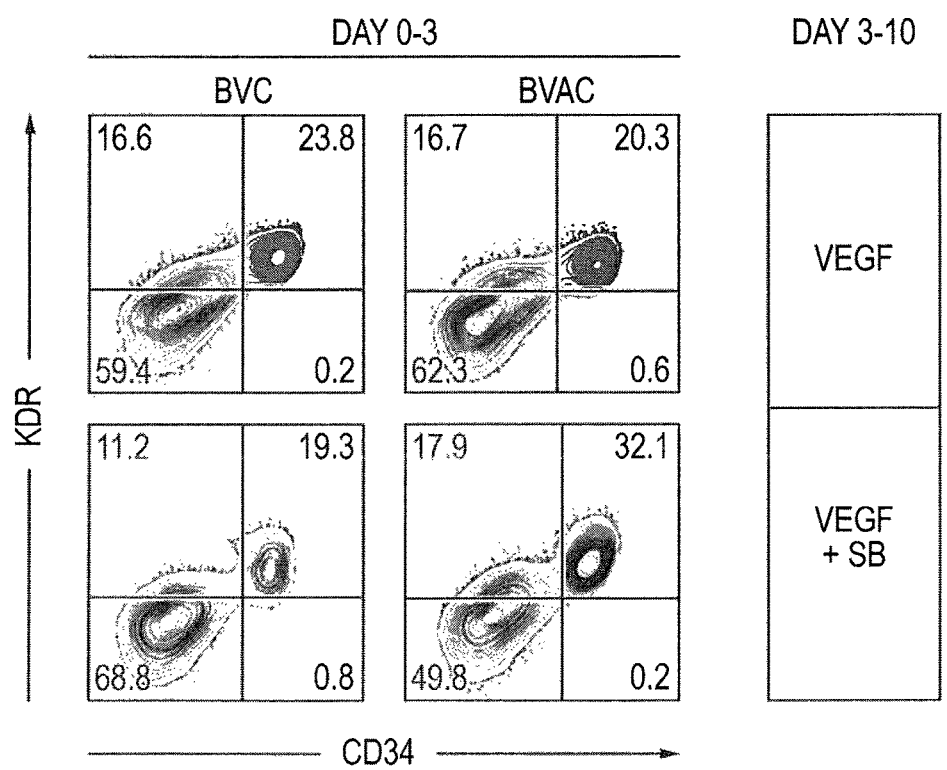
FIGS. 1A and 1B: Mesoderm induction and vascular specification from hPSCs.

Methods
Cell Culture and Differentiation hiPSC lines were generated from Fib or BOECs using conditional lentiviral vectors containing the four transcription factors oct4, c-myc, Klf4 and Sox2, and characterized as described previously (Dambrot et al., 2013; Freund et al., 2008; Orlova et al., manuscript in preparation). hiPSCs and hESC (line HES-NL4; (van de Stolpe et al., 2005)) were routinely maintained on growth factor reduced MATRIGEL®-(BD, 354230) coated plates in mTeSR media (StemCell Technologies, 05850) and passaged mechanically. Differentiation was induced three days after passaging colonies by replacing mTeSR medium with the differentiation media based on BPEL (without PVA) (Ng et al., 2008) with timed addition of the following growth factors: 25 ng/ml ActivinA (Miltenyi, 130-095-547), 30 ng/ml BMP4 (Miltenyi, 130-095-549), VEGF165 (R&D Systems, 293-VE) and small molecule inhibitor CHIR99021 (Tocris, 4423). At day 3 and day 7 of differentiation, the media was refreshed with BPEL containing VEGF and 5 µM SB43152 (Tocris, 1614) only. A schematic diagram of the growth factor combinations and timing is provided in FIG. 13.

Magnetic Bead Purification of ECs

Purification of ECs was carried out on day 10 of differentiation with the CD31-labeled Dynabeads (Life Technologies, 1115D), as previously described (Langer et al., 2011; Choi et al., 2008). Briefly, differentiating cultures were washed once with phosphate buffered saline (PBS), and medium replaced by Dulbecco's Minimum Essential Medium (DMEM)+0.1% BSA (Gibco). CD31-Dynabeads were washed twice with DMEM+0.1% BSA, and added drop by drop to the cells in DMEM+0.1% BSA. Dynabeads were incubated with the cells under gentle rotation (10-20 rpm) for 20 minutes at RT. After incubation, cells with the beads were washed once with the PBS, and detached by gentle enzymatic treatment for 5 minutes at RT with 1× TrypLE Select (Life Technologies, 12563029). To ensure good separation of beads and ECs, cells were sequentially washed with the FACs buffer+10% FBS, followed by the FACs buffer alone then with DMEM+0.1% BSA. After the last wash, ECs were re-suspended in human endothelial growth medium serum free medium (hEC-SFM) (Life Technologies, 11111) supplemented with 1% platelet poor plasma (BTI, BT-214), 30 ng/ml VEGF and 20 ng/ml bFGF (R&D systems). ECs were then routinely grown on 0.1% gelatin coated plates, and passaged every 3-4 days with TrypLE Select.

Flow Cytometry (FACS) Analysis

Cells were dissociated with TrypLE Select and washed once with the FACs buffer with the 10% FBS, followed by the single wash with the FACs buffer. The combination of the following antibodies was used for the FACs staining: VE-Cadherin-A488 (eBiosciences, 53-1449-41, 1:100), CD31-APC (eBiosciences, 17-0319, 1:200), CD34-PerCP-Cy5.5 (BD Pharmingen, 347203, 1:100), KDR-PE (R&D Systems, FAB357P, 1:50), PDGFRb-PE (BD Pharmingen, 558821, 1:50), CD73-PE (BD Pharmingen, 550257, 1:50), CD105 A488 and PE (Life Technologies, MHCD10504, 1:200). The samples were acquired on LSRII (BD) with the following instrument settings Blue/488 FITC, A488: 505LP-530/30, PerCP-Cy5.5: 630LP-670/14; Yellow/561 PE: 570LP-582/15, APC: 635LP-660/20. In some experiment samples were analyzed with the MACSQuant VYB (Miltenyi).

Immunofluorescence of ECs

ECs were grown to confluence on fibronectin (FN)-coated glass coverslips (Sigma, F1141, 2 ug/ml). Immunofluorescent staining was performed as previously described (Orlova et al., 2006). The following antibodies were used: VE-Cadherin (CellSignaling, 2158, 1:200), CD31 (Scbt, sc-1506-R, 1:200), vWF (Dako, A0082, 1:200).

Gene-Expression Analysis

Total RNA was isolated from cultured cells using the NUCLEOSPIN®RNA II Kit (Macherey-Nagel) combined with AMBION® TURBO™ DNase treatment (Life Technologies). Total RNA purified from cultured cells was used to generate cDNA using the ISCRIPT® cDNA Synthesis Kit (Bio-Rad). qPCR was performed using the CFX96™ Real-Time System (Bio-Rad) and data was analyzed with Bio-Rad CFX Manager 3.0 software. For each reaction 200 ng cDNA was used in a 20 µL qPCR mixture containing 10 µM FW primer, 10 µM RV primer; 10 µL iQ™ SYBR Green Supermix (Bio-Rad). Samples were denatured for 3 minutes at 95° C. followed by 42 cycles of 15 seconds at 95° C., 30 seconds at 60° C. and 45 seconds at 72° C. Melt-curve analysis was performed directly after the amplification protocol under the following conditions: 10 seconds denaturation at 95° C. and 0.5° C. increments of 5 seconds from 65° C. to 95° C. Primers that were used for qPCR are shown in supplementary Table 1.

MATRIGEL® Angiogenesis Assay

The endothelial tube formation assay was performed as previously described with slight modifications (Arnaoutova and Kleinman, 2010). hiPSC-derived ECs were plated into 96-well plates at a density of 15,000 cells/well on the top of growth factor reduced MATRIGEL® that had been solidified for 30 minutes at 37° C. prior to the plating of the cells. Endothelial SFM (Invitrogen) supplemented with 1% platelet poor plasma, VEGF and bFGF were used for the tube formation assay. In order to enhance visualization and facilitate quantification of tube formation, ECs were labelled with the general cytoplasmic labeling agent PKH-67 according to the manufacturer's protocol (Sigma, PKH67GL). Endothelial tubes were imaged with the BD Pathway 855 imaging system using the 4× objective and 2×2 Montage mode. Total area and total tube length of the endothelial sprouts was quantified using the Wimasis quantification method (on the World Wide Web at wimasis.com).

Capillary-Like Network Formation by ECs in Co-culture with Pericytes

The endothelial capillary-like network formation assay was carried out as previously described but with major modifications (Evensen et al., 2013). These included using both ECs and pericytes derived from human iPSC lines. This is described in more detail elsewhere (Orlova et al., manuscript in preparation). ECs were labelled with the general cytoplasmic labeling dye (PKH-26). For the sprouting assay, 12,000 ECs derived from both control and diseased lines were plated with 50,000 control iPSC-derived pericytes/well on 0.1% gelatin coated 96-well plates in EGM-2 (Lonza, CC-3162). Next day and on the day 4 of the assay, medium was replaced with new EGM-2 media containing tested compounds as indicated in the figure legends. Endothelial-pericyte co-culture was terminated on day 7 of the assay each well immunofluorescently stained for quantification, as follows: co-cultures were fixed with the 4% paraformaldehyde (PFA), permeabilized with the 0.1% TX-100 and blocked with the normal goat serum (Dako). Endothelial sprouts were visualized with the mouse anti-CD31 (Dako, 1:200). In some experiment with the mouse blocking antibodies, rabbit anti-CD31 (Scbt, 1:200) was used instead. Pericytes were visualized with antibodies against SM22 (Sigma, 1:200). The endothelial network was imaged with the BD Pathway 855 system using the 4× or 10× objective and 2×2 (or 3×3) Montage mode. Total area covered by the endothelial sprouts was quantified with the protocol developed within cell image analysis software CellProfiller (Broad Institute). High magnification images were acquired with the SP5 confocal microscope, using 10× and 40× objectives.

Results

Figure 13:
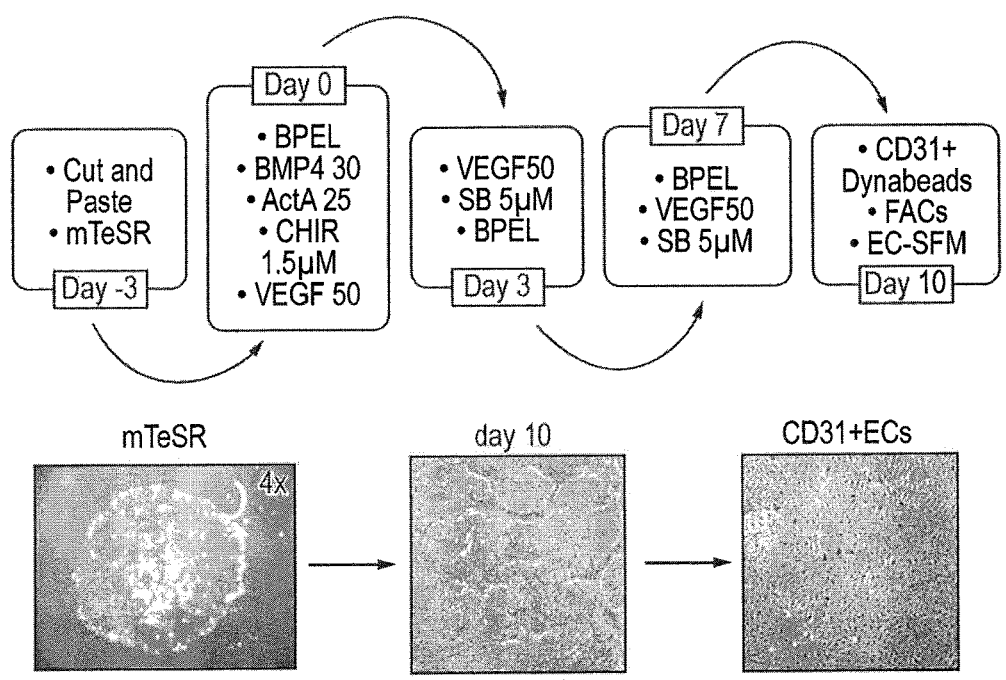
FIG. 13: Schematic diagram of the differentiation protocol.

Monolayer Differentiation Protocol for Mesoderm Induction and Vascular Specification from hPSCs In order to induce mesoderm differentiation in hPSCs, defined media based on the previously published BPEL protocol was used (Ng et al., 2008). A schematic representation of the differentiation protocol is shown in FIG. 13.

Figure 1B:
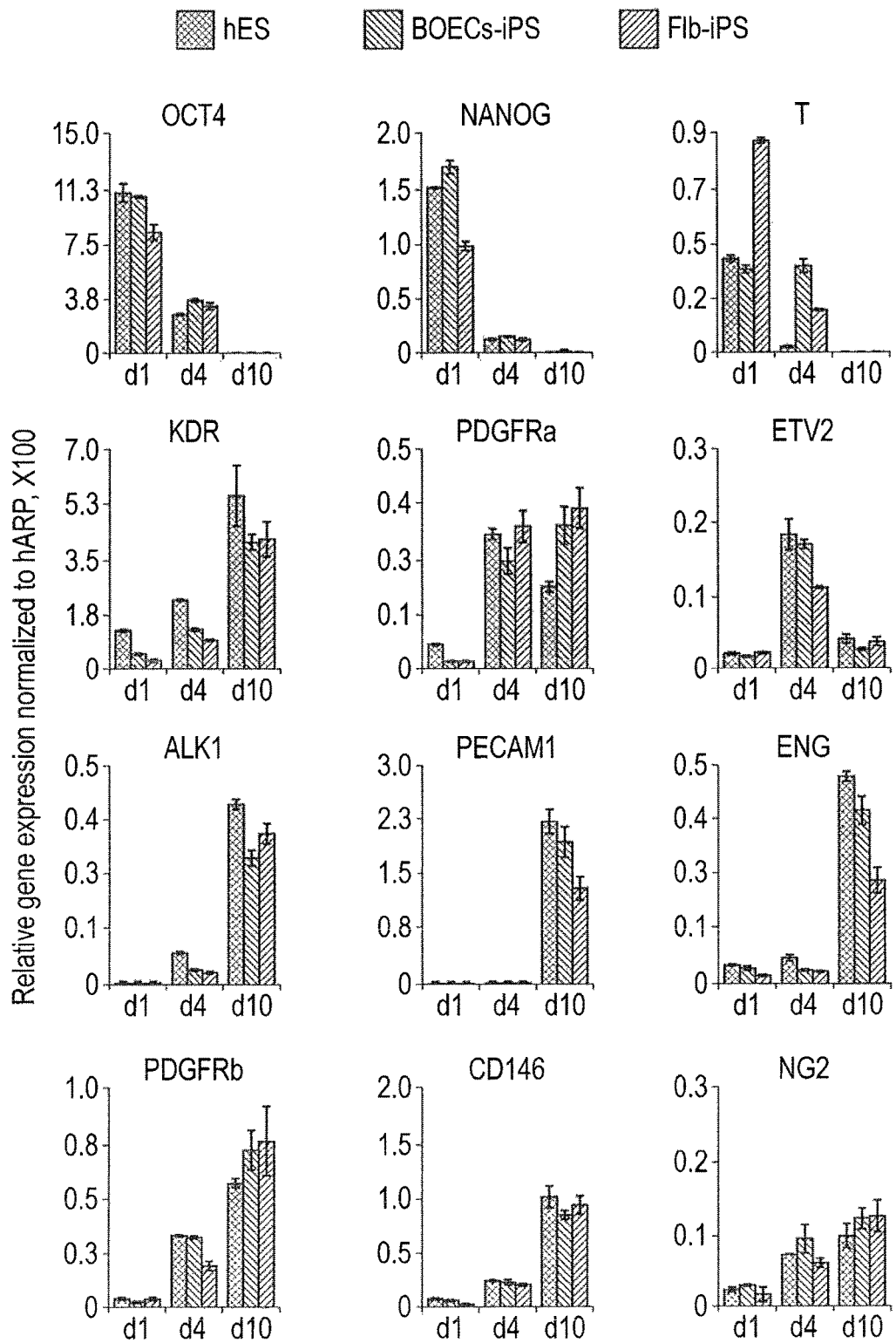

The mesoderm induction conditions were further optimized based on our experience and that of others previously with the mesoderm induction in aggregates called embryoid bodies (EBs) or Spin EBs if derived by forced aggregation (Costa et al., 2013; Yu et al., 2012; Elliott et al., 2011; Ng et al., 2008) and unpublished data. The objective was to develop a robust system to induce differentiation in defined media from hPSCs grown under fibroblast feeder-free conditions that could be easily adapted for large scale production of ECs from multiple iPSCs lines and at the same time provide highly pure populations of cells for functional tests and drug screening applications. Combinations of the following growth factors were first tested from day 0-3 of differentiation: BMP4 (B) (30 ng/ml), VEGF (V) (50 ng/ml) in the presence of a canonical WNT ligand or GSK3-kinase inhibitor (CHIR99021)(C) (1.5 µM) (BVC), or the same conditions with additional Activin (A) (25 ng/ml) (BVASC). The cultures were then refreshed at day 3 with additional VEGF or VEGF and SB (SB-431542) (5 µM). Examination of cell surface expression of the hemato-endothelial-specific marker (CD34) or the cardiovascular marker Kinase insert Domain Receptor (KDR; also known as VEGFR2) by flow cytometry demonstrated in robust induction of expression by day 10 (FIG. 1A) with either protocol in the hiPSC line shown. Notably, additional supplementation with Activin on days 0-3 resulted in more robust and reproducible differentiation among a range of iPSC lines available (data not shown). In addition, supplementation with VEGF together with SB (SB-431542) (5 µM) resulted on average in a 30% increase in the yield of ECs, that was consistent among several cell lines tested and in line with findings by other groups (James et al., 2010; Kennedy et al., 2012). The defined differentiation conditions resulted in the generation of CD34+/KDR+ cells in a variety of hPSC cell lines recently derived and characterized, including several generated from human adult skin fibroblasts (Fib-iPSCs) and blood outgrowth endothelial cells (BOECs-iPSCs) as well as hESC (HESC-NL4) (Dambrot et al., 2013; Davis et al., 2012; Freund et al., 2010; 2008). To confirm efficient mesoderm induction rather than EC proliferation as the reason for high numbers of ECs in the cultures, the expression of various early mesoderm genes were examined, as well as EC-specific genes (FIG. 1B). Robust down-regulation of pluripotent stem cell markers, such as OCT4 and NANOG by day 4 of differentiation, was followed by the induction of primitive streak/mesoderm lineage markers, such as T and PDGFRa, over the same time period. The early endothelial-specific transcription factor (ETV2) was also up-regulated at day 4, followed by robust induction of endothelial-specific genes by day 10 of differentiation (ALK1, ENG, PECAM1, KDR). Interestingly, also observed was induction of early mesenchymal/pericyte cell markers such as PDGFRb, CD146 and NG2, but not of contractile smooth muscle cell markers. Overall, no significant differences were observed in the expression of mesoderm and endothelial-specific genes between the different lines.

Efficient Protocol for Isolation and Expansion of hPSC-Derived ECs

Figure 2A:
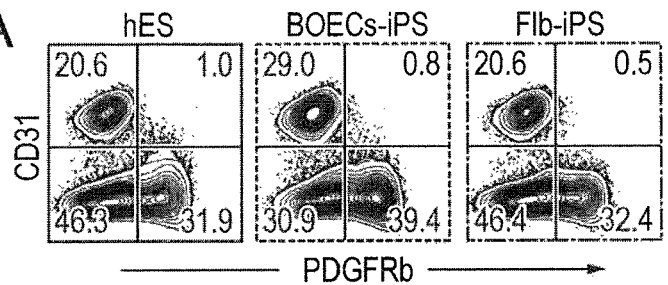
FIGS. 2A-2D: hPSCs differentiate efficiently into endothelial and mesenchymal cells independent of the donor cell origin.
Figure 2B:
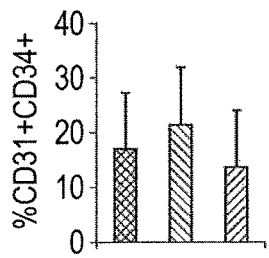
Figure 2C:
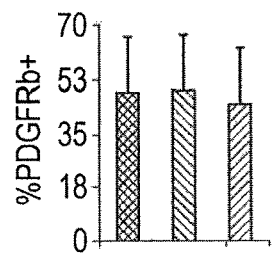
Figure 2D:
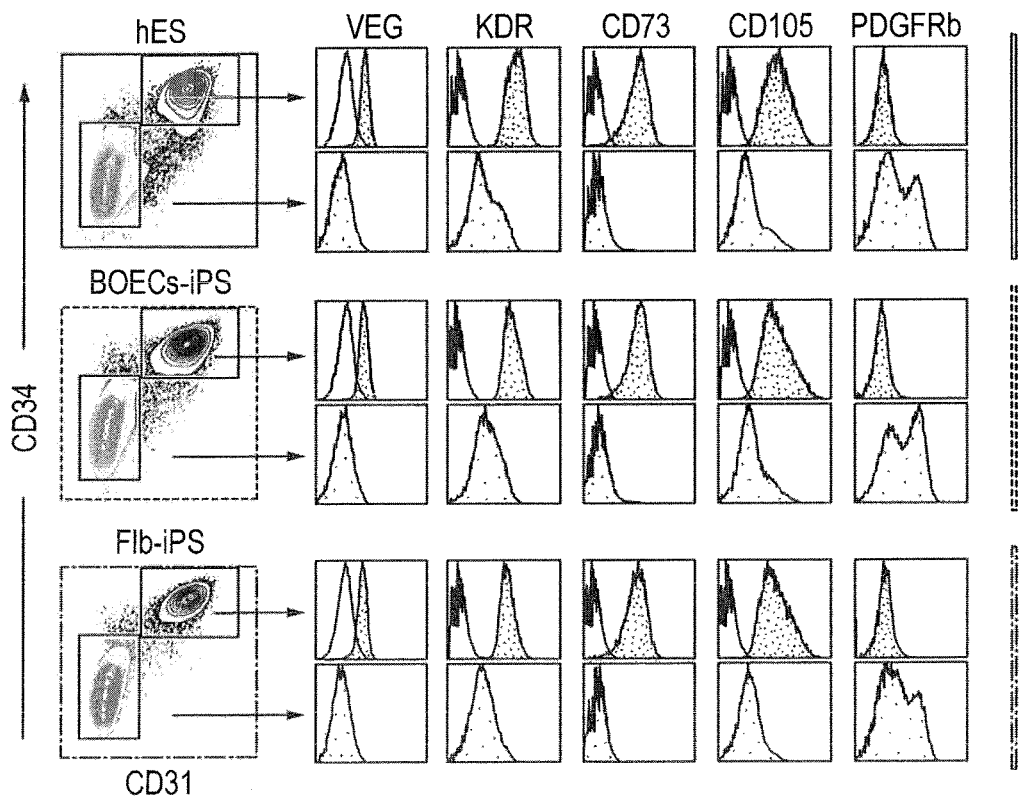

Flow cytometric analysis of different hPSC lines at day 10 of differentiation showed robust induction of a CD31+ EC population, as well as CD31-PDGFRb+ mesenchymal cells at day 10 of differentiation (FIG. 2A). The differentiation efficiency also using this assay was similar and consistent among different hPSC lines tested, with average percentages 10-30% of CD31+/CD34+ cells, as well as ~30% of PDGFRb+ mesenchymal cells (FIGS. 2B and 2C). Additionally, expression of other endothelial and mesenchymal cell markers on the endothelial CD31+/CD34+ population were investigated, as well as PDGFRb+ cells. Importantly, CD31+/CD34+ cells expressed reliable and comparable levels of other endothelial-specific markers (VE-Cadherin, KDR, CD73 and CD105), and were negative for PDGFRb. By contrast, the CD31−/CD34− population strongly up-regulated PDGFRb. Interestingly, expression of other mesenchymal stem cell markers (CD105 and CD73) in the CD31−/CD34− population was not observed at day 10 of differentiation (FIG. 2D).

Next an efficient protocol for easy isolation of ECs from the mixed differentiated populations was developed. Dynabeads were used by preference for this above FACS since it facilitates rapid isolation of adherent cells without prior need for enzymatic digestion, as shown in our previous work isolating mouse ECs from primary tissues (Langer et al., 2011; Choi et al., 2008). CD31 was considered as the most appropriate marker for positive selection of ECs since the differentiation protocol resulted in a large number of ECs, and not other CD31+ hematopoietic progenitors, as evidenced by flow cytometry analysis showing that all CD31+ cell expressed VE-Cadherin and other endothelial-specific markers (FIG. 2D).

Figure 3A:
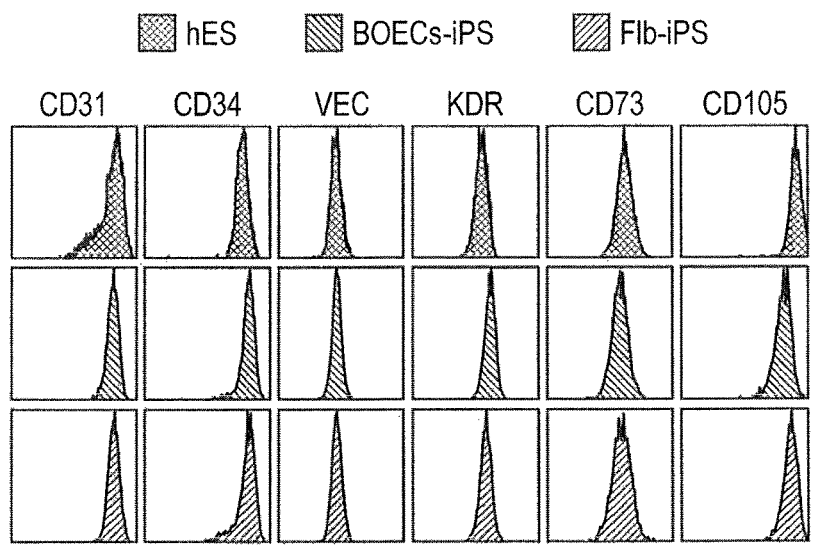
Figure 3B:
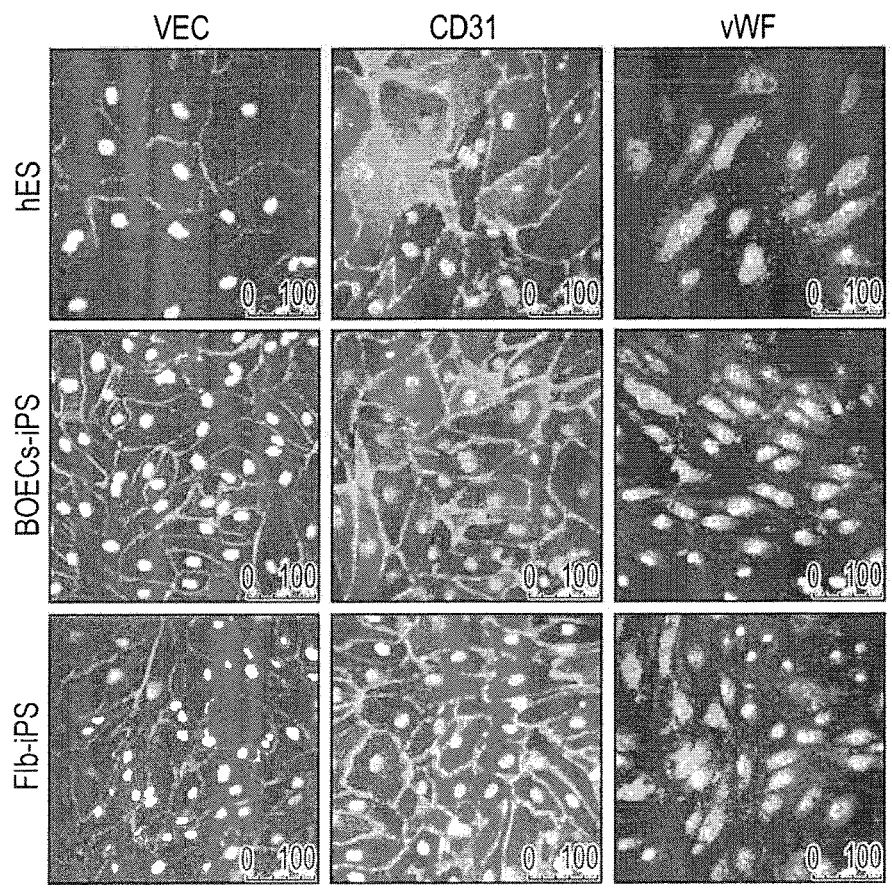

The protocol facilitated isolation of ECs with average purities >95% after just one selection round (FIG. 3A). This is particularly important for reproducible and specific functional and signal transduction studies in cell populations. Furthermore, ECs isolated from hESC, BOECs-iPS or Fib-iPS cell lines all expressed comparable levels of endothelial-specific surface antigens such as CD31, CD34, VE-Cadherin, CD73, and CD105 (FIG. 3A). Immunofluorescent analysis revealed junctional localization of VE-Cadherin and PECAM-1, as well prominent intracellular staining for von Willebrand factor (vWF) (FIG. 3B).

Gene expression analysis revealed on average two-fold higher expression of pan-endothelial markers such as PECAM-1, VE-Cadherin and KDR to levels in HUVEC or Human Aortic ECs (HAoEC) (FIG. 3C). Interestingly, iPSC-derived ECs expressed significantly higher levels of arterial marker Ephrin-B2 compared with HAoEC, although expression levels of another more prominent arterial-specific marker Hey2, previously identified by gene expression profiling of primary human endothelial cells (Chi, 2003), were comparable with HAoEC. In addition, lower levels of the venous marker CoupTFII was observed, although EphrinB4 levels were comparable to HUVEC. Interestingly, iPSC-derived ECs did express some lymphatic associated markers such as LYVE1 and VEGFR3, that possibly indicate an embryonic or fetal maturation state in hiPSC-derived ECs, since LYVE1 and VEGFR3 expression has been described in embryonic vasculature or during active angiogenesis, and are thus not lymphatic endothelial-specific markers in the mouse embryo (Gordon et al., 2008; Benedito et al., 2012). Supporting this, no expression of the lymphatic-specific markers Podoplanin and Prox1 was observed (data not shown).

To increase the value of hPSC-derived ECs as a resource, it was considered of value to establish conditions for their serial propagation in culture. This has not been trivial for many hPSC derivatives with the exception of neural progenitors since they often senesce or become post-mitotic. Thus, several media were screened for their ability to support EC expansion and found that endothelial cell-serum free media (ECs-SFM) with additional VEGF (30 ng/ml), bFGF (20 ng/ml) and 1% bovine platelet poor extract was the most robust as previously reported for blood brain-specific ECs from hPSCs (Lippmann et al., 2012). Interestingly, supplementation with the 1% bovine platelet poor extract significantly increased the proliferation rate of hESC- and hiPSC-derived EC compared to VEGF and bFGF alone or VEGF with bFGF (data not shown).

Functional Competence of hPSC-ECs is Independent of hPSCs Origin

Next, functional competence of endothelial cells derived from BOECs-iPSC and Fib-iPSC were examined. It has been described that iPSC derived from some tissues may retain some epigenetic memory of their tissue of origin after reprogramming. Although no increase was found in the differentiation efficiency to ECs even when BOECs had been used as a source of hiPSC, it was wondered whether they would be functionally different assays comparing the different sources directly. Two standard functional EC assays were carried out: tube formation on MATRIGEL® and sprouting in endothelial-pericyte cell co-culture. ECs derived from either BOECs-iPSCs or Fib-iPSC displayed similar functionality (FIGS. 4A-4D). In the MATRIGEL® tube formation assay, ECs started forming cord like structures as early as 6 hours post-seeding. Interestingly, the endothelial cords remained stable up to 48 hours (FIG. 4A) with the prominent cord structures still being present up-to 72 hours (data not shown). These results differ strikingly from HUVEC where cord structures tend to regress rapidly after 24 hours, both in our hands as well as in publications by other groups. Measurement of the total tube length and area covered by endothelial sprouts showed comparable values for BOECs-iPSC and Fib-iPSC-derived ECs (FIG. 4B).

The functionality of BOECs-iPSC and Fib-iPSC-derived ECs in the endothelial-pericyte co-culture sprouting assay was next examined (Evensen et al., 2010; 2013). For this, pericytes/MSCs derived from the BOECs-iPSC line were used. Interestingly, both BOECs-iPSC as well as Fib-iPSC-derived ECs formed well-organized sprouts at day 7 of co-culture.

hiPSC-derived ECs express exceptionally high levels of TGFβ superfamily receptors (data unpublished) and were highly responsive to the corresponding ligands and targeting of the TGFβ signaling (FIGS. 10A-10E, and Example 2).

Figure 5:
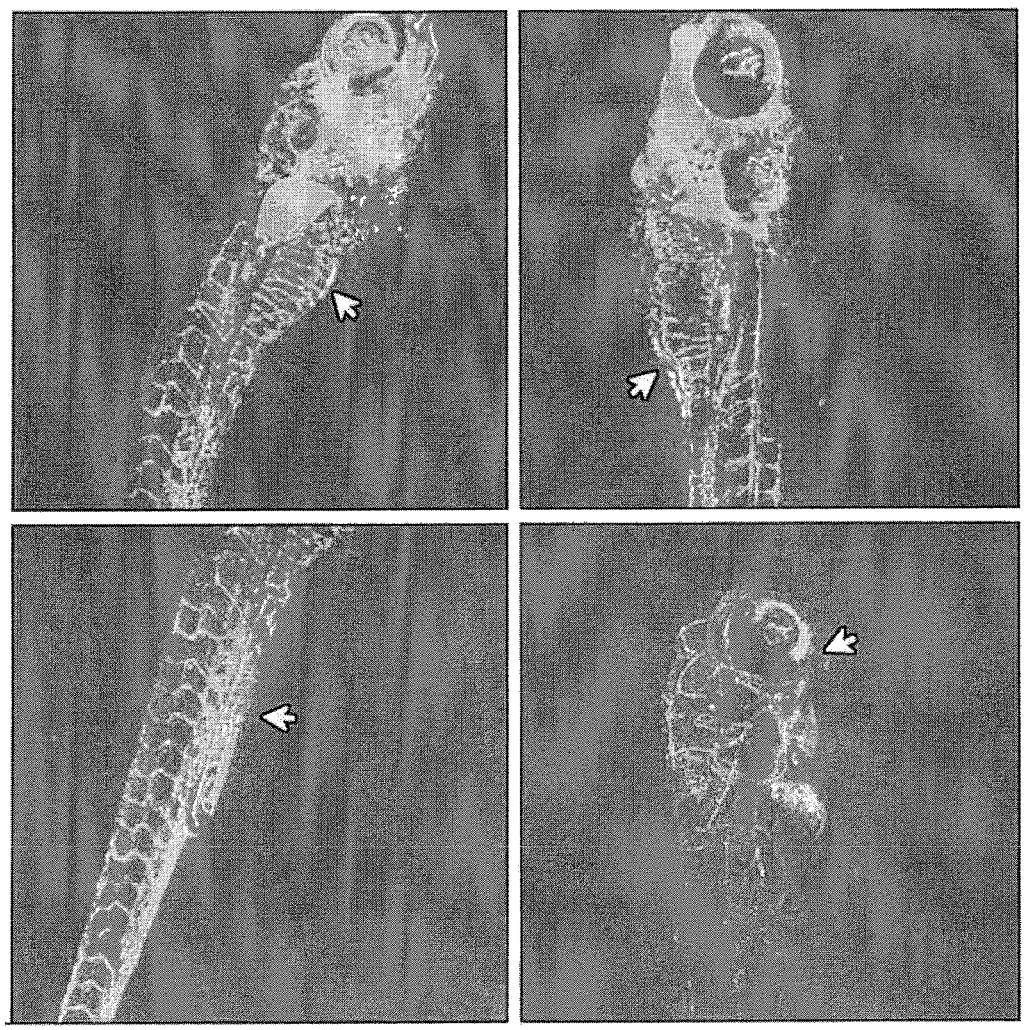
FIG. 5: Vascular competence of hPSC-derived endothelial cells in zebrafish xenograft model.

Next, grafting potential of hiPS-derived ECs into the host vasculature in the novel system was texted where zebrafish was used as a host. Interestingly, upon grafting significant parts of zebrafish vasculature were made of hiPS-derived ECs (FIG. 5).

Functional Competence of hPSC-ECs is Independent of hPSC Origin

Figure 19A:
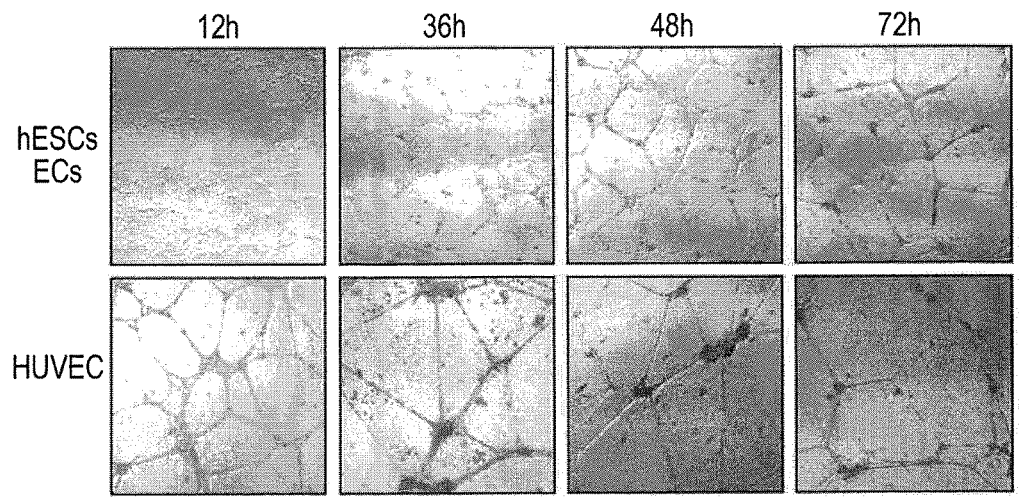
FIGS. 19A and 19B: Functional characterization of hPSC-derived ECs.
Figure 19B:
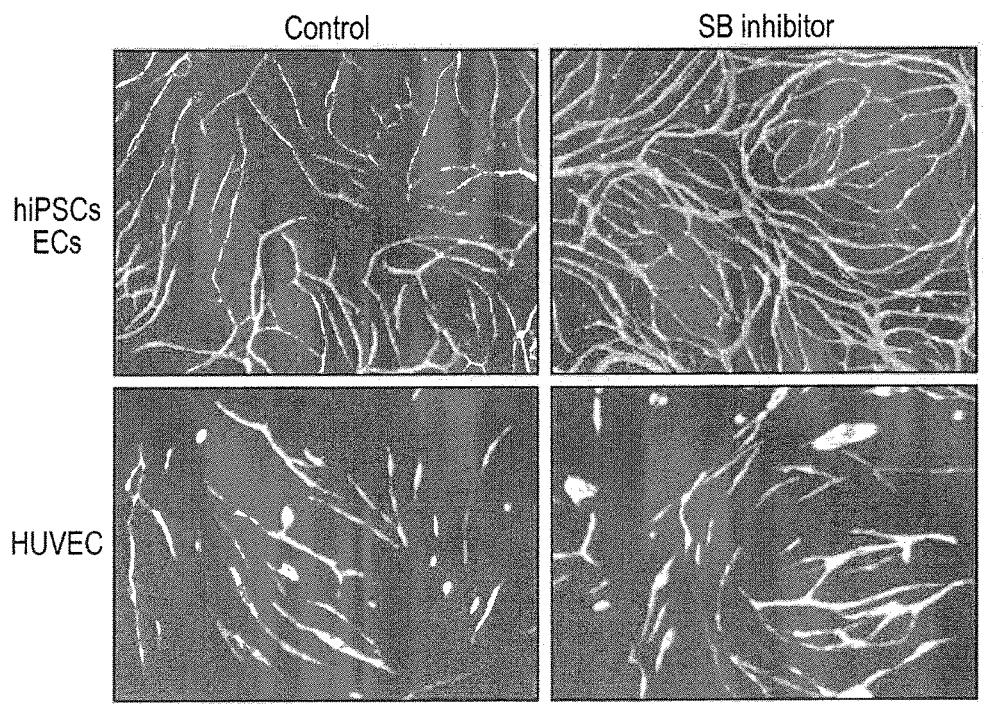
Figure 21A:
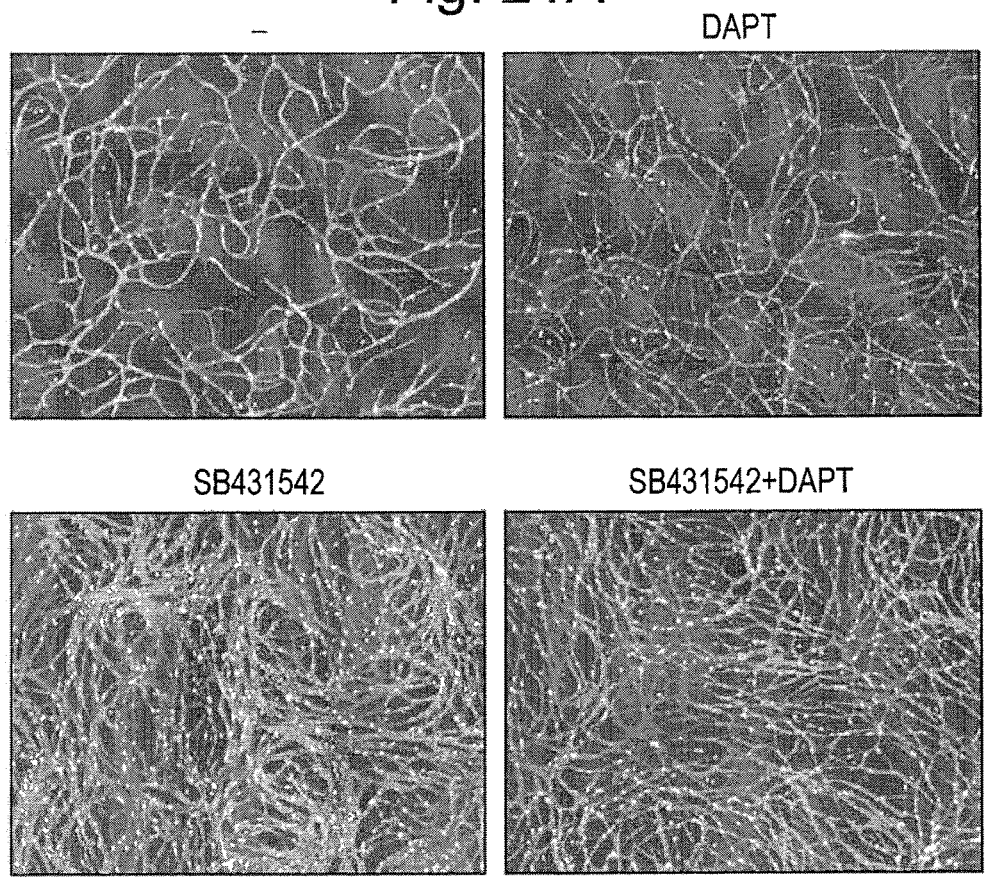
FIGS. 21A and 21B: Increased endothelial cell proliferation in a co-culture system upon supplementation with the ALK5 inhibitor SB.
Figure 21B:
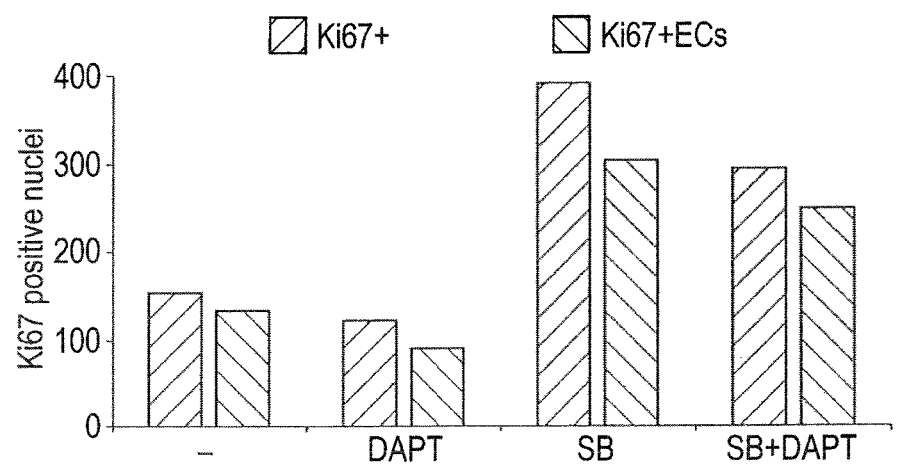
Figure 22:
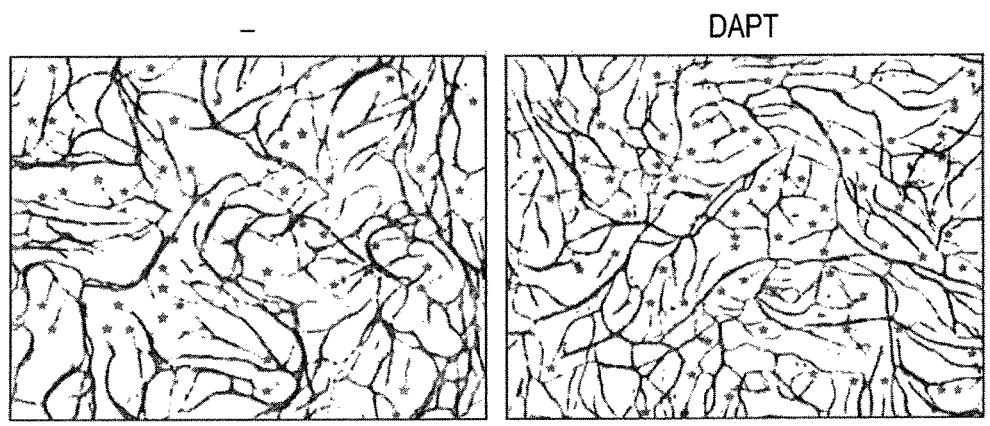
FIG. 22: Quantification of tip-cells in the 2D co-culture system (red starts), endothelial sprouts are displayed in black. Supplementation with DAPT results in an increase in the number of tip cells (46 vs 64).
Figure 23A:
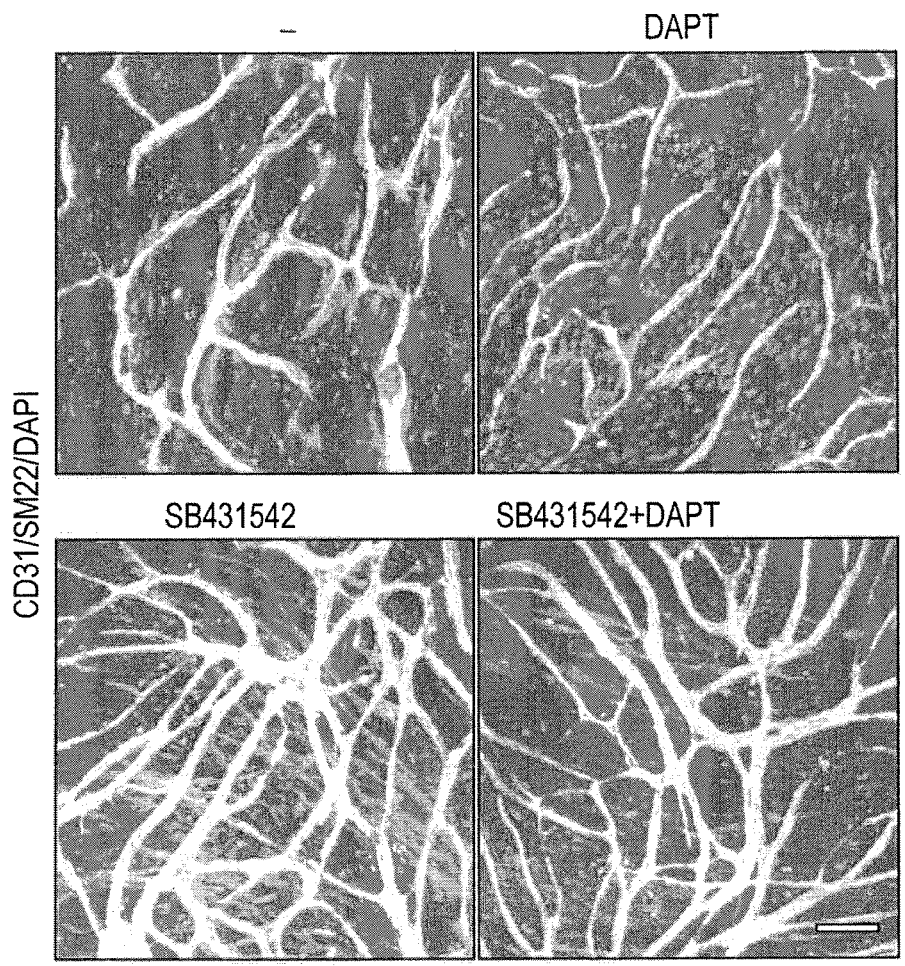
FIGS. 23A-23C: Modeling endothelial-pericyte interactions in vitro vascular plexus formation model upon co-culture of hiPSC-derived ECs and hiPSC-derived pericytes/MSCs.
Figure 23B:
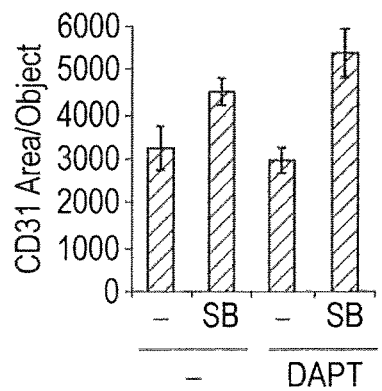
Figure 23C:
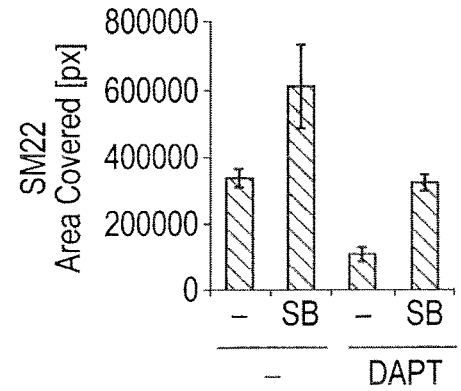

Here, further evidence is provided that hPSC-ECs exhibit exceptional functionality when compared to HUVEC. It is demonstrated that hPSC-ECs perform much better in zebrafish xenograft model in vivo, and demonstrate higher incorporation efficiency into the zebrafish host vasculature compared to HUVEC (FIGS. 18A-18G, addition to the patent FIG. 5). In addition, more data on better functionality of hPSC-ECs in vitro compared to HUVEC was provided: 1) in vitro MATRIGEL® cord formation assay, where hPSC-ECs from a stable vascular network that lasts up to 72 hours and HUVEC cord structure regress rapidly after 24 hours (FIG. 19A, addition to FIGS. 4A and 4B, and FIGS. 9A-9C); 2) 2D co-culture system, where hPSC-ECs form better vascular network and are highly sensitive to TGFb-mediated inhibition (FIG. 19B, addition to FIGS. 4C, 4D, and FIGS. 10A-10E).

Importantly, a 2D co-culture system with hPSC-derived vascular cells, namely endothelial cells and SMCs, that are derived from hiPSCs can be used to model primary vascular sprouting, with the assessment of the total vessel length and the complexity of the vascular network, such as number of junctions and endothelial tip cells (FIGS. 20A-20D and 21A, 21B).

Discussion

Induction CD31+ CD34+ endothelial progenitors from hPSC has been described by several groups. However, most of the published protocols are based on serum-containing media or require co-culture with stromal cell lines (Li et al., 2011; Kane et al., 2010; Hill et al., 2010; Nourse et al., 2009; Tian et al., 2009; Choi et al., 2009). Serum based protocols are highly dependent on particular batches of serum, which often results in high batch to batch variation and problems with reproducibility. Also noted was that serum likely does not support a stable EC phenotype but rather promotes endothelial-to-mesenchymal transitions (unpublished data), much as previously reported by others (Li et al., 2011). Presently, the most efficient protocols for derivation of hemato-endothelial progenitors require differentiation on stromal cell lines (the most commonly used are OP9, M2-10B4, S17 or AM20.1B4) (Hill and Kaufman, 2007; Hill et al., 2010; Choi et al., 2009; Hexum et al., 2011) At the same time though, these protocols have disadvantages, including high variability, stromal cell line quality and type, and limited throughout for production. More recently published protocols on differentiation in defined media require either EB or spin EB systems (Costa et al., 2013; Yu et al., 2012; White et al., 2012). These protocols are quite efficient, however are more difficult to adapt for scaling up. In addition, for the spin EB system hPSC lines have to be adapted to single cell, enzymatic passaging for bulk culture rather than as colonies which can be difficult and time consuming. This might not be convenient if working with the multiple diseased lines hIPSC lines at the same time. Rather high line-to-line variation in the spin EB system was also noticed when using it for hiPSC (Orlova, unpublished). The protocol developed here to induce EC differentiation has high line-to-line reproducibility and is suitable for hPSC growing in simple, routine culture conditions, such as the mTeSR1 system, without major adaption or skill.

In addition, fully defined conditions were developed that not only result in efficient differentiation but also support expansion of hPSC-derived ECs. These ECs can be passaged up to 4-5 times without loss in proliferation rate while maintaining typical EC morphology and expression of typical EC markers (CD31, VE-Cadherin). Furthermore, the differentiation and expansion protocols and media facilitate easy scale up of ECs production and results in ECs that can be cryopreserved and thawed without loss of functionality (Orlova et al., HHT1 manuscript). Fully defined conditions have multiple advantages over serum- or stromal cell-containing conditions for expansion of endothelial cells including better control over the growth factor composition available to the cells. TGFβ and BMPs, for example, are present in serum and are known to have variable and concentration dependent effects on ECs. These could be the cause of at least some of the batch to batch variation in serum used in various assays (reviewed elsewhere and (Orlova et al., 2011)). Therefore, it is important to standardize endothelial-based assays by using serum-free growth media if at all possible. In addition, serum also is the source of major matrix proteins such as fibronectin, the presence of which may confound interpretation of results. Ultimately, serum- and feeder/stromal cell line-free conditions will be required for GMP-qualified production processes should ECs from hPSC be clinically applicable.

ECs exhibit remarkable heterogeneity in vivo (Aird, 2012; 2007). Recent work by Chong et al. has also indicated that embryonic ECs have mixed identity (Chong et al., 2011). In addition, they also express some lymphatic endothelial markers such as LYVE1 or VEGFR3, without acquiring the capacity for a real lymphatic PC fate that should include up-regulation of Prox1 expression (Gordon et al., 2008; Karunamuni et al., 2009). In summary, based on their gene and protein expression, it was concluded that hPSC-derived ECs resemble embryonic ECs rather the than yolk sac type.

In addition, ECs in different tissues are affected by local environmental cues, which result in tissue-specific differences in EC phenotype (Aird, 2012). Interestingly, studies by several groups demonstrated that tissue-specific differences are lost upon in vitro culture (Aird, 2012; Dyer and Patterson, 2010; Lacorre, 2004). Therefore, the question of whether it is possible to capture certain endothelial cell subset phenotypes in vitro remains open and requires additional research.

Alteration in endothelial cell identity, so-called transdifferentiation, is also the cause of multiple vascular diseases. For example, loss of arterial/venous endothelial cell identity is a characteristic of hereditary hemorrhagic telangiectasia (HHT). HHT patients develop fragile blood vessels and suffer from multiple telangiectasia that result in recurrent nosebleeds and arteriovenous malformations (AVMs) when occurring in lung, brain, liver or the gastrointestinal tract and can be life threatening. Loss of arterial identity is observed in AVMs in mouse models of HHT in which the endoglin, responsible for HHT type 1, has been mutated (Mahmoud et al., 2010). It has been shown that venous ECs are more prone to inflammation and atherosclerosis, which makes them a less appropriate cell type for engineering of tissue grafts. Application of anti-inflammatory dexamethasone promotes arterialization of vascular grafts (Zakkar et al., 2011) and decreases inflammatory responses.

Targeting of the TGFβ pathway can be useful for anti-tumor/anti-angiogenic therapy in patients and some drugs like TRACON, humanized antibodies against TGFβ, anti-ALK1 (PF-03446962), chemical ALK4/ALK5/ALK7 inhibitors (SB431542 and LY364947) are in clinical trials for cancer (Seon et al., 2011; Cunha and Pietras, 2011; Akhurst and Hata, 2012). Therefore, this can be potentially a useful system to screen for anti-angiogenic drugs.

In addition, hiPS-derived ECs exhibited superior grafting potential in the host vasculature what makes them potentially very useful for future tissue engineering applications.

Taken together, generation of specific subsets of ECs will be very useful for modeling of human vascular diseases in vitro and for tissue engineering.

Example 2

Results
Derivation and Characterization of HHT1-iPSCs

Figure 6A:
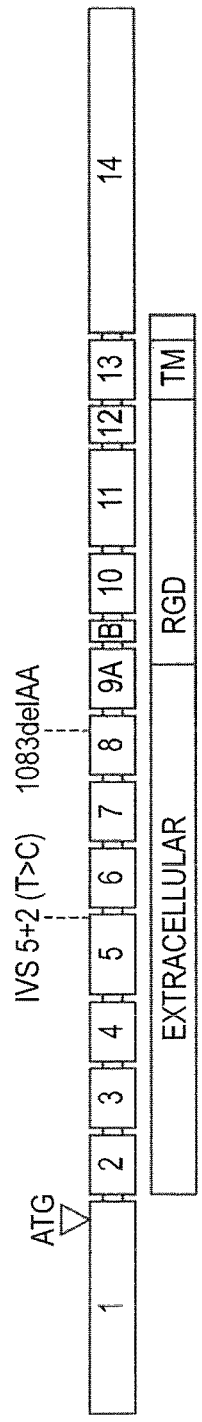
FIGS. 6A-6E: Characterization of HHT1 patient-specific iPSCs.
Figure 6B:
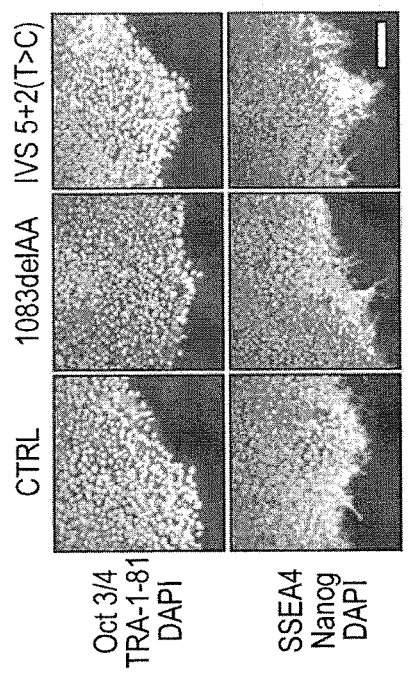
Figure 6C:
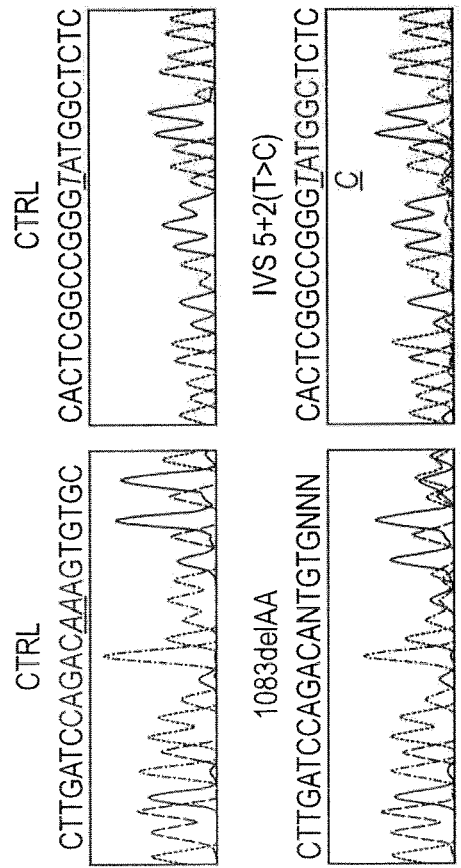
Figure 6E:
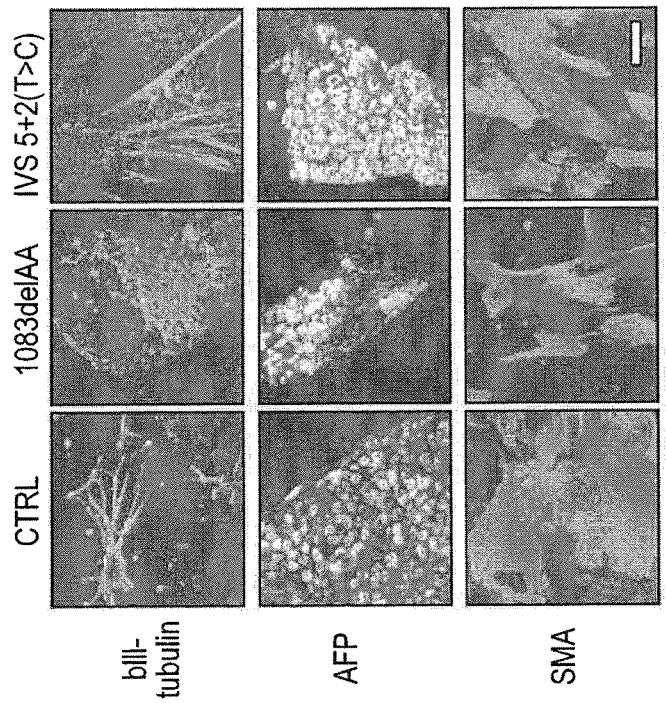
Figure 6D:
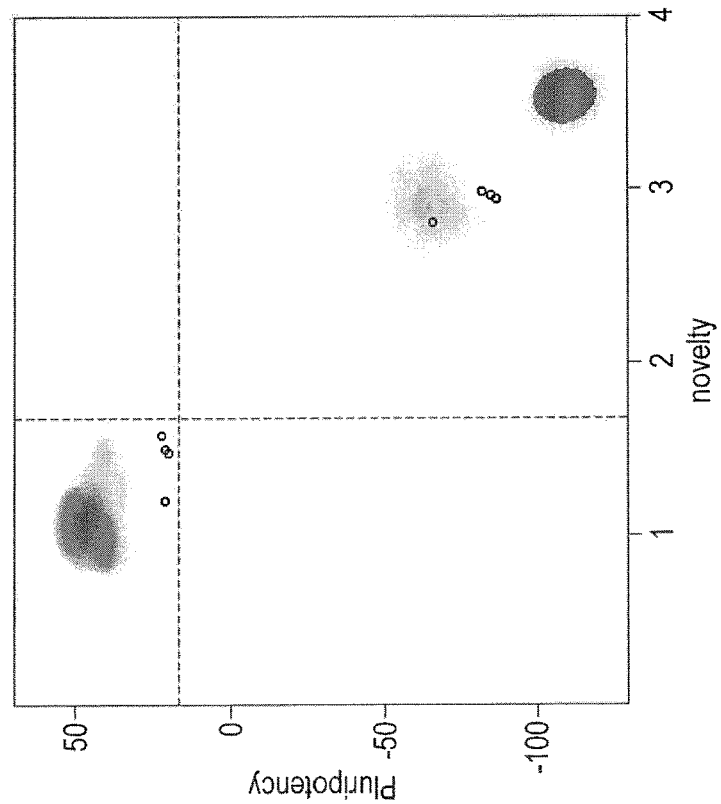
Figure 14:
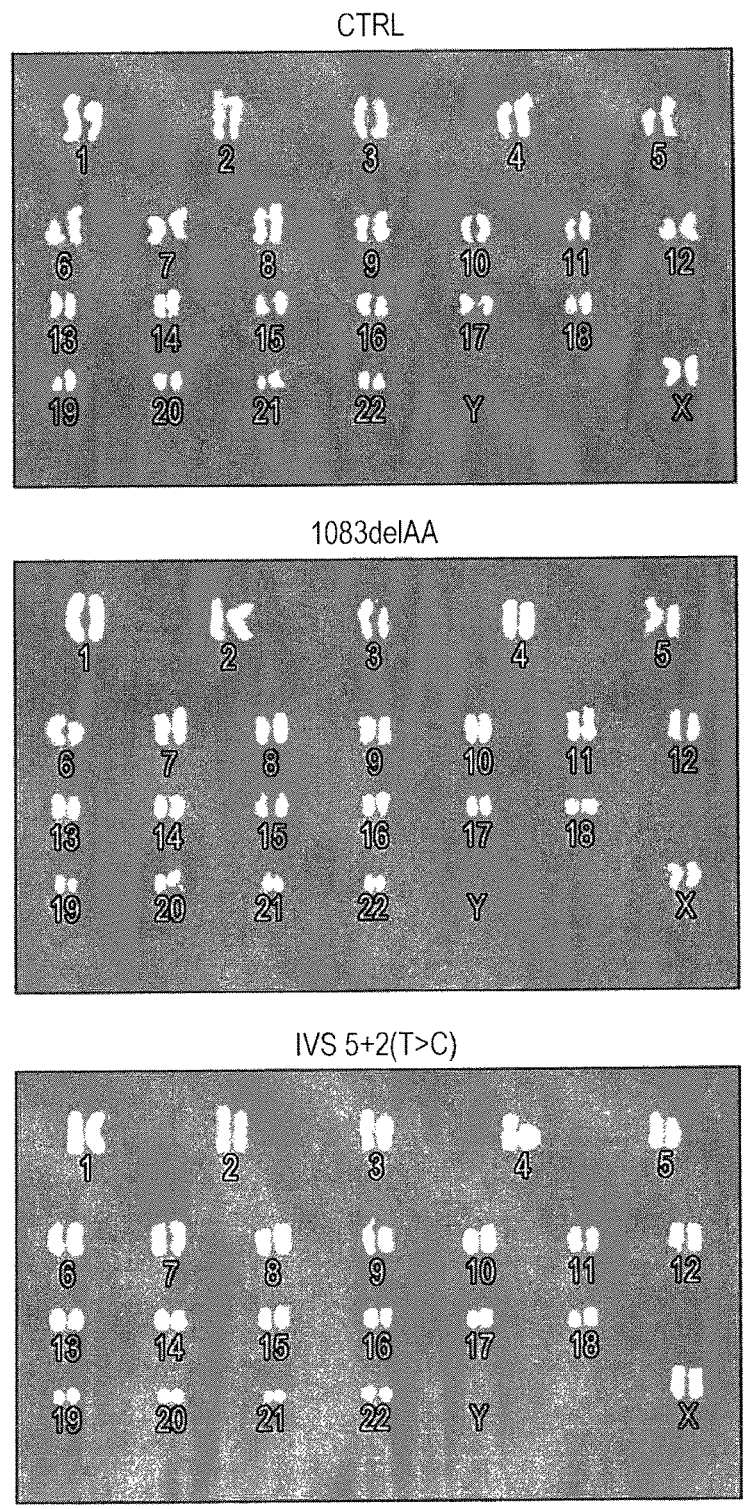
FIG. 14: Characterization of HHT1 patient iPSCs. Normal Karyotype.

Numerous iPSCs clones were generated from somatic tissue from two HHT1 patients with different ENG mutations (FIGS. 6A-6E) with normal efficiencies using standard reprogramming methods (Dambrot et al., 2013) indicating that the mutations did not affect reprogramming as such. Mutations were confirmed by sequencing of genomic DNA isolated from HHT1 patient-specific and control iPSC lines (FIG. 6B). Undifferentiated iPSC lines were maintained on MATRIGEL® in mTESR1 medium for at least 25 passages and expressed typical markers of pluripotent stem cells as shown by immunostaining (FIG. 6C). When allowed to differentiate spontaneously in culture all iPSC lines readily gave rise to the derivatives of the three germ layers, e.g., neurons expressing βIII-tubulin (ectoderm), endodermal cells expressing alphafetoprotein (AFP) and SMCs expressing smooth muscle actin (mesoderm) (FIG. 6E). To confirm pluripotency of the undifferentiated iPSC, PluriTest was used, a bioinformatic assay that predicts pluripotency based on comparison of the gene expression profile of a query sample with that of multiple pluripotent stem cell lines and non-pluripotent cells (Willer et al., 2011). The resulting "Pluripotency Score" and the "Novelty Score" indicate whether the query sample contains a pluripotency signature and whether it resembles normal pluripotent stem cells (PSCs), respectively. As shown in (FIG. 6D, all iPSC lines clustered with normal PSCs. In addition the iPSCs all displayed a normal karyotype (FIG. 14).

Differentiation of HHT1-iPSCs to Endothelial Cells

Figure 7A:
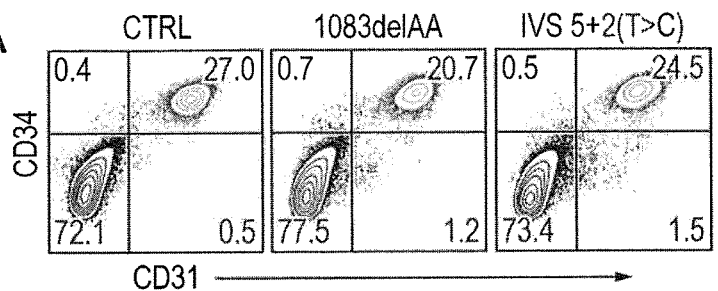
FIGS. 7A-7D: Differentiation of HHT1 patient-specific iPSC lines toward endothelial cells.
Figure 7B:
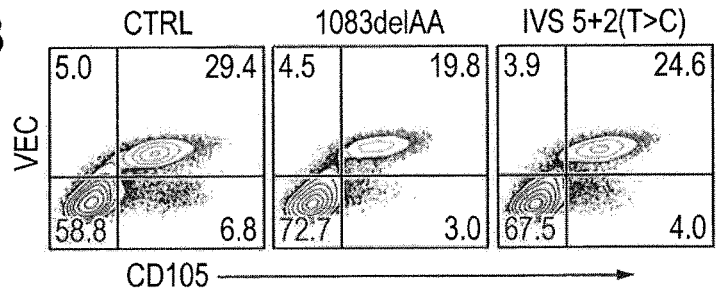
Figure 7C:
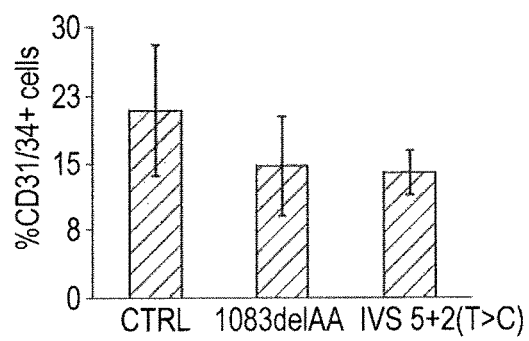
Figure 7D:
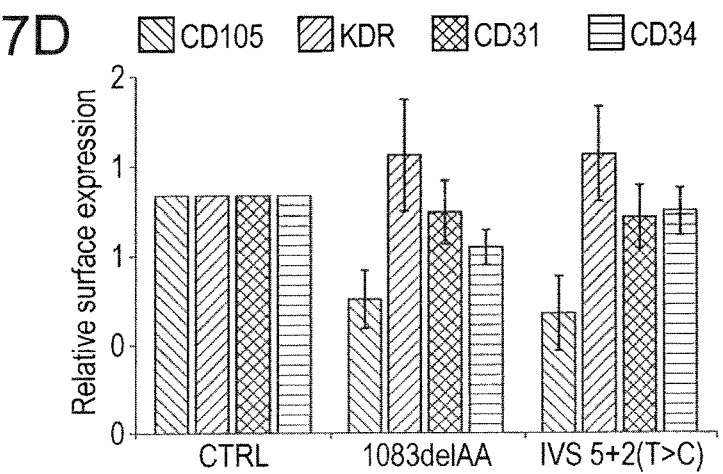
Figure 15A:
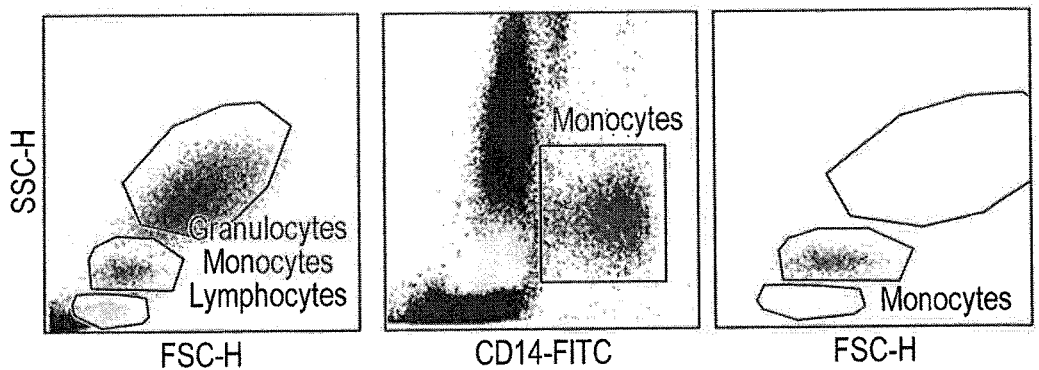
FIGS. 15A-15C: Characterization of ENG expression on HHT1 patient-derived PBMCs and HHT1-iPSC-derived ECs (CD31+). Flow cytometry analysis of control and HHT1 PBMCs.
Figure 15B:
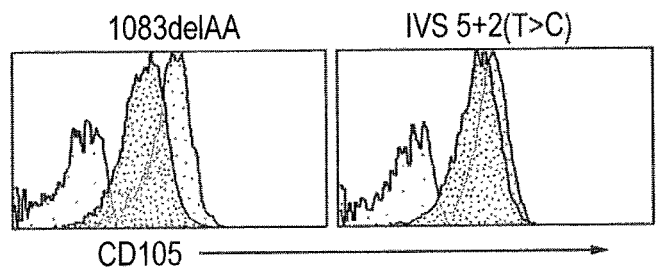
Figure 15C:
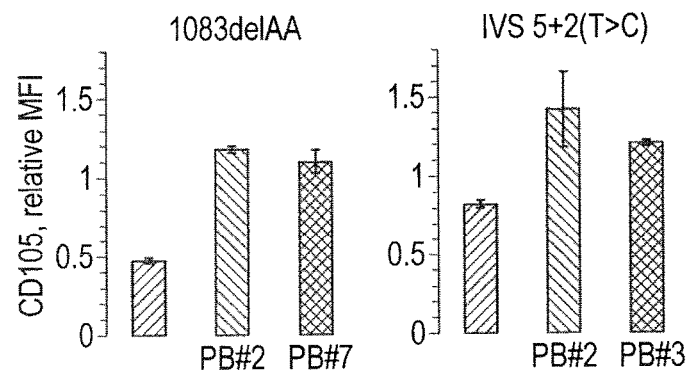
Figure 17B:
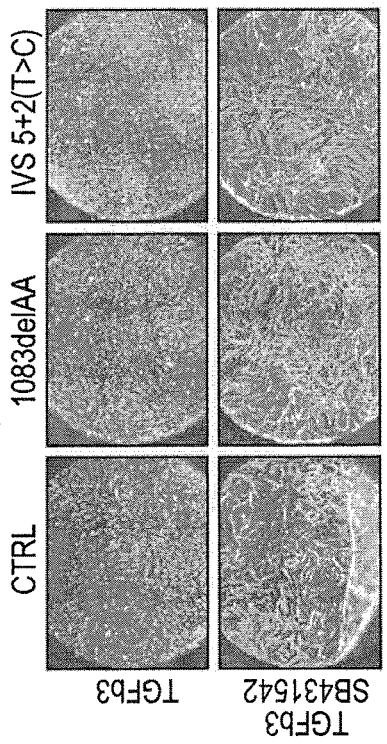
Figure 17D:
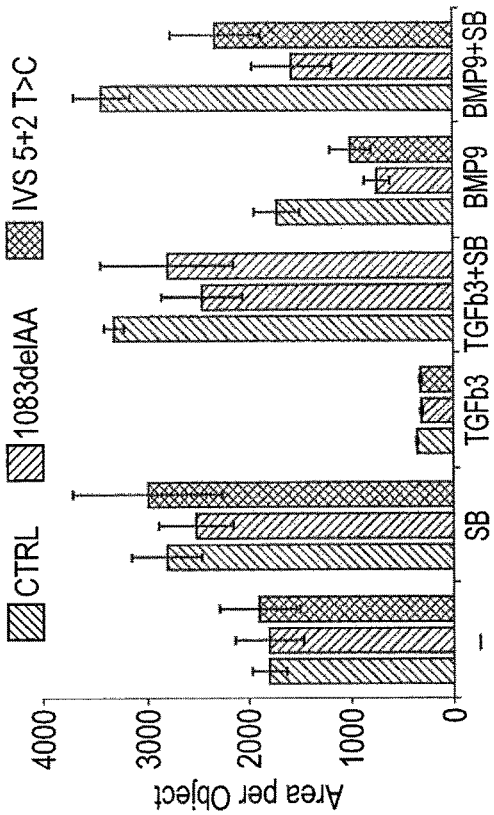
Figure 17A:
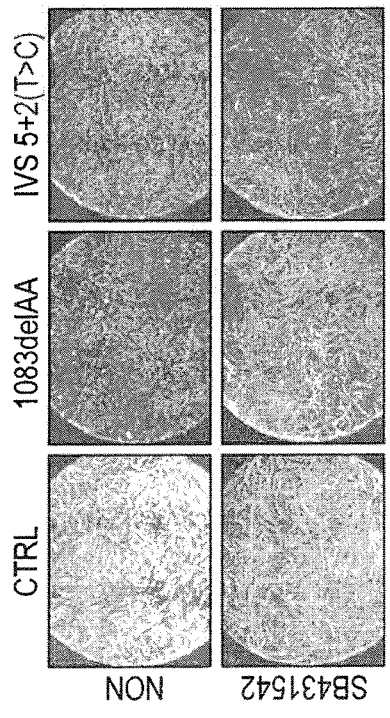
Figure 17C:
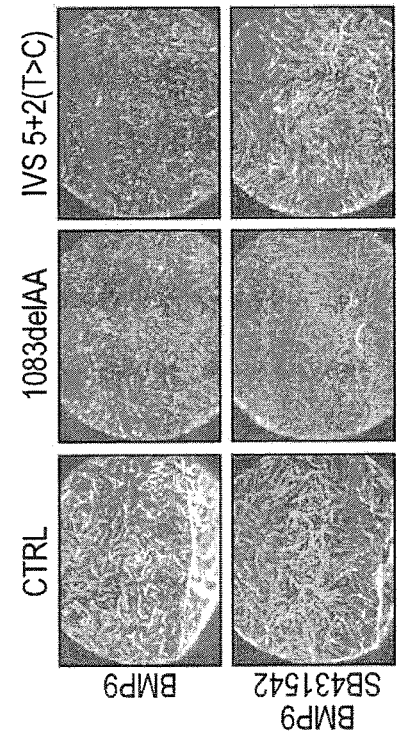
Figures 18B, 18C:
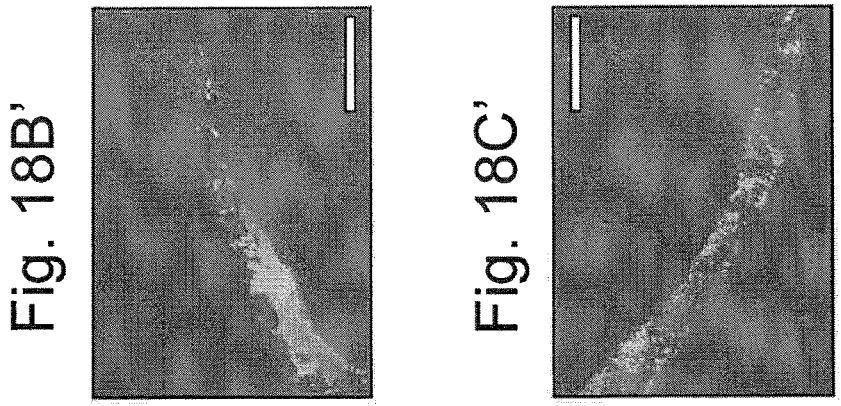
FIGS. 18A-18G: Vascular competence of hPSC-derived endothelial cells in zebrafish xenograft model.
Figures 18B, 18C:
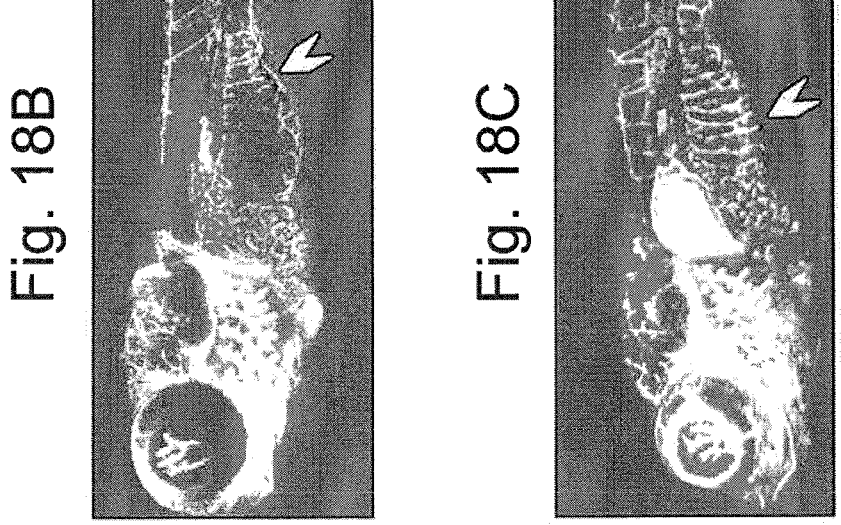
Figure 18A:
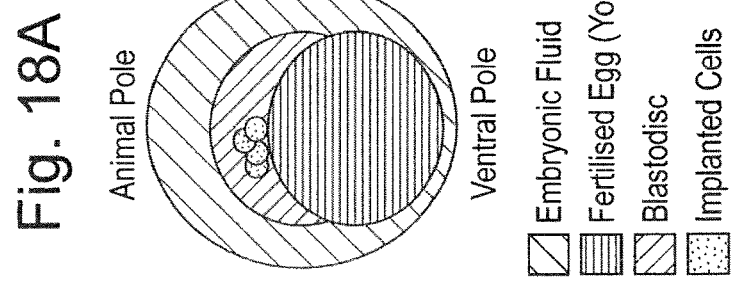
Figure 18D:
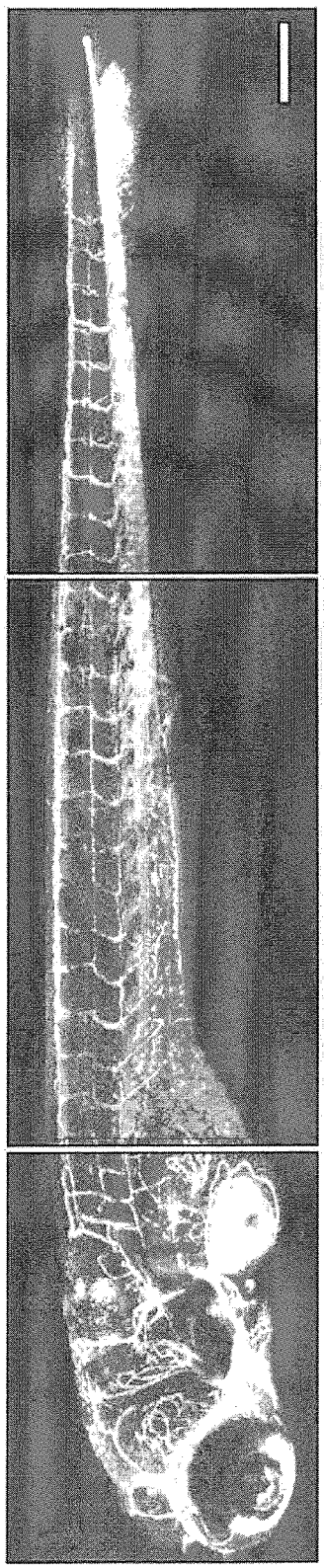
Figure 18E:
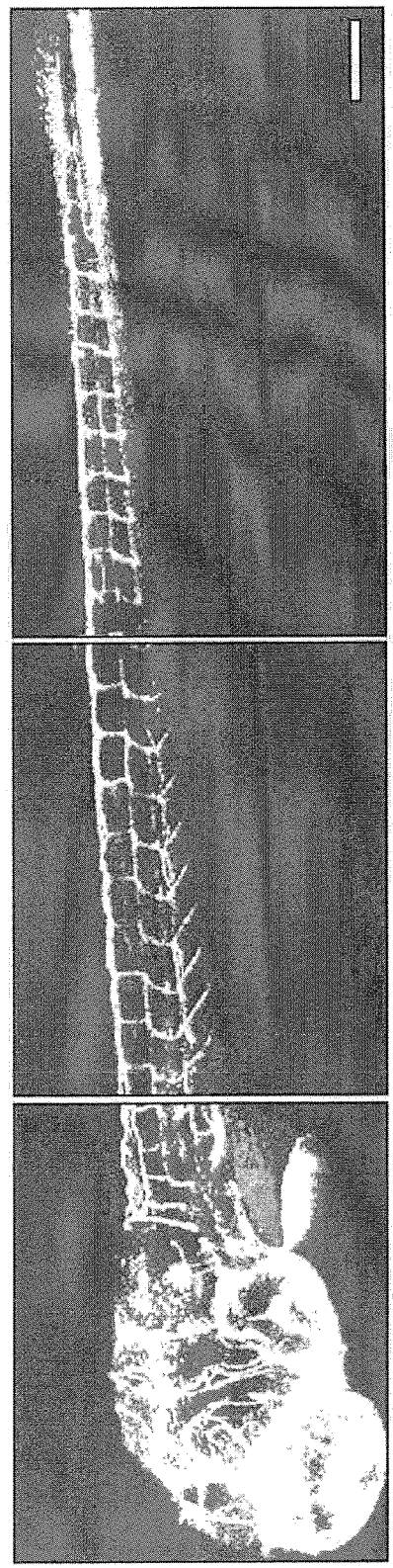
Figure 18F:
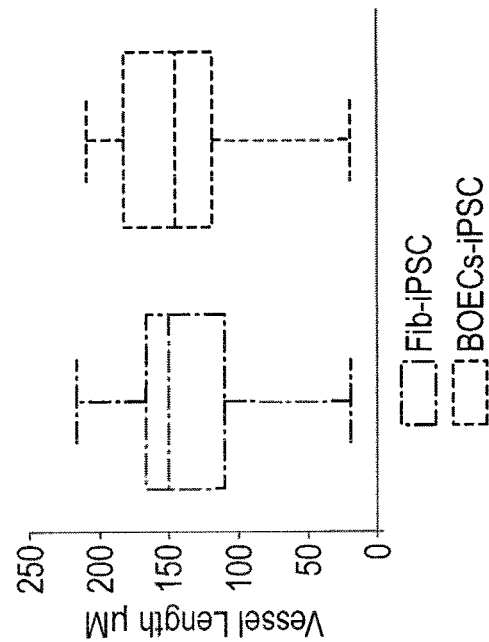
Figure 18G:
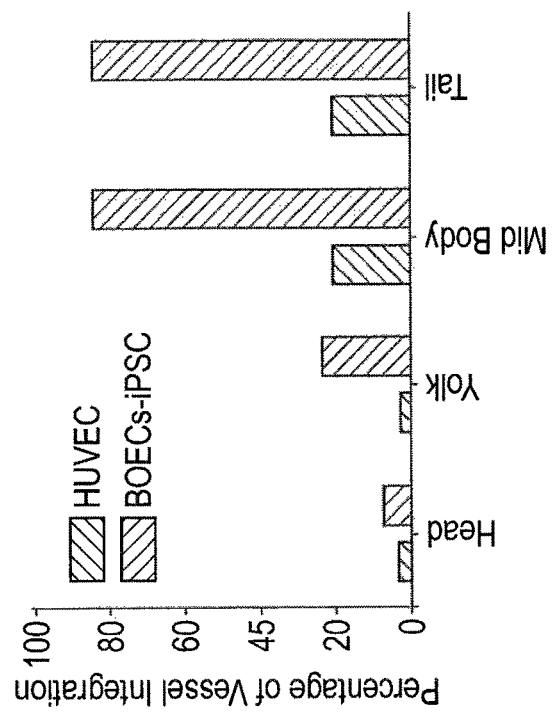

HHT1-iPSC lines were routinely maintained on MATRIGEL®-coated plates in mTeSR medium. To differentiate iPSCs into ECs, a serum-free, defined protocol recently developed in our lab was used, which yields ECs with typical endothelial characteristics at high efficiencies (Orlova et al, manuscript in preparation). These ECs can be both propagated and cryopreserved. Differentiating derivatives of control and disease iPSC lines were examined for the expression of EC-specific surface markers by flow cytometry at day 10 of differentiation. Differentiation resulted in robust induction (>20%) of ECs that expressed VE-Cadherin, CD31, CD34, and ENG (CD105) (FIGS. 7A and 7B). The majority of VE-Cadherin/CD31/CD34+ cells also expressed CD105. Also observed was a minor population of CD31-CD105+ mesenchymal progenitors among the CD105+ population (FIG. 7B). The relative surface expression of ENG in control- and HHT1-iPSC-derived ECs was next compared. Just as in peripheral blood monocytes (PBMCs) (FIG. 15A), ENG expression was significantly down-regulated in ECs from both the 1083delAA and IVS 5+2 T>C HHT1 patient iPSC lines (FIGS. 7D and 15B). By contrast, surface expression of other major EC surface markers such as CD31, CD34 and KDR was similar between lines (FIG. 7D). Endoglin deficiency had no effect on the total yield of ECs (FIG. 7C), in line with the previously published data using endoglin-deficient mouse embryonic stem cells in which even complete deletion had no effect on EC yield (Nomura-Kitabayashi et al., 2009).

Functional Characterization of HHT1-iPSC-Derived Endothelial Cells

Figure 8A:
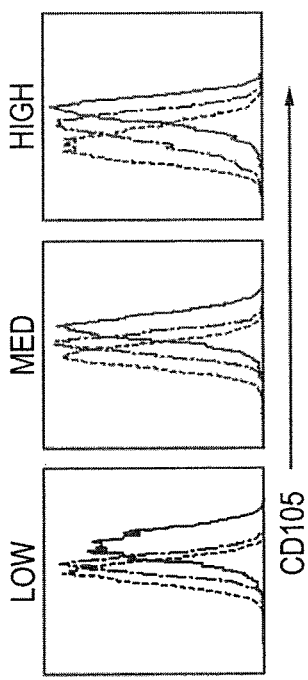
Figure 8B:
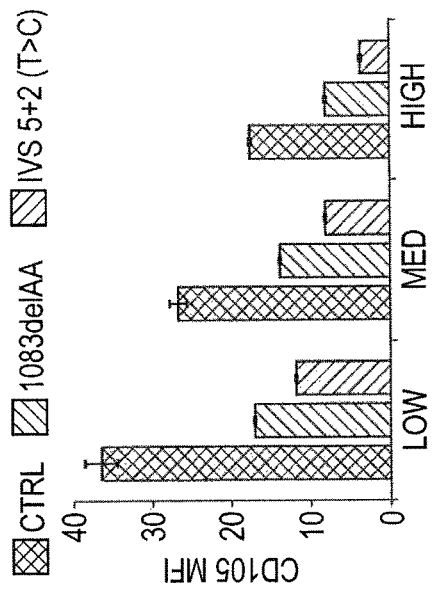
Figure 8C:
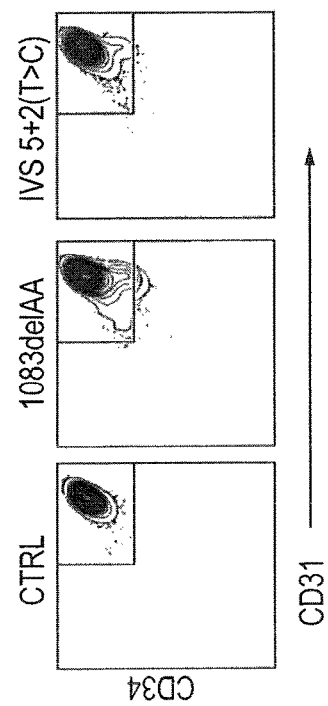
Figure 8D:
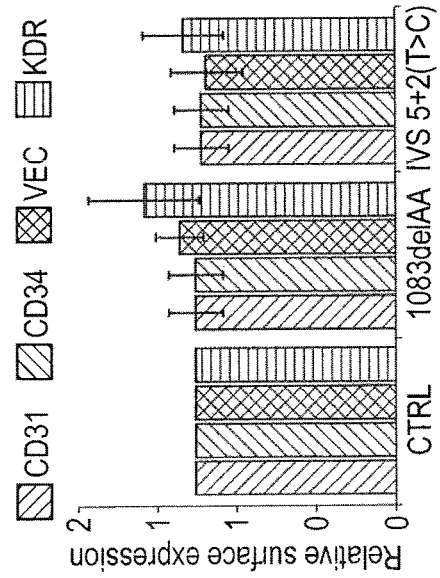

ECs were efficiently purified from mixed differentiated populations with the CD31 antibody coupled to magnetic beads. The yield and purity of cells were similar for control and HHT-iPSC lines (FIG. 8A). Purified ECs expressed comparable levels of CD31, CD34, VE-Cadherin and KDR as determine by flow cytometry analysis (FIG. 8B), as observed at day 10 of the differentiation in the de novo differentiated cells. ENG surface expression levels was next examined by flow cytometry. Endoglin surface expression was highly dependent on the cell density in culture and was up-regulated in ECs at low density, with the remarkable decline after cells reached confluence (FIGS. 8C and 8D). Similar patterns were found for HHT1-iPSC-derived ECs (as well as primary human umbilical vein endothelial cells (HUVECs), data not shown). It was then determined whether ENG was down-regulated in HHT1-iPSC-derived ECs that were expanded in vitro. As on ECs at day 10 of differentiation, strong reduction in expression in ECs was found with both the 1083delAA, and IVS 5+2 (T>C) mutations. This was independent of cell density although the strongest down-regulation was observed in highly confluent ECs and was less prominent in cells at low density. Immunofluorescent analysis revealed that both control and HHT1-iPSC-derived ECs formed homogeneous monolayers, with VE-Cadherin localized at the cell-cell junctions (FIG. 8E). ENG was again apparently reduced as demonstrated by IF. Western blot analysis confirmed major reduction of ENG expression levels for 1083delAA and IVS 5+2 T>C HHT1-iPSC-derived ECs (FIG. 8F).

Interestingly, since haplo-insufficiency is widely considered the underlying mechanism, ENG mRNA expression levels were also reduced as demonstrated by representative cDNA expression profiling experiment by real time PCR (FIG. 8G). In addition ALK1 expression levels were also down-regulated in HHT1-iPSC-derived ECs. However ALK5 expression levels were not affected, as well as CD31 and VE-Cadherin.

Figure 9A:
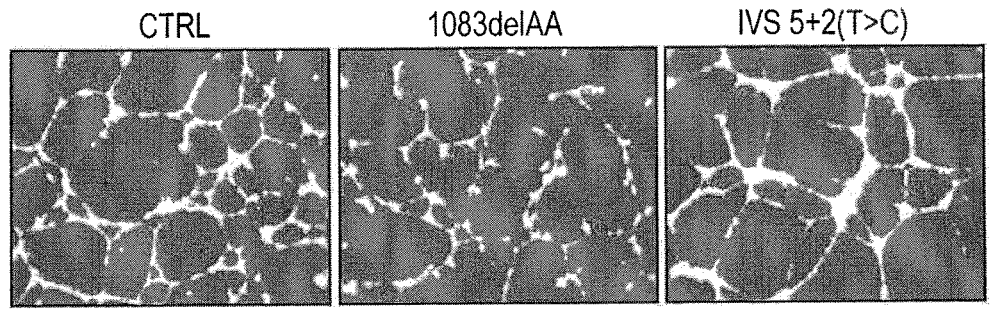
FIGS. 9A-9C: Functional characterization of HHT1 iPSC-derived ECs.
Figure 9B:
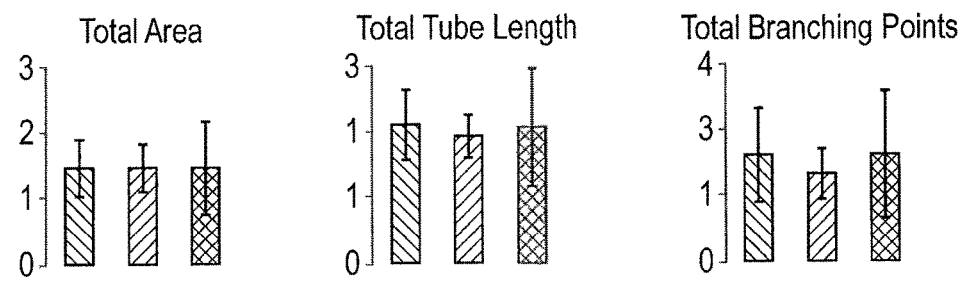
Figure 9C:
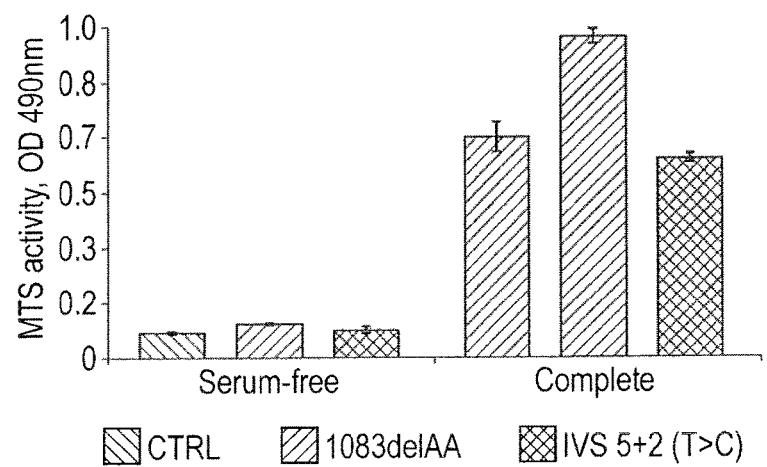

It was next examined whether functional competence was affected in HHT1-iPSC-derived ECs. ECs from control and HHT1-iPSC behaved similarly in the MATRIGEL® tube formation assay and no difference was observed in the total area, total tube length or number of branching points upon quantification in several independent experiments (N=4) (FIGS. 9A and 9B). TGFβ is also involved in EC proliferation (Orlova et al., 2011). Since TGFβ receptor abnormalities could affect cell proliferation, the proliferation rate of ECs from control and HHT1-iPSC lines was examined. Interestingly, higher proliferation rates in ECs were consistently observed from 1083delAA HHT1-iPSCs in the MTS assay than in control ECs (FIG. 9C).

HHT1-iPSC-Derived Endothelial Cells Exhibit Defective Endothelia-Pericyte Cell Interactions The 2D co-culture system can be also used to model endothelia-pericyte or vSMC cell interactions successfully. This is particularly important, since vSMC precursors that are derived from hPSC do not express contractile markers, such as SM22, etc. The up-regulation of vSMC markers can be induced upon either stimulation with TGFb (FIGS. 16A-16C), or induced via heterotypic cell-cell interactions with endothelial cells, much as has been shown during assembly of the vascular network in vivo. In this disclosure, additional evidence is included that the contractile state of vSMC in our system can be regulated upon co-culture with hPSC-derived ECs via heterotypic cell-cell interactions in a Notch dependent manner (FIGS. 23A-23C, addition to the FIGS. 12A-12C). It is important to mention that primary human vSMC precursors or pericytes do express SM22 in culture, and it is more difficult to use these cells in the co-culture system in order to study the effect of endothelial cells on the induction of the contractile markers by mural cells.

HHT1-iPSC-Derived Endothelial Cells Exhibit Defective Endothelial-Pericyte Interactions Defective endothelial-pericyte interactions have been proposed as one of the mechanisms underlying vascular abnormalities upon endoglin deficiency (Carvalho et al., 2004; Lebrin et al., 2010).

Our differentiation system facilitates simultaneous derivation and expansion of pericytes and ECs from iPSC lines. Plating the CD31− fraction resulted in the expansion of an homogenous population of cells that expressed pericyte and mesenchymal stem cell (MSCs) markers (PDGFRb, CD146, NG, CD73, CD44, CD105) (FIG. 16A). In addition, supplementation of medium with 10% FBS or FBS plus the growth factors TGFβ3 (1 ng/ml) and PDGF-BB (2 ng/ml) for 4 days resulted in up-regulation of contractile markers SM22 and Calponin (CNN1) as observed by immunofluorescent staining and real time PCR gene expression (FIGS. 16B and 16C). Thus, a renewable source of pericytes/SMCs was created for co-culture with ECs that would in principle be able to simulate endothelial-pericyte interaction in humans.

A two-dimensional co-culture system was first established in vitro consisting of control iPSC-derived ECs cultured with the control iPSC-derived mesenchymal cells (FIG. 10A). The protocol was optimized and adapted to the BD Pathway 855 imaging system, based on the protocol initially described for the co-culture of HUVECs and vascular SMCs (vSMCs) (Evensen et al., 2013). On day 7 of the co-culture, iPSC-derived EC had organized and formed spouts on the top mesenchymal cells, as evidenced by immunofluorescent staining with the EC-specific CD31 and SMC-specific SM22 markers (FIG. 10B).

Figure 10E:
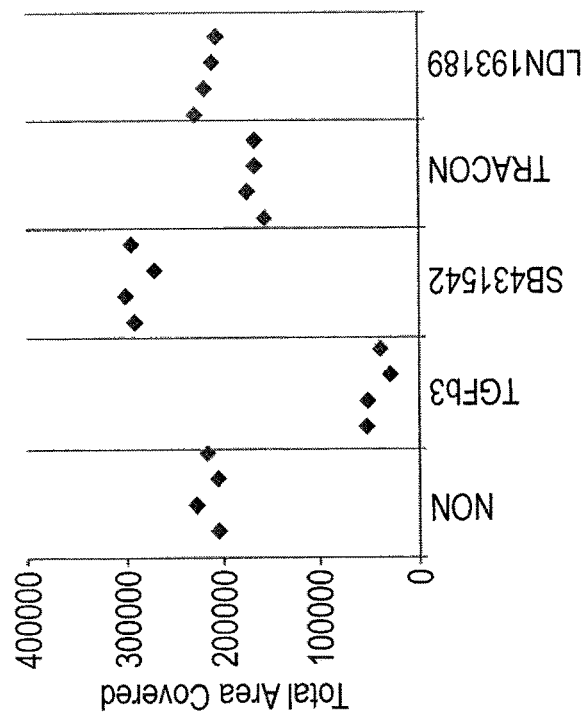
Figure 10D:
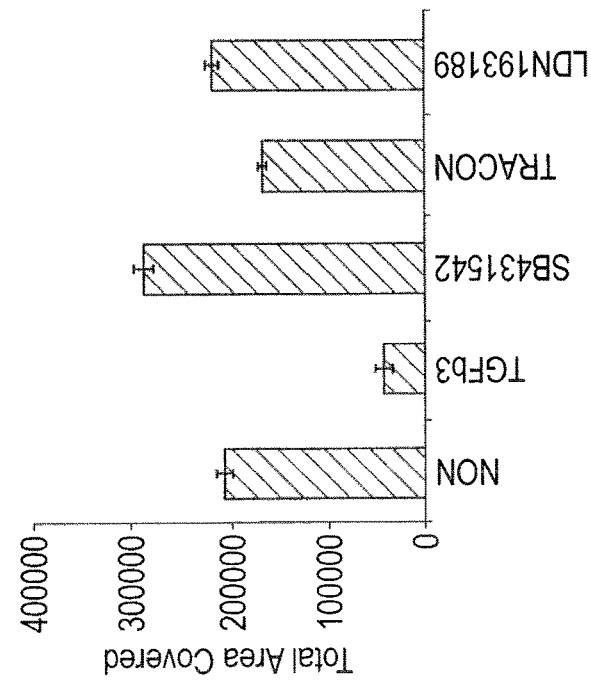

The TGFβ signaling pathway is indispensable for the formation of stable vasculature, as it is crucial for the regulation of endothelial cell and pericyte/vSMC function, and endothelial-pericyte interactions. Therefore, it was first determined which pathways were important in the formation of vascular sprouts in the co-cultures of control iPSC-derived ECs and control iPSC-derived mesenchymal cells. Addition of TGFβ3 (1 ng/ml) resulted in a dramatic reduction in the formation of the vascular sprouts, compared to the control condition (FIGS. 10C-10E). Inhibition of the ALK4/ALK5/ALK7 pathway with the small molecule (SB431542) resulted in the enhancement of sprout formation and an increase in the total area covered by endothelial sprouts. The effect of an anti-endoglin blocking antibody (TRC105, 120 μg/ml) in the iPSC-derived EC and pericyte co-cultures was next tested (Nolan-Stevaux et al., 2012; Seon et al., 2011; Shiozaki et al., 2006). The addition of TRC105 resulted in a reduction in the formation of the sprouts by ECs. However, inhibition of the ALK1/ALK2/ALK3 pathway with the LDN1931189 had no effect on sprout formation. Thus, our findings are in line with the previous work published in primary mouse ECs where TGFβ3-mediated Smad2/3 phosphorylation inhibited endothelial sprouting (Lebrin et al., 2004).

Figure 11A:
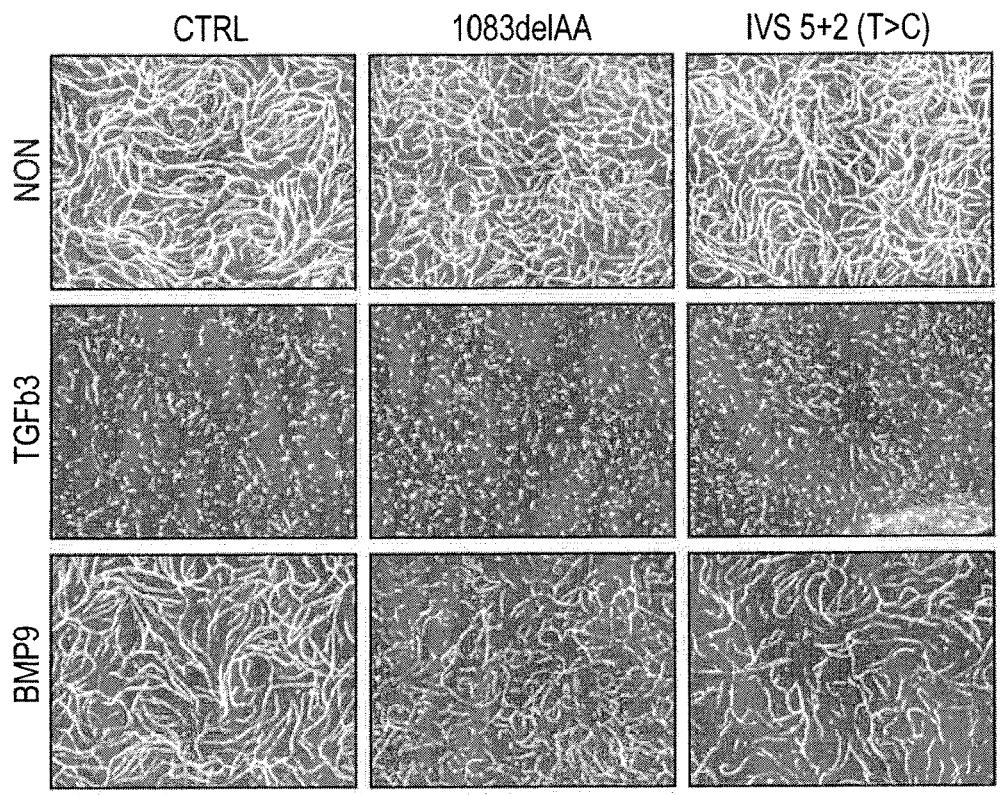
FIGS. 11A and 11B: Defective remodeling of HHT1 iPSC-derived endothelial cells in 2D-organotypic blood vessel systems comprising of iPSC-derived ECs co-cultured with hPSC-derived mural cells.
Figure 11B:
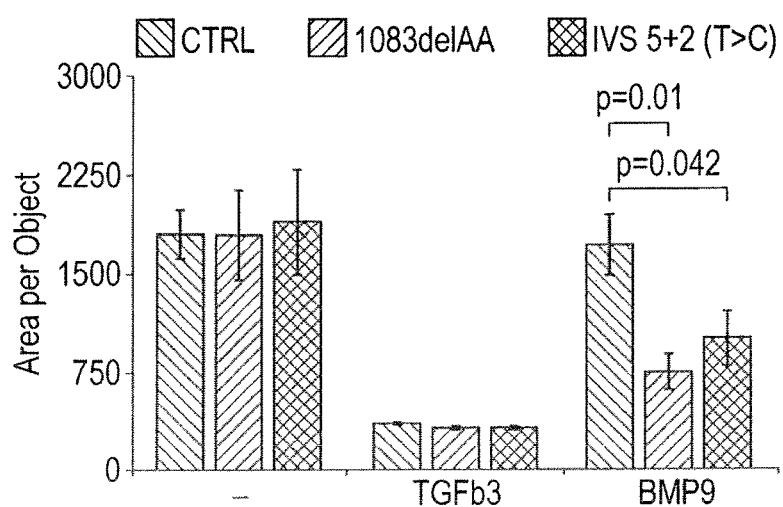

It was hypothesized that this system might be useful for distinguishing endocrine versus paracrine effects of endoglin deficiency in HHT1-iPSCs-derived ECs. Therefore, ECs from HHT-iPSC lines in the co-culture assay combined with the pericytes derived from the control iPSCs were examined. Little difference was observed between ECs from HHT1 and control iPSCs in co-culture. ECs from the patient harboring the 1083delAA and IVS 5+2 (T>C) mutation similar endothelial sprout formation as the controls (FIGS. 11A and 11B).

TGFβ has been shown to have dual effects in ECs and to induce both ALK5-mediated Smad2/3 and ALK1-mediated Smad1/5 phosphorylation (Goumans et al., 2002). Endoglin was demonstrated as being important for balancing TGFβ-mediated downstream signaling by shifting it toward ALK1-mediated Smad1/5 phosphorylation (Lebrin et al., 2004).

Therefore, it was examined as to whether or not ECs from HHT1-iPSC and control iPSC would exhibit differential responses toward TGFβ and BMP-9 in the co-culture system. Interestingly and consistent with the previous results with the control line (FIGS. 10C and 11A), addition of TGFβ (1 ng/ml) inhibited formation of the endothelial sprouts by HHT1 iPSC-derived ECs, as in controls. However, when the effect of BMP-9 (1 ng/ml) on the formation of the sprouting network was examined, significant inhibition was found in the HHT1-iPSC EC co-cultures, but no effect at all with ECs from the control iPSC (FIG. 10B). Strikingly, the addition of the ALK5 inhibitor (SB431542) rescued the inhibitory effect of both TGFβ3 and BMP-9 (FIGS. 17A-17F).

Figure 12A:
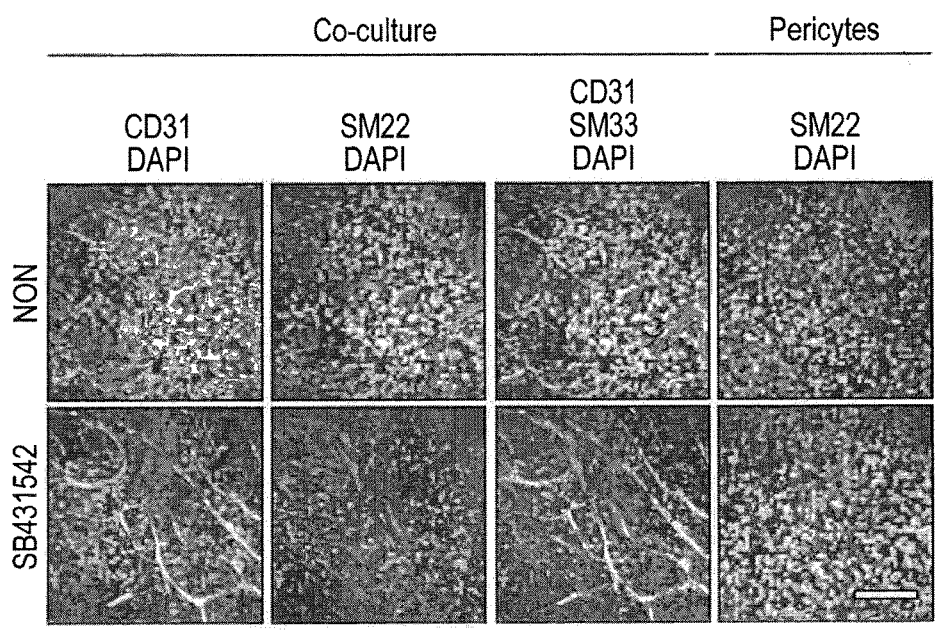
FIGS. 12A-12C: Defective endothelial-pericyte interactions.
Figure 12B:
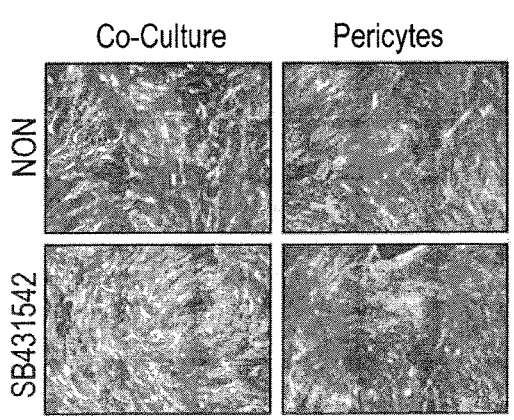
Figure 12C:
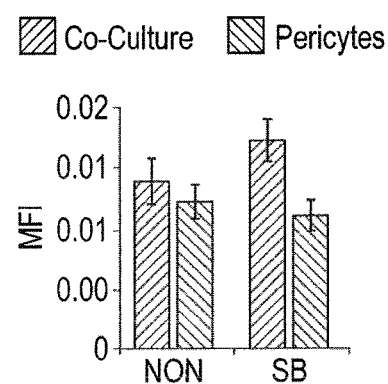

Endothelium-derived TGFβ is known to play an important role in promoting differentiation and acquisition of the contractile phenotype by mural cells. Previous work by our group demonstrated that defective endothelial-pericyte interaction is the major cause of the vascular abnormalities in endoglin-deficient mice (Carvalho et al., 2004; Lebrin et al., 2010). In addition, paracrine interactions between ECs and mural cells are more potent and can lead to induction of higher amounts of local biologically active TGFβ and lead to induction of mural cell differentiation (Carvalho et al, 2004; (Dina et al., 2004). Therefore, the effect of the endothelial-pericyte co-culture on the induction of the contractile smooth muscle marker SM22 was examined (FIGS. 12A-12C). Notably, supplementation with the ALK5 inhibitor resulted in an increase in SM22 fluorescence intensity, as observed by confocal imaging (FIG. 12A); this was confirmed by quantification (FIGS. 12B and 12C). Importantly, the ALK5 inhibitor had no effect on SM22 expression in pericytes. In addition, SM22 positive pericytes were localized close to the ECs sprouts. It appeared, therefore, that TGFβ/BMP9-mediated signaling is essential primarily for the ECs. Furthermore, ENG is required for the formation of endothelial networks, since ENG deficiency results in defective remodeling and sensitization of endothelium to anti-angiogenic property of BMP9 (Nolan-Stevaux et al., 2012; Scharpfenecker et al., 2007). In addition, ECs and heterotypic cell-cell interactions, but not TGFβ alone, are required for the maturation and recruitment of pericytes. In conclusion, ENG deficiency in ECs primarily affects EC remodeling and, as a consequence, results in defective endothelial-pericyte interactions.

Discussions

In the study described here, a novel system was developed to study the mechanisms underlying HHT using vascular derivatives from patient-specific HHT1-iPSC lines. Although mouse models, based on targeted deletion of endoglin, the gene causing HHT1, have been developed they do not fully recapitulate the disease phenotype in humans and the severity of the symptoms are highly dependent of the genetic background of the mice (Tang, 2003; Mao et al., 2006; Bourdeau et al., 1999; Benzinou et al., 2012; Bourdeau et al., 2001; Arthur et al., 2000). In addition, animal models often lack crucial aspects of human physiology, for example, the immune system, metabolism and drug responses which may make them unable to capture salient features of human disease (Seok et al., 2013; Kinnear et al., 2013). Over the last several decades, it has become possible to isolate certain primary cells from human tissue, although many are still relatively inaccessible for multiple reasons: highly invasive collection methods, rapid deterioration postmortem, small amounts of tissue, among others. Furthermore, the capacity of primary cells to remain viable and proliferate in vitro is limited, and typical phenotype is often rapidly lost. This is particularly relevant to the primary endothelium, which can be expanded to some extent in culture but do not maintain their characteristic phenotype. Since endothelial dysfunction has been linked to multiple genetic and non-genetic cardiovascular diseases, in vitro systems that (i) recapitulate disease phenotypes (ii) can be scaled up to produce multiple identical replicates and (iii) have an easily quantifiable readout of phenotype, are potentially of great importance for drug and compound screening in the search for therapies.

iPSC technology is presently among the most promising options in the generation of human models for drug discovery since it allows the generation of unlimited numbers of human somatic cells of different types that exhibit typical human features (Bellin et al., 2012). The technology herein disclosed was used to produce iPSCs from HHT1 patients. In addition, highly efficient methods were developed that facilitate the isolation of both endothelial and perivascular cells that harbor the same mutations as patients. It was demonstrated that the iPSC-derived ECs can be expanded efficiently in vitro with preservation of primary features of ECs, such as expression of typical EC markers, formation of confluent monolayers with VE-Cadherin localized at cell-cell junctions, and responsiveness toward VEGF and bFGF. In addition, HHT1-iPSC-derived ECs retained the reduced ENG expression levels as observed in PBMCs from patients showing that reprogramming as such had not affected the aberrant expression of the mutant gene. Extensive characterization of HHT1-iPSC-derived ECs did not reveal any differences in EC yield from optimized differentiation protocols, or functionality compared to control iPSC-derived ECs. In addition, TGFβ/BMP9-mediated downstream signaling was retained (data not shown). This is in line with previous studies demonstrating a role of ENG in mediating heterotypic, and not homotypic, cell-cell interactions, as found in mice (Carvalho et al., 2004; Lebrin et al., 2010). To investigate whether this was also the case for human disease endothelium, a co-culture system of ECs and pericytes was established based on protocol described previously using HUVEC and primary human fibroblasts (Evensen et al., 2013). In contrast to HUVEC based assays however, the system based on iPSC-derived ECs and pericytes, was highly sensitive to TGFβ, and supplementation with the ALK5 inhibitor resulted in significant increase in number of endothelial sprouts, as well as the culture surface area covered by ECs, as demonstrated previously for mouse ESC-derived ECs (Watabe et al., 2003). This likely reflected the more "embryonic" status of iPSC-derived ECs, as TGFβ-mediated growth inhibition is a property typical of embryonic ECs (Watabe et al., 2006; 2003; James et al., 2010). Active remodeling of endothelium that occurs during inflammation or tumor angiogenesis has been also associated with increased responsiveness of ECs toward TGFβ (Kano et al., 2007) so that the system could well serve as a model for tumor angiogenesis. Of note in this context, the anti-ENG antibody, Tracon (TRC105), currently in clinical trial as an anti-tumor therapy because of its ability to inhibit vascular invasion of tumors and thus their nutrient supply, significantly reduced sprouting and the surface area covered by ECs in the co-culture assay (Nolan-Stevaux et al., 2012; Seon et al., 2011; Shiozaki et al., 2006). This could indicate a more general utility of the system in screening for other anti-tumor compounds that act by reducing tumor angiogenesis.

Inflammation has been proposed previously as a possible trigger for the onset of HHT (Mahmoud et al., 2010) and ENG is known to be expressed in blood vessels that undergo active remodeling (Arthur et al., 2000). ENG deficiency might result in defective remodeling and formation of defective blood vessels with inflammation as an intrinsic part of the mechanisms.

Taking in account that ENG is expressed primarily in endothelial cells and not pericytes/mesenchymal cells in mouse and human in vivo (unpublished observations), it was hypothesized that a co-culture system might be particularly useful in dissecting the effect of ENG deficiency on ECs. Therefore, HHT1-iPSC-derived ECs with pericytes derived from the control iPSCs mimicking EC-pericyte interaction were combined in the vessels of HHT1 patients. HHT1-iPSC-derived ECs remodeled normally under control conditions. TGFβ inhibited endothelial network formation in both control and HHT1-iPSc ECs to the similar extent. Strikingly, however, there was a selective inhibitory effect of BMP9 in the HHT1-iPSC-derived EC co-cultures but not with ECs from the control line. BMP9 was recently identified as a circulating vascular quiescence factor (Bidart et al., 2011; David et al., 2008). ENG was shown to potentiate binding of BMP9 to ALK1 and Smad1/5-mediated signaling (Nolan-Stevaux et al., 2012). Interestingly, inhibition of Smad1/5 had no effect on the formation of the sprouting network in our system. Our system revealed the role of ENG in BMP9-mediated downstream signaling in iPSC-derived ECs. Importantly, it was found that BMP9 had specific inhibitory responses during sprouting of HHT1-iPSC-derived ECs but not in control iPSC-derived ECs. Thus, ENG deficiency in ECs of HHT1 patients possibly leads to defective remodeling because of increased anti-angiogenic and growth inhibitory responses. This could contribute to the exceptionally fragile vessels of HHT patients, which lead to their chronic tendency to hemorrhage. Compounds that rescue the phenotype in our co-culture assay may be candidate lead compounds for drug development. In a broader context, vascular diseases that affect either pericytes or ECs or both could be modeled in the iPSC coc-culture system described herein.

Experimental Procedures hESC and iPSC Lines iPSC lines were derived from control individuals (LUMC004iCTLR, LUMC006iCTRL) or HHT1 patients carrying the following ENG mutations (FIG. 1A): LUMC08iENG (exon 8, 1083delAA), LUMC009iENG (exon 5, IVS 5+2 (T>C). Depending on the availability of donor tissue, fibroblasts (LUMC04iCTRL, LUMC08iENG) or blood outgrowth endothelial cells (BOECs, LUMC06iCTRL, LUMC09iENG) from skin biopsies or peripheral blood, respectively, were used for reprogramming. Somatic cells were isolated as described previously (Dambrot et al. 2013). Lentiviral transduction vectors encoding the four Yamanaka factors OCT4, SOX2, KLF4 and c-Myc were used for reprogramming. Lentiviruses were produced in HEK293FT cells under standard conditions. Reprogramming fibroblasts or BOECs with a self-inactivating polycistronic lentivirus encoding the four Yamanaka factors and d-Tomato as a reporter (kindly provided by C. Baum) was done as described previously (Dambrot et al., 2013). After viral transduction somatic cells were seeded on mouse embryonic fibroblasts (MEFs) and cultured in hESC KOSR Medium (Dulbecco's Modified Eagle Media (DMEM)/F12 supplemented with Glutamax, 10 mM NEAA, 25 U/ml penicillin, 25 µg/ml streptomycin, 100 µM β-mercaptoethanol, 20% knockout serum replacement (KOSR; all Invitrogen) and 10 ng/ml basic FGF (PreproTech)) until the appearance of hESC-like colonies. After picking, iPSCs were cultured on MATRIGEL® (BD) in mTESR1 (Stem Cell Technologies) according to the manufacturer's protocol.

Spontaneous Differentiation of iPSCs in Vitro for Assessing Developmental Potency After passaging, iPSCs were cultured on MATRIGEL® in TESR1 for two days. Subsequently cells were cultured in DMEM/F12 supplemented with 20% FCS for three weeks during which differentiation took place. The medium was changed every other day. For immunofluorescent staining, cells were fixed with 2% PFA for 30 minutes at room temperature.

Immunofluorescent Staining

Undifferentiated or spontaneously differentiated iPSCs were stained according to standard procedures. Briefly fixed cells were permeabilized with Triton X-100, blocked with 4% normal swine serum for 1 hour at room temperature before overnight incubation at 4° C. with the primary antibody (SSEA-4 (1:30, Biolegend), OCT3/4 (1:100, Santa Cruz), Nanog (1:40, R&D), TRA-1-81 (1:125, Biolegend), βIII-tubulin (1:2000, Covance), AFP (1:25, Quartett), SMA (1:200, Sigma)). Secondary antibodies labelled with Cy3 (1:250, Jackson Immuno Research) or Alexa 488 (1:250, Invitrogen) was added for 1 hour at room temperature. DAPI was used for staining nuclei before mounting slides with Mowiol (Calbiochem).

Differentiation of iPSCs to Endothelial Cells and Magnetic Bead Purification

Differentiation of iPSCs to ECs was performed as described elsewhere (Orlova et al., manuscript submitted). iPSCs lines were passaged on growth factor reduced MATRIGEL®-coated plates (BD). Differentiation was induced on day 3 after passaging. Briefly defined media consisting of BPEL (Ng et al., 2008) with additional human recombinant BMP4 (30 ng/ml, Miltenyi), Activin (25 ng/ml, Miltenyi), VEGF (50 ng/ml, R&D) and CHIR99021 (1.5 µM, Tocris) was added for 3 days in order to induce mesoderm. Medium was additionally refreshed with BPEL with VEGF (50 ng/ml) and SB43152 (5 µM, Tocris) at day 3 and day 7 of differentiation. ECs were purified with CD31 coupled magnetic beads (Life Technologies) and culture further scaled up on 1% gelatin coated tissue culture flasks in human endothelial serum free media (EC-SFM) (Life Technologies) with additional VEGF (30 ng/ml), bFGF (20 ng/ml, R&D) and platelet low bovine extract (1%, BIT). ECs were routinely maintained up to passage 5, and functional assays were performed on cell between passages 2-3.

Differentiation of iPSCs Toward Pericytes/Mesenchymal Cells iPSC-derived pericytes/mesenchymal cells were derived from the CD31− fraction emerging during the endothelial differentiation protocol. CD31− cells were plated on gelatin coated plates in EGM-2 media (Lonza). After 4 days medium was replaced by DMEM+10% FBS supplemented with TGFβ3 (2 ng/ml, Peprotech) and PDGF-BB (4 ng/ml, Peprotech). iPSC-derived pericytes were routinely maintained on gelatin-coated plates in DMEM+10% FBS. Cells were characterized for the expression of pericyte and mesenchymal cell-specific markers by flow cytometry and immunofluorescent staining as describe above.

Flow Cytometry

Fluorescence-activated cell sorting (FACs) analysis was performed as described (Orlova et al., Manuscript submitted). Briefly, day 10 differentiating cultures or purified ECs were dissociated gently with TrypLE Select (Life Technologies). Combinations of the following antibodies were used in flow cytometry experiments: VE-Cadherin-A488 (1:100, eBiosciences), CD31-APC (1:200, eBiosciences), CD34-PerCP-Cy5.5 (1:100, BD Pharmingen), KDR-PE (1:50, R&D Systems), PDGFRb-PE (1:50, BD Pharmingen), CD73-PE (1:50, BD Pharmingen), CD105 A488 (1:200, Life Technologies), NG2 (1:50, R&D), CD146-PE (1:50, BD), CD44-FITC (1:50, Biolegend). Samples were analyzed on LSRII (BD) with the following instrument setup: Blue/488 FITC, A488: 505LP-530/30, PerCP-Cy5.5: 630LP-670/14; Yellow/561 PE: 570LP-582/15, APC: 635LP-660/20; or MACSQuant VYB (Miltenyi).

Whole Blood Flow Cytometry Analysis

Whole blood was collected into sodium citrate blue top tubes (Vacutainer, BD) and processed immediately the same day or was stored at room temperature with the gentle agitation and processed the next day. Whole blood staining protocol was performed at described before (Altman Lab, Emory) with the slight modification. Whole blood (100 µl) was blocked with the human FC-block (5 µl, Miltenyi) for 5 minutes at the room temperature. Antibodies were added directly to the whole blood samples for additional 10 minutes. Combination of the following antibodies was used: CD14-FITC (1:200, BD), CD105-PE (1:200, Life Technologies). Red blood cells were lysed with the FACS lysing solution (2 ml, BD) for 10 minutes at RT. Samples were washed once with the FACs buffet, and fixed with 1% PFA. Analysis was performed on LSRII with the instrumental setting as described above.

Immunofluorescent Staining for Endothelial and Pericyte Cell Markers

ECs and pericytes were cultured as described above on gelatin coated coverslips. Cells were fixed with 4% PFA, permeabilized and stained with the following antibodies as described (Orlova et al., Manuscript in preparation): anti-Ve-Cadherin (1:200, CellSignaling), anti-vWF (1:200, Dako), anti-CD31 (1:200, Dako), anti-SM22a (1:200, Abcam), anti-SMA (1:400, Sigma), anti-CNN1 (1:200, Sigma).

Western Blot Analysis

Cell lysates were prepared according to the standard protocol in RIPA buffer and protein concentration was determined by DC protein assay (Biorad). Protein were separated in 10% SDS-PAGE and transferred to nitrocellulose membranes Hybond-C Extra (Amersham Biosciences). Membrane was blocked with 5% milk powder in TRIS-Buffered Saline (TBS) containing 0.05% TWEEN®-20 (Merck). Blotting membranes were incubated with the following primary antibodies: mouse anti-β-actin (1:5000, Sigma-Aldrich), goat anti-ENG (1:1000, R&D), rabbit anti-PECAM1 (1:500, Santa Cruz), and HRP-conjugated secondary antibodies anti-rabbit IgG (1:5000, CellSignaling), anti-goat IgG (1:5000, Santa Cruz) and anti-mouse IgG (1:10000, CellSignaling). ECL Western blot detection reagent was used to detect the chemiluminescence according to the manufactures protocol (Pierce).

Gene Expression Analysis of HHT1-iPSC-Derived Endothelial Cells iPSC-derived ECs were cultured in EC-SFM medium for 6 hours and stimulated with 1 ng/ml BMP9 (R&D) and 1 ng/ml TGFβ3 (Peprotech) for an additional 4 hours. Total RNA, cDNA and real-time PCR (SYBR green based detection system) were performed according to the standard procedure. Relative gene expression was determined according to the standard delta Ct calculation, with the acidic ribosomal protein (hARP) being used as a housekeeping gene. Primer sequences are listed in Table S1.

MATRIGEL® Tube Formation Assay iPSC-derived ECs were pre-labelled with the green fluorescent general cytoplasmic agent (PKH67, sigma) and seeded on growth factor reduced MATRIGEL® according to the standard procedure with the slight modifications (Orlova et al., Manuscript). Tube formation was monitored over a period of time, and end point images were acquired at 24 hours with the BD Pathway 855 system (4× objective and 2×2 montage mode). Quantification of the total area occupied, total tube length and branching points were performed with Wimasis imaging software (on the World Wide Web at wimasis.com).

Endothelial Cell Proliferation iPSC-derived ECs were plated in fibronectin (FN, 2 µg/ml, Sigma) coated 96-well plates (2,000 cells/well) and 12 hours after plating the media was replaced with the EC-SFM containing different stimuli. The assay was stopped after 96 hours, and relative EC number determined using the MTS assay (CellTiter, Promega).

Endothelial Cell-Pericyte Co-Culture

Endothelial cell-pericyte co-culture was performed as described previously (Evensen et al., 2013) but using conditions optimized for iPSC-derived ECs and pericytes as described (Orlova et al., manuscript in preparation). In brief, 12,000 and 50,000 iPSC-derived ECs and pericytes were plated, respectively, in each well of a 96-well plate. Next day the co-cultures were refreshed with the specific treatment conditions indicated. The co-culture was fixed on day 7, and EC sprouts stained with anti-CD31 antibody (1:200, Dako) (as described in Orlova et al., manuscript in preparation). Pericytes were visualized with the anti-SM22 antibody (1:200, Abcam). The BD Pathway 855 system was used for automatic image acquisition, with the 4× objective and 2×2 (or in some cases 3×3) montage mode. CellProfiller (Broad Institute) custom pipeline was used for the image quantification. Z-factor calculation was performed as described and resulted in the value 0.493 (>0.4) based on the approximation that the TGFβ3 condition was determined as a minimum and the SB condition as a maximum (Evensen et al., 2013).

TABLE

| Gene | Forward primer 5'-3' | Reverse primer 5'-3' |
| --- | --- | --- |
| hARP | CACCATTGAAATCCTGAGTGATGT (SEQ ID NO: 1) | TGACCAGCCCAAAGGAGAAG (SEQ ID NO: 2) |
| Oct4 | ACGACCATCTGCCGCTTTG (SEQ ID NO: 3) | GCTTCCTCCACCCACTTCTG (SEQ ID NO: 4) |
| Nanog | GCCGAAGAATAGCAATGGTG (SEQ ID NO: 5) | TGGTGGTAGGAAGAGTAGAGG (SEQ ID NO: 6) |

TABLE-continued

| Gene | Forward primer 5'-3' | Reverse primer 5'-3' |
|---|---|---|
| T | ATCACCAGCCACTGCTTC (SEQ ID NO: 7) | GGGTTCCTCCATCATCTCTT (SEQ ID NO: 8) |
| KDR | CCATCTCAATGTGGTCAACCTTCT (SEQ ID NO: 9) | TCCTCAGGTAAGTGGACAGGTTTC (SEQ ID NO: 10) |
| PDGFRa | ATTGCGGAATAACATCGGAG (SEQ ID NO: 11) | GCTCAGCCCTGTGAGAAGAC (SEQ ID NO: 12) |
| ETV2 | CAGCTCTCACCGTTTGCTC (SEQ ID NO: 13) | AGGAACTGCCACAGCTGAAT (SEQ ID NO: 14) |
| ALK1 | CTGGTTCCGGGAGACTGAGAT (SEQ ID NO: 15) | TGCGGGAGGTCATGTCTGA (SEQ ID NO: 16) |
| PECAM1 | GCATCGTGGTCAACATAACAGAA (SEQ ID NO: 17) | GATGGAGCAGGACAGGTTCAG (SEQ ID NO: 18) |
| ENG | CCCGCACCGATCCAGACCACTCCT (SEQ ID NO: 19) | TGTCACCCCTGTCCTCTGCCTCAC (SEQ ID NO: 20) |
| PDGFRb | ACGGAGAGTGTGAATGACCA (SEQ ID NO: 21) | GATGCAGCTCAGCAAATTGT (SEQ ID NO: 22) |
| CD146 | CTGCTGAGTGAACCACAGGA (SEQ ID NO: 23) | TCAGGTCATGCAACTGAAGC (SEQ ID NO: 24) |
| NG2 | CCAGGAAAGGCAACCTTCAAC (SEQ ID NO: 25) | ACGGAAACGGAAGGTGTCC (SEQ ID NO: 26) |
| VEC | GGCATCATCAAGCCCATGAA (SEQ ID NO: 27) | TCATGTATCGGAGGTCGATGGT (SEQ ID NO: 28) |
| Lyve1 | CACAAGGGTGATCCCCATAA (SEQ ID NO: 29) | GCCTGGTGTTGCTTCTCACT (SEQ ID NO: 30) |
| VEGFR3 | CTGTGCCTGCGACTGTG (SEQ ID NO: 31) | GGTGTCGATGACGTGTGACT (SEQ ID NO: 32) |
| EphrinB2 | GAAGTACGAGCCCCACAGA (SEQ ID NO: 33) | CCCAACGCAGAAATAAACG (SEQ ID NO: 34) |
| EphrinB4 | GAAAAGGAAGTGCCCAACA (SEQ ID NO: 35) | CTGGCAAGGGAGTCACACT (SEQ ID NO: 36) |
| NRP1 | AACACCAACCCCACAGATG (SEQ ID NO: 37) | AAGTTGCAGGCTTGATTCG (SEQ ID NO: 38) |
| NRP2 | CTGGAAGCAGCATTGTGTG (SEQ ID NO: 39) | TAACTCGCTGATGGGGAGA (SEQ ID NO: 40) |
| CoupTFII | GCTTTCCACATGGGCTACAT (SEQ ID NO: 41) | CAAGTGGAGAAGCTCAAGGC (SEQ ID NO: 42) |
| Hey2 | TCATGAAGTCCATGGCAAGA (SEQ ID NO: 43) | TTGTGCCAACTGCTTTTGAA (SEQ ID NO: 44) |

REFERENCES

Aird, W. C. 2007. Phenotypic heterogeneity of the endothelium: II. Representative vascular beds. *Circ. Res.* 100: 174-190. doi:10.1161/01.RES.0000255690.03436.ae.

Aird, W. C. 2012. Endothelial Cell Heterogeneity. *Cold Spring Harb Perspect Med.* 2:a006429-a006429. doi: 10.1101/cshperspect.a006429.

Akhurst, R. J., and A. Hata. 2012. Targeting the TGFβ signalling pathway in disease. *Nat Rev Drug Discov.* 11:790-811. doi:10.1038/nrd3810.

Amit, M., M. K. Carpenter, M. S. Inokuma, C. P. Chiu, C. P. Harris, M. A. Waknitz, J. Itskovitz-Eldor, and J. A. Thomson. 2000. Clonally derived human embryonic stem cell lines maintain pluripotency and proliferative potential for prolonged periods of culture. *Dev. Biol.* 227:271-278. doi:10.1006/dbio.2000.9912.

Arnaoutova, I., and H. K. Kleinman. 2010. In vitro angiogenesis: endothelial cell tube formation on gelled basement membrane extract. *Nat Protoc.* 5:628-635. doi: 10.1038/nprot.2010.6.

Arthur, H. M., J. Ure, A. J. H. Smith, G. Renforth, D. I. Wilson, E. Torsney, R. Charlton, D. V. Parums, T. Jowett, D. A. Marchuk, J. Burn, and A. G. Diamond. 2000. Endoglin, an Ancillary TGFβ Receptor, Is Required for Extraembryonic Angiogenesis and Plays a Key Role in Heart Development. *Dev. Biol.* 217:42-53. doi:10.1006/dbio.1999.9534.

Begbie, M. E., G. M. F. Wallace, and C. L. Shovlin. 2003. Hereditary haemorrhagic telangiectasia (Osler-Weber-Rendu syndrome): a view from the 21st century. *Postgrad Med J.* 79:18-24.

Bellin, M., M. C. Marchetto, F. H. Gage, and C. L. Mummery. 2012. Induced pluripotent stem cells: the new patient? *Nat. Rev. Mol. Cell Biol.* 13:713-726. doi: 10.1038/nrm3448.

Benedito, R., S. F. Rocha, M. Woeste, M. Zamykal, F. Radtke, O. Casanovas, A. Duarte, B. Pytowski, and R. H. Adams. 2012. Notch-dependent VEGFR3 up-regulation allows angiogenesis without VEGF-VEGFR2 signalling. *Nature.* 484:110-114. doi:10.1038/nature10908.

Benzinou, M., F. F. Clermont, T. G. W. Letteboer, J.-H. Kim, S. Espejel, K. A. Harradine, J. Arbelaez, M. T. Luu, R. Roy, D. Quigley, M. N. Higgins, M. Zaid, B. E. Aouizerat, J. K. P. van Amstel, S. Giraud, S. Dupuis-Girod, G. Lesca, H. Plauchu, C. C. W. Hughes, C. J. J. Westermann, and R. J. Akhurst. 2012. Mouse and human strategies identify PTPN14 as a modifier of angiogenesis and hereditary haemorrhagic telangiectasia. *Nat Commun.* 3:616. doi: 10.1038/ncomms1633.

Bidart, M., N. Ricard, S. Levet, M. Samson, C. Mallet, L. David, M. Subileau, E. Tillet, J.-J. Feige, and S. Bailly. 2011. BMP9 is produced by hepatocytes and circulates mainly in an active mature form complexed to its prodomain. *Cell. Mol. Life Sci.* 69:313-324. doi:10.1007/s00018-011-0751-1.

Bose, P., J. L. Holter, and G. B. Selby. 2009. Bevacizumab in Hereditary Hemorrhagic Telangiectasia. *N. Engl. J. Med.* 360:2143-2144. doi:10.1056/NEJMc0901421.

Bourdeau, A., D. J. Dumont, and M. Letarte. 1999. A murine model of hereditary hemorrhagic telangiectasia. *J. Clin. Invest.* 104:1343-1351. doi:10.1172/JCI8088.

Bourdeau, A., M. E. Faughnan, M. L. McDonald, A. D. Paterson, I. R. Wanless, and M. Letarte. 2001. Potential role of modifier genes influencing transforming growth factor-beta1 levels in the development of vascular defects in endoglin heterozygous mice with hereditary hemorrhagic telangiectasia. *Am. J. Pathol.* 158:2011-2020.

Canfield, A. E., M. J. Doherty, A. C. Wood, C. Farrington, B. Ashton, N. Begum, B. Harvey, A. Poole, M. E. Grant, and R. P. Boot-Handford. 2000. Role of pericytes in vascular calcification: a review. *Z Kardiol.* 89 Suppl 2:20-27.

Carvalho, R. L. C., L. Jonker, M.-J. Goumans, J. Larsson, P. Bouwman, S. Karlsson, P. ten Dijke, H. M. Arthur, and C. L. Mummery. 2004. Defective paracrine signalling by TGFbeta in yolk sac vasculature of endoglin mutant mice: a paradigm for hereditary haemorrhagic telangiectasia. *Development.* 131:6237-6247. doi:10.1242/dev.01529.

Chan, N. L. M., A. Bourdeau, S. Vera, S. Abdalla, M. Gross, J. Wong, U. Cymerman, A. D. Paterson, B. Mullen, and M. Letarte 2004. Umbilical vein and placental vessels from newborns with hereditary haemorrhagic telangiectasia type 1 genotype are normal despite reduced expression of endoglin. *Placenta.* 25:208-217. doi:10.1016/S0143-4004(03)00181-4.

Chi, J. T. 2003. Endothelial cell diversity revealed by global expression profiling. *Proceedings of the National Academy of Sciences.* 100:10623-10628. doi:10.1073/pnas.1434429100.

Choi, E. Y., E. Chavakis, M. A. Czabanka, H. F. Langer, L. Fraemohs, M. Economopoulou, R. K. Kundu, A. Orlandi, Y. Y. Zheng, D. A. Prieto, C. M. Ballantyne, S. L. Constant, W. C. Aird, T. Papayannopoulou, C. G. Gahmberg, M. C. Udey, P. Vajkoczy, T. Quertermous, S. Dimmeler, C. Weber, and T. Chavakis. 2008. Del-1, an Endogenous Leukocyte-Endothelial Adhesion Inhibitor, Limits Inflammatory Cell Recruitment. *Science.* 322:1101-1104. doi:10.1126/science.1165218.

Choi, K.-D., J. Yu, K. Smuga-Otto, G. Salvagiotto, W. Rehrauer, M. Vodyanik, J. Thomson, and I. Slukvin. 2009. Hematopoietic and endothelial differentiation of human induced pluripotent stem cells. *Stem Cells.* 27:559-567. doi:10.1634/stemcells.2008-0922.

Chong, D. C., Y. Koo, K. Xu, S. Fu, and O. Cleaver. 2011. Stepwise arteriovenous fate acquisition during mammalian vasculogenesis. *Dev. Dyn.* 240:2153-2165. doi: 10.1002/dvdy.22706.

Chung, Y., I. Klimanskaya, S. Becker, T. Li, M. Maserati, S.-J. Lu, T. Zdravkovic, D. Ilic, O. Genbacev, S. Fisher, A. Krtolica, and R. Lanza. 2008. Human embryonic stem cell lines generated without embryo destruction. *Cell Stem Cell.* 2:113-117. doi:10.1016/j.stem.2007.12.013.

Costa, M., K. Sourris, S. M. Lim, Q. C. Yu, C. E. Hirst, H. C. Parkington, V. J. Jokubaitis, A. E. Dear, H. B. Liu, S. J. Micallef, K. Koutsis, A. G. Elefanty, and E. G. Stanley. 2013. Derivation of endothelial cells from human embryonic stem cells in fully defined medium enables identification of lysophosphatidic acid and platelet activating factor as regulators of eNOS localization. *Stem Cell Res.* 10:103-117. doi:10.1016/j.scr.2012.10.003.

Crisan, M., S. Yap, L. Casteilla, C.-W. Chen, M. Corselli, T. S. Park, G. Andriolo, B. Sun, B. Zheng, L. Zhang, C. Norotte, P.-N. Teng, J. Traas, R. Schugar, B. M. Deasy, S. Badylak, H.-J. Búhring, J.-P. Giacobino, L. Lazzari, J. Huard, and B. Peault. 2008. A Perivascular Origin for Mesenchymal Stem Cells in Multiple Human Organs. *Cell Stem Cell.* 3:301-313. doi:10.1016/j.stem.2008.07.003.

Cunha, S. I., and K. Pietras. 2011. ALK1 as an emerging target for antiangiogenic therapy of cancer. *Blood.* 117: 6999-7006. doi:10.1182/blood-2011-01-330142.

Dambrot, C., S. van de Pas, L. van Zijl, B. Brandi, J. W. Wang, M. J. Schalij, R. C. Hoeben, D. E. Atsma, H. M. Mikkers, C. L. Mummery, and C. Freund. 2013. Polycistronic lentivirus induced pluripotent stem cells from skin biopsies after long term storage, blood outgrowth endothelial cells and cells from milk teeth. *Differentiation.* 85:101-109. doi:10.1016/j.diff.2013.01.001.

David, L., C. Mallet, M. Keramidas, N. Lamandé, J.-M. Gasc, S. Dupuis-Girod, H. Plauchu, J.-J. Feige, and S. Bailly. 2008. Bone morphogenetic protein-9 is a circulating vascular quiescence factor. *Circ. Res.* 102:914-922. doi:10.1161/CIRCRESAHA.107.165530.

Davis, R. P., S. Casini, C. W. van den Berg, M. Hoekstra, C. A. Remme, C. Dambrot, D. Salvatori, D. W. V. Oostwaard, A. A. M. Wilde, C. R. Bezzina, A. O. Verkerk, C. Freund, and C. L. Mummery. 2012. Cardiomyocytes Derived From Pluripotent Stem Cells Recapitulate Electrophysiological Characteristics of an Overlap Syndrome of Cardiac Sodium Channel Disease. *Circulation.* 125: 3079-3091. doi:10.1161/CIRCULATIONAHA.111.066092.

Ding, R., D. C. Darland, M. S. Parmacek, and P. A. D'Amore. 2004. Endothelial-mesenchymal interactions in vitro reveal molecular mechanisms of smooth muscle/pericyte differentiation. *Stem Cells Dev.* 13:509-520.

Doherty, M. J., and A. E. Canfield. 1999. Gene expression during vascular pericyte differentiation. *Crit. Rev. Eukaryot. Gene Expr.* 9:1-17.

Dyer, L., and C. Patterson. 2010. Development of the Endothelium: An Emphasis on Heterogeneity. *Semin. Thromb. Hemost.* 36:227-235. doi:10.1055/-0030-1253446.

Elliott, D. A., S. R. Braam, K. Koutsis, E. S. Ng, R. Jenny, E. L. Lagerqvist, C. Biben, T. Hatzistavrou, C. E. Hirst, Q. C. Yu, R. J. P. Skelton, D. W.-V. Oostwaard, S. M. Lim, O. Khammy, X. Li, S. M. Hawes, R. P. Davis, A. L. Goulburn, R. Passier, O. W. J. Prall, J. M. Haynes, C. W. Pouton, D. M. Kaye, C. L. Mummery, A. G. Elefanty, and E. G. Stanley. 2011. NKX2-5(eGFP/w) hESCs for isolation of human cardiac progenitors and cardiomyocytes. *Nat. Methods.* doi:10.1038/nmeth.1740.

Evensen, L., D. R. Micklem, W. Link, and J. B. Lorens. 2010. A novel imaging-based high-throughput screening approach to anti-angiogenic drug discovery. *Cytometry A.* 77:41-51. doi:10.1002/cyto.a.20808.

Evensen, L., W. Link, and J. B. Lorens. 2013. Image-based high-throughput screening for inhibitors of angiogenesis. *Methods Mol. Biol.* 931:139-151. doi: 10.1007/978-1-62703-056-4_8.

Fernandez-L, A., F. Sanz-Rodriguez, R. Zarrabeitia, A. Pérez-Molino, R. P. Hebbel, J. Nguyen, C. Bernabéu, and L.-M. Botella. 2005. Blood outgrowth endothelial cells from Hereditary Haemorrhagic Telangiectasia patients reveal abnormalities compatible with vascular lesions. *Cardiovasc. Res.* 68:235-248. doi:10.1016/j.cardiores.2005.06.009.

Freund, C., D. Ward-van Oostwaard, J. Monshouwer-Kloots, S. van den Brink, M. van Rooijen, X. Xu, R. Zweigerdt, C. Mummery, and R. Passier. 2008. Insulin Redirects Differentiation from Cardiogenic Mesoderm and Endoderm to Neuroectoderm in Differentiating Human Embryonic Stem Cells. *Stem Cells.* 26:724-733. doi:10.1634/stemcells.2007-0617.

Freund, C., R. P. Davis, K. Gkatzis, D. W.-V. Oostwaard, and C. L. Mummery. 2010. The first reported generation of human induced pluripotent stem cells (iPS cells) and iPS cell-derived cardiomyocytes in the Netherlands. *Neth Heart J.* 18:51-54.

Gallione, C. J., G. M. Repetto, E. Legius, A. K. Rustgi, S. L. Schelley, S. Tejpar, G. Mitchell, É. Drouin, C. J. Westermann, and D. A. Marchuk. 2004. A combined syndrome of juvenile polyposis and hereditary haemorrhagic telangiectasia associated with mutations in MADH4 (SMAD4). *The Lancet.* 363:852-859. doi: 10.1016/S0140-6736(04)15732-2.

Gallione, C. J., J. A. Richards, T. G. W. Letteboer, D. Rushlow, N. L. Prigoda, T. P. Leedom, A. Ganguly, A. Castells, J. K. Ploos van Amstel, C. J. J. Westermann, R. E. Pyeritz, and D. A. Marchuk. 2006. SMAD4 mutations found in unselected HHT patients. *J. Med. Genet.* 43:793-797. doi:10.1136/jmg.2006.041517.

Gordon, E. J., N. W. Gale, and N. L. Harvey. 2008. Expression of the hyaluronan receptor LYVE-1 is not restricted to the lymphatic vasculature; LYVE-1 is also expressed on embryonic blood vessels. *Dev. Dyn.* 237:1901-1909. doi:10.1002/dvdy.21605.

Guttmacher, A. E., D. A. Marchuk, and R. I. White Jr. 1995. Hereditary Hemorrhagic Telangiectasia. *N. Engl. J. Med.* 333:918-924. doi:10.1056/NEJM199510053331407.

Hexum, M. K., X. Tian, and D. S. Kaufman. 2011. In Vivo Evaluation of Putative Hematopoietic Stem Cells Derived from Human Pluripotent Stem Cells. In Methods in Molecular Biology. Humana Press, Totowa, N.J. 433-447.

Hill, K. L., and D. S. Kaufman. 2007. Hematopoietic Differentiation of Human Embryonic Stem Cells by Cocultivation with Stromal Layers. John Wiley & Sons, Inc., Hoboken, N.J., USA.

Hill, K. L., P. Obrtlikova, D. F. Alvarez, J. A. King, S. A. Keirstead, J. R. Allred, and D. S. Kaufman. 2010. Human embryonic stem cell—derived vascular progenitor cells capable of endothelial and smooth muscle cell function. *Exp. Hematol.* 38:246-257.e1. doi:10.1016/j.exphem.2010.01.001.

Hirschi, K. K., and P. A. D'Amore. 1996. Pericytes in the microvasculature. *Cardiovasc. Res.* 32:687-698.

James, D., H.-S. Nam, M. Seandel, D. Nolan, T. Janovitz, M. Tomishima, L. Studer, G. Lee, D. Lyden, R. Benezra, N. Zaninovic, Z. Rosenwaks, S. Y. Rabbany, and S. Rafii. 2010. Expansion and maintenance of human embryonic stem cell-derived endothelial cells by TGFbeta inhibition is Id1 dependent. *Nat. Biotechnol.* 28:161-166. doi: 10.1038/nbt.1605.

Kane, N. M., M. Meloni, H. L. Spencer, M. A. Craig, R. Strehl, G. Milligan, M. D. Houslay, J. C. Mountford, C. Emanueli, and A. H. Baker. 2010. Derivation of Endothelial Cells From Human Embryonic Stem Cells by Directed Differentiation: Analysis of MicroRNA and Angiogenesis In Vitro and In Vivo. *Arterioscler. Thromb. Vasc. Biol.* 30:1389-1397. doi:10.1161/ATVBAHA.110.204800.

Kano, M. R., Y. Bae, C. Iwata, Y. Morishita, M. Yashiro, M. Oka, T. Fujii, A. Komuro, K. Kiyono, M. Kaminishi, K. Hirakawa, Y. Ouchi, N. Nishiyama, K. Kataoka, and K. Miyazono. 2007. Improvement of cancer-targeting therapy, using nanocarriers for intractable solid tumors by inhibition of TGF-beta signaling. *Proc Natl Acad Sci USA.* 104:3460-3465. doi:10.1073/pnas.0611660104.

Karunamuni, G., K. Yang, Y. Q. Doughman, J. Wikenheiser, D. Bader, J. Barnett, A. Austin, P. Parsons-Wingerter, and M. Watanabe. 2009. Expression of Lymphatic Markers During Avian and Mouse Cardiogenesis. *Anat Rec.* 293: 259-270. doi:10.1002/ar.21043.

Kennedy, M., G. Awong, C. M. Sturgeon, A. Ditadi, R. LaMotte-Mohs, J. C. Zúñiga-Pflücker, and G. Keller. 2012. T Lymphocyte Potential Marks the Emergence of Definitive Hematopoietic Progenitors in Human Pluripotent Stem Cell Differentiation Cultures. *Cell Reports.* doi:10.1016/j.celrep.2012.11.003.

Kinnear, C., W. Y. Chang, S. Khattak, A. Hinek, T. Thompson, D. de Carvalho Rodrigues, K. Kennedy, N. Mahmut, P. Pasceri, W. L. Stanford, J. Ellis, and S. Mital. 2013. Modeling and rescue of the vascular phenotype of Williams-Beuren syndrome in patient induced pluripotent stem cells. *Stem Cells Transl Med.* 2:2-15. doi:10.5966/sctm.2012-0054.

Lacorre, D. A. 2004. Plasticity of endothelial cells: rapid dedifferentiation of freshly isolated high endothelial venule endothelial cells outside the lymphoid tissue microenvironment. *Blood.* 103:4164-4172. doi:10.1182/blood-2003-10-3537.

Langer, H. F., V. V. Orlova, C. Xie, S. Kaul, D. Schneider, A. S. Lonsdorf, M. Fahrleitner, E. Y. Choi, V. Dutoit, M. Pellegrini, S. Grossklaus, P. P. Nawroth, G. Baretton, S. Santoso, S. T. Hwang, B. Arnold, and T. Chavakis. 2011. A novel function of junctional adhesion molecule-C in mediating melanoma cell metastasis. *Cancer Res.* 71:4096-4105. doi:10.1158/0008-5472.CAN-10-2794.

lebrin, F., M.-J. Goumans, L. Jonker, R. L. C. Carvalho, G. Valdimarsdottir, M. Thorikay, C. Mummery, H. M. Arthur, and P. ten Dijke. 2004. Endoglin promotes endothelial cell proliferation and TGF-beta/ALK1 signal transduction. *The EMBO Journal.* 23:4018-4028. doi: 10.1038/sj.emboj.7600386.

Lebrin, F., S. Srun, K. Raymond, S. Martin, S. van den Brink, C. Freitas, C. Breant, T. Mathivet, B. Larrivee, J. L. Thomas, H. M. Arthur, C. J. Westermann, F. Disch, J. J. Mager, R. J. Snijder, A. Eichmann, and C. L. Mummery. 2010. Thalidomide stimulates vessel maturation and reduces epistaxis in individuals with hereditary hemorrhagic telangiectasia. *Nat. Med.* 16:420-428. doi:10.1038/nm.2131.

Leitch, H. G., K. Blair, W. Mansfield, H. Ayetey, P. Humphreys, J. Nichols, M. A. Surani, and A. Smith. 2010. Embryonic germ cells from mice and rats exhibit properties consistent with a generic pluripotent ground state. *Development.* 137:2279-2287. doi:10.1242/dev.050427.

Letteboer, T. G. W. 2005. Genotype-phenotype relationship in hereditary haemorrhagic telangiectasia. *J. Med. Genet.* 43:371-377. doi:10.1136/jmg.2005.035451.

Li, Z., S. Hu, Z. Ghosh, Z. Han, and J. C. Wu. 2011. Functional Characterization and Expression Profiling of Human Induced Pluripotent Stem Cell- and Embryonic Stem Cell-Derived Endothelial Cells. *Stem Cells Dev.* 20:1701-1710. doi:10.1089/scd.2010.0426.

Lippmann, E. S., S. M. Azarin, J. E. Kay, R. A. Nessler, H. K. Wilson, A. Al-Ahmad, S. P. Palecek, and E. V. Shusta. 2012. Derivation of blood-brain barrier endothelial cells from human pluripotent stem cells. *Nat. Biotechnol.* 30:783-791. doi:10.1038/nbt.2247.

Mahmoud, M., K. R. Allinson, Z. Zhai, R. Oakenfull, P. Ghandi, R. H. Adams, M. Fruttiger, and H. M. Arthur. 2010. Pathogenesis of Arteriovenous Malformations in the Absence of Endoglin. *Circ. Res.* 106:1425-1433. doi:10.1161/CIRCRESAHA.109.211037.

Mao, J.-H., E. F. Saunier, J. P. de Koning, M. M. McKinnon, M. N. Higgins, K. Nicklas, H.-T. Yang, A. Balmain, and R. J. Akhurst. 2006. Genetic variants of Tgfb1 act as context-dependent modifiers of mouse skin tumor susceptibility. *Proc Natl Acad Sci USA.* 103:8125-8130. doi:10.1073/pnas.0602581103.

Müller, F.-J., B. M. Schuldt, R. Williams, D. Mason, G. Altun, E. P. Papapetrou, S. Danner, J. E. Goldmann, A. Herbst, N. O. Schmidt, J. B. Aldenhoff, L. C. Laurent, and J. F. Loring. 2011. A bioinformatic assay for pluripotency in human cells. *Nat. Methods.* 8:315-317. doi:10.1038/nmeth.1580.

Ng, E. S., R. Davis, E. G. Stanley, and A. G. Elefanty. 2008. A protocol describing the use of a recombinant protein-based, animal product-free medium (APEL) for human embryonic stem cell differentiation as spin embryoid bodies. *Nat Protoc.* 3:768-776. doi:10.1038/nprot.2008.42.

Nolan-Stevaux, O., Nolan-Stevaux, O., W. Zhong, W. Zhong, S. Culp, S. Culp, K. Shaffer, K. Shaffer, J. Hoover, J. Hoover, D. Wickramasinghe, D. Wickramasinghe, A. Ruefli-Brasse, and A. Ruefli-Brasse. 2012. Endoglin Requirement for BMP9 Signaling in Endothelial Cells Reveals New Mechanism of Action for Selective Anti-Endoglin Antibodies. *PLoS ONE.* 7:e50920. doi:10.1371/journal.pone.0050920.

Nomura-Kitabayashi, A., G. A. Anderson, G. Sleep, J. Mena, A. Karabegovic, S. Karamath, M. Letarte, and M. C. Puri. 2009. Endoglin is dispensable for angiogenesis, but required for endocardial cushion formation in the midgestation mouse embryo. *Dev. Biol.* 335:66-77. doi:10.1016/j.ydbio.2009.08.016.

Nourse, M. B., D. E. Halpin, M. Scatena, D. J. Mortisen, N. L. Tulloch, K. D. Hauch, B. Torok-Storb, B. D. Ratner, L. Pabon, and C. E. Murry. 2009. VEGF Induces Differentiation of Functional Endothelium From Human Embryonic Stem Cells: Implications for Tissue Engineering. *Arterioscler. Thromb. Vasc. Biol.* 30:80-89. doi:10.1161/ATVBAHA.109.194233.

Orlova, V. V., M. Economopoulou, F. Lupu, S. Santoso, and T. Chavakis. 2006. Junctional adhesion molecule-C regulates vascular endothelial permeability by modulating VE-cadherin-mediated cell-cell contacts. *J. Exp. Med.* 203:2703-2714.

Orlova, V. V., Z. Liu, M. J. Goumans, and P. ten Dijke. 2011. Controlling angiogenesis by two unique TGF-β type I receptor signaling pathways. *Histol. Histopathol.* 26:1219-1230.

Pera, M. F. 2008. Stem cells. A new year and a new era. *Nature.* 451:135-136. doi:10.1038/451135a.

Reubinoff, B. E., M. F. Pera, C. Y. Fong, A. Trounson, and A. Bongso. 2000. Embryonic stem cell lines from human blastocysts: somatic differentiation in vitro. *Nat. Biotechnol.* 18:399-404. doi:10.1038/74447.

Scharpfenecker, M., M. van Dinther, Z. Liu, R. L. van Bezooijen, Q. Zhao, L. Pukac, C. W. G. M. Löwik, and P. ten Dijke. 2007. BMP-9 signals via ALK1 and inhibits bFGF-induced endothelial cell proliferation and VEGF-stimulated angiogenesis. *J. Cell. Sci.* 120:964-972. doi:10.1242/jcs.002949.

Schlondorff, D. 1987. The glomerular mesangial cell: an expanding role for a specialized pericyte. *FASEB J.* 1:272-281.

Seok, J., H. S. Warren, A. G. Cuenca, M. N. Mindrinos, H. V. Baker, W. Xu, D. R. Richards, G. P. McDonald-Smith, H. Gao, L. Hennessy, C. C. Finnerty, C. M. López, S. Honari, E. E. Moore, J. P. Minei, J. Cuschieri, P. E. Bankey, J. L. Johnson, J. Sperry, A. B. Nathens, T. R. Billiar, M. A. West, M. G. Jeschke, M. B. Klein, R. L. Gamelli, N. S. Gibran, B. H. Brownstein, C. Miller-Graziano, S. E. Calvano, P. H. Mason, J. P. Cobb, L. G. Rahme, S. F. Lowry, R. V. Maier, L. L. Moldawer, D. N. Herndon, R. W. Davis, W. Xiao, R. G. Tompkins, Large Scale Collaborative Research Program Inflammation and Host Response to Injury. 2013. Genomic responses in mouse models poorly mimic human inflammatory diseases. *Proc Natl Acad Sci USA.* 110:3507-3512. doi:10.1073/pnas.1222878110.

Seon, B. K., A. Haba, F. Matsuno, N. Takahashi, M. Tsujie, X. She, N. Harada, S. Uneda, T. Tsujie, H. Toi, H. Tsai, and Y. Haruta. 2011. Endoglin-targeted cancer therapy. *Curr Drug Deliv.* 8:135-143.

Shepro, D., and N. M. Morel. 1993. Pericyte physiology. *FASEB J.* 7:1031-1038.

Shiozaki, K., N. Harada, W. R. Greco, A. Haba, S. Uneda, H. Tsai, and B. K. Seon. 2006. Antiangiogenic chimeric anti-endoglin (CD105) antibody: pharmacokinetics and immunogenicity in nonhuman primates and effects of doxorubicin. *Cancer Immunol. Immunother.* 55:140-150. doi:10.1007/s00262-005-0691-4.

Shovlin, C. L. 2010. Hereditary haemorrhagic telangiectasia: pathophysiology, diagnosis and treatment. *Blood Rev.* 24:203-219. doi:10.1016/j.blre.2010.07.001.

Sims, D. E. 2000. Diversity within pericytes. *Clin Exp. Pharmacol. Physiol.* 27:842-846.

Smith, A. G. 2001. Embryo-derived stem cells: of mice and men. *Annu. Rev. Cell Dev. Biol.* 17:435-462. doi:10.1146/annurev.cellbio.17.1.435.

Srinivasan, S., M. A. Hanes, T. Dickens, M. E. M. Porteous, S. P. Oh, L. P. Hale, and D. A. Marchuk. 2003. A mouse model for hereditary hemorrhagic telangiectasia (HHT) type 2. *Hum. Mol. Genet.* 12:473-482.

Tang, Y. 2003. Genetic modifiers interact with maternal determinants in vascular development of Tgfb1−/−mice. *Hum. Mol. Genet.* 12:1579-1589. doi:10.1093/hmg/ddg164.

Thomson, J. A., and J. S. Odorico. 2000. Human embryonic stem cell and embryonic germ cell lines. *Trends Biotechnol.* 18:53-57.

Thomson, J. A., and V. S. Marshall. 1998. Primate embryonic stem cells. *Curr. Top. Dev. Biol.* 38:133-165.

Thomson, J. A., J. Itskovitz-Eldor, S. S. Shapiro, M. A. Waknitz, J. J. Swiergiel, V. S. Marshall, and J. M. Jones. 1998. Embryonic stem cell lines derived from human blastocysts. *Science.* 282:1145-1147.

Thomson, J. A., J. Kalishman, T. G. Golos, M. Durning, C. P. Harris, R. A. Becker, and J. P. Hearn. 1995. Isolation of a primate embryonic stem cell line. *Proc Natl Acad Sci USA.* 92:7844-7848.

Tian, X., M. K. Hexum, V. R. Penchev, R. J. Taylor, L. D. Shultz, and D. S. Kaufman. 2009. Bioluminescent Imaging Demonstrates That Transplanted Human Embryonic Stem Cell-Derived CD34+Cells Preferentially Develop into Endothelial Cells. *Stem Cells.* 27:2675-2685. doi: 10.1002/stem.204.

Urness, L. D., L. K. Sorensen, and D. Y. Li. 2000. Arteriovenous malformations in mice lacking activin receptor-like kinase-1. *Nat. Genet.* 26:328-331. doi:10.1038/81634.

van de Stolpe, A., S. van den Brink, M. van Rooijen, D. Ward-van Oostwaard, W. van Inzen, I. Slaper-Cortenbach, B. Fauser, N. van den Hout, S. Weima, R. Passier, N. Smith, C. Denning, and C. Mummery. 2005. Human embryonic stem cells: toward therapies for cardiac disease. Derivation of a Dutch human embryonic stem cell line. *Reproductive BioMedicine Online.* 11:476-485. doi: 10.1016/S1472-6483(10)61144-3.

van den Driesche, S., C. L. Mummery, and C. J. Westermann. 2003. Hereditary hemorrhagic telangiectasia: an update on transforming growth factor beta signaling in vasculogenesis and angiogenesis. *Cardiovasc. Res.* 58:20-31.

van Laake, L. W., S. van den Driesche, S. Post, A. Feijen, M. A. Jansen, M. H. Driessens, J. J. Mager, R. J. Snijder, C. J. J. Westermann, P. A. Doevendans, C. J. A. van Echteld, P. ten Dijke, H. M. Arthur, M. J. Goumans, F. Lebrin, and C. L. Mummery. 2006. Endoglin Has a Crucial Role in Blood Cell-Mediated Vascular Repair. *Circulation.* 114: 2288-2297. doi:10.1161/CIRCULATIONAHA.106.639161.

Watabe, T., A. Nishihara, K. Mishima, J. Yamashita, K. Shimizu, K. Miyazawa, S.-I. Nishikawa, and K. Miyazono. 2003. TGF-beta receptor kinase inhibitor enhances growth and integrity of embryonic stem cell-derived endothelial cells. *J. Cell Biol.* 163:1303-1311. doi: 10.1083/jcb.200305147.

Watabe, T., J. K. Yamashita, K. Mishima, and K. Miyazono. 2006. TGF-beta signaling in embryonic stem cell-derived endothelial cells. *Methods Mol. Biol.* 330:341-351. doi: 10.1385/1-59745-036-7:341.

White, M. P., A. J. Rufaihah, L. Liu, Y. T. Ghebremariam, K. N. Ivey, J. P. Cooke, and D. Srivastava. 2012. Limited Gene Expression Variation in Human Embryonic Stem Cell and Induced Pluripotent Stem Cell-Derived Endothelial Cells. *Stem Cells.* 31:92-103. doi:10.1002/stem.1267.

Xu, C., M. S. Inokuma, J. Denham, K. Golds, P. Kundu, J. D. Gold, and M. K. Carpenter. 2001. Feeder-free growth of undifferentiated human embryonic stem cells. *Nat. Biotechnol.* 19:971-974. doi:10.1038/nbt1001-971.

Yamanaka, S. 2009. A Fresh Look at iPS Cells. *Cell.* 137:13-17. doi:10.1016/j.cell2009.03.034.

Yamanaka, S. 2012. Induced Pluripotent Stem Cells: Past, Present, and Future. *Cell Stem Cell.* 10:678-684. doi: 10.1016/j.stem.2012.05.005.

Ying, Q. L., J. Nichols, I. Chambers, and A. Smith. 2003. BMP induction of Id proteins suppresses differentiation and sustains embryonic stem cell self-renewal in collaboration with STAT3. *Cell.* 115:281-292.

Yu, J., and J. A. Thomson. 2008. Pluripotent stem cell lines. *Genes & Development.* 22:1987-1997. doi:10.1101/gad.1689808.

Yu, Q. C., C. E. Hirst, M. Costa, E. S. Ng, J. V. Schiesser, K. Gertow, E. G. Stanley, and A. G. Elefanty. 2012. APELIN promotes hematopoiesis from human embryonic stem cells. *Blood.* 119:6243-6254. doi:10.1182/blood-2011-12-396093.

Zakkar, M., L. A. Luong, H. Chaudhury, O. Ruud, P. P. Punjabi, J. R. Anderson, J. W. Mullholand, A. T. Clements, R. Krams, N. Foin, T. Athanasiou, E. L. S. Leen, J. C. Mason, D. O. Haskard, and P. C. Evans. 2011. Dexamethasone Arterializes Venous Endothelial Cells by Inducing Mitogen-Activated Protein Kinase Phosphatase-1: A Novel Antiinflammatory Treatment for Vein Grafts? *Circulation.* 123:524-532. doi:10.1161/CIRCULATIONAHA.110.979542.

The invention claimed is:

1. A method for producing an in vitro cell culture comprising endothelial cells derived from in vitro differentiated pluripotent stein cells and smooth muscle cells derived from in vitro differentiated pluripotent stem cells or derived from pericytes, the method comprising the following steps:
   (a) culturing pluripotent stem cells in defined medium comprising ActivinA, BMP4, VEGF, and a canonical WNT ligand or GSK3 inhibitor, to produce a culture comprising differentiated cells;
   (b) culturing the cells obtained in step (a) in defined medium containing VEGF and a TGF{beta} signaling inhibitor to produce endothelial cells; and
   (c) culturing the endothelial cells obtained in step (b) with smooth muscle cells derived from in vitro differentiated pluripotent stem cells or derived from pericytes.

2. The method according to claim 1, further comprising: collecting the cells produced in step (b) and obtaining therefrom a collection of cells that comprises more than 90% endothelial cells.

3. The method according to claim 1, further comprising: collecting the cells produced in step (b) and obtaining therefrom a collection of cells that comprises more than 90% pericytes.

4. The method according to claim 2, wherein said collection of cells is obtained by separating the cells of step (b) on the basis of CD31 expression.

5. The method according to claim 3, further comprising: providing the endothelial cells with a cell storage medium and storing the endothelial cells at a temperature of −70° C. or less.

6. The method according to claim 2, further comprising: culturing said endothelial cells together with smooth muscle cells.

7. A method of producing an in vitro cell culture comprising endothelial cells and smooth muscle cells, wherein the endothelial cells are able to integrate into a vascular network in vivo, the method comprising:
   (a) culturing pluripotent stem cells in a defined medium comprising ActivinA, BMP4, VEGF, and a canonical WNT ligand or GSK3 inhibitor, to produce a culture comprising differentiated cells;
   (b) culturing the cells of step (a) in defined medium containing VEGF and a TGF(beta) signaling inhibitor to produce endothelial cells; and
   (c) culturing the endothelial cells obtained in step (b) with smooth muscle cells.

8. The method according to claim 2, wherein the collection of cells comprises more than 90% endothelial cells based on the expression of CD31, CD34 or VECadherin.

9. The method according to claim 3, wherein the collection of cells comprises more than 90% pericytes based on the expression of CD31, CD34 or VECadherin.

10. The method according to claim 4, wherein separating the cells of step (b) on the basis of CD31 expression is by means of beads comprising a CD31 binding antibody.

11. A method for producing an in vitro cell culture comprising purified endothelial cells and purified smooth muscle cells, wherein the cell culture comprises a capillary network comprising the endothelial cells and the smooth muscle cells, the method comprising:
   deriving endothelial cells from in vitro differentiated induced pluripotent stem cells (iPSCs) and purifying the endothelial cells,
   deriving smooth muscle cells from in vitro differentiated induced pluripotent stem cells or from pericytes that are derived from in vitro differentiated induced pluripotent stem cells and purifying the smooth muscle cells, and
   culturing the purified endothelial cells together with the purified smooth muscle cells.

12. The method according to claim 11, wherein the endothelial cells and the smooth muscle cells are derived from induced pluripotent stem cells (iPSCs) generated from skin biopsy fibroblasts or blood outgrowth endothelial cells.

13. The method according to claim 11, wherein the endothelial cells are able to integrate into a vascular network in vivo.

14. The method according to claim 11, wherein the endothelial cells have a genetic defect that in vivo exhibits a phenotype in vasculature.

15. The method according to claim 11, wherein the smooth muscle cells have a genetic defect that in vivo exhibits a phenotype in vasculature.

16. The method according to claim 11, further comprising:
   isolating the endothelial cells and the smooth muscle cells, and
   cryopreserving the endothelial cells and the smooth muscle cells.

17. The method according to claim 11, further comprising:
   screening the cell culture for angiogenic and anti-angiogenic compounds.

* * * * *